US005655516A

United States Patent [19]

Goodman et al.

[11] Patent Number: 5,655,516

[45] Date of Patent: *Aug. 12, 1997

[54] DELIVERY OF AEROSOL MEDICATIONS FOR INSPIRATION

[75] Inventors: David E. Goodman, Brookline; Reid M. Rubsamen, Boston, both of Mass.

[73] Assignee: Aradigm Corporation, Hayward, Calif.

[*] Notice: The term of this patent shall not extend beyond the expiration date of Pat. No. 5,404,871.

[21] Appl. No.: 636,958

[22] Filed: Apr. 24, 1996

Related U.S. Application Data

[60] Continuation of Ser. No. 457,148, Jun. 1, 1995, which is a division of Ser. No. 353,162, Dec. 9, 1994, which is a continuation of Ser. No. 664,758, Mar. 5, 1991, Pat. No. 5,404,871.

[51] Int. Cl.$^6$ .......... A61M 11/00

[52] U.S. Cl. .......... 128/200.14; 128/200.23; 128/204.23; 128/205.23

[58] Field of Search .......... 128/200.14, 200.23, 128/204.23, 205.23

[56] References Cited

U.S. PATENT DOCUMENTS

| | | | |
|---|---|---|---|
| 3,187,748 | 6/1965 | Mitchell et al. | 128/200.23 |
| 3,565,070 | 2/1971 | Hanson et al. | 128/200.23 |
| 3,658,059 | 4/1972 | Steil | 128/200.21 |
| 3,814,297 | 6/1974 | Warren | 222/402.13 |
| 3,826,413 | 7/1974 | Warren | 222/402.13 |
| 3,991,304 | 11/1976 | Hillsman | 364/413.04 |
| 4,484,577 | 11/1984 | Sackner et al. | 128/203.28 |
| 4,524,769 | 6/1985 | Wetterlin | 128/203.15 |
| 4,592,348 | 6/1986 | Waters, IV et al. | 128/200.23 |
| 4,648,393 | 3/1987 | Landis et al. | 128/200.23 |
| 4,677,975 | 7/1987 | Edgar et al. | 128/200.14 |
| 4,790,305 | 12/1988 | Zoltan et al. | 128/200.23 |
| 4,803,978 | 2/1989 | Johnson et al. | 128/200.23 |
| 4,852,582 | 8/1989 | Pell | 128/716 |
| 4,922,901 | 5/1990 | Brooks et al. | 128/203.26 |
| 4,926,852 | 5/1990 | Zoltan et al. | 128/200.23 |
| 4,932,402 | 6/1990 | Snook et al. | 128/204.23 |
| 5,363,842 | 11/1994 | Mishelevich et al. | 128/200.14 |
| 5,404,871 | 4/1995 | Goodman et al. | 128/200.14 |

OTHER PUBLICATIONS

Newman et al., 1981. "Deposition of Pressurized Aerosols in the Human Respiratory Tract," *Thorax* 36:52–5.

Newman et al., 1981. "Deposition of Pressurized Suspension Aeorsols Inhaled Through Extension Devices," *Am. Rev. Respir. Dis.* 124:317–20.

Newman et al. 1981. "How should a Pressurized Beta-adrenergic Bronchodilator Be Inhaled?," *Eur. J. Respir. Dis.* 62:3–21.

Byron (ed.). 1990. Respiratory Drug Delivery. CRC Press, Florida.

Kohler, D. 1990. "Aerosols for Systemic Treatment," *Lung* Suppl.:677–84.

*Primary Examiner*—Aaron J. Lewis
*Attorney, Agent, or Firm*—Karl Bozicevic; Fish and Richardson P.C.

[57] ABSTRACT

Apparatus and methods for delivering an amount of aerosolized medicine for inspiration by a patient in response to the occurrence of appropriate delivery point or points in the patient's detected breath flow. The aerosol medication may be administered as one or more pulses having a pulse width, shape, and frequency that will maximize the respirable fraction of the aerosolized compound being administered. The delivery point or points may be predetermined or determined from a prior inspiratory flow for depositing the selected medication at one or more desired locations in the patient's airway. Determined delivery points are recursively lowered for each inspiratory flow that does not satisfy one of the predetermined and previously lowered threshold. Changes in the patient's breath flow patterns during the course of an aerosolized medication inspiration therapy program may be detected and used to adjust the controlled amount of medication to be delivered in a given administration and/or to inform the patient of the patient's condition or change in condition. The device also may contain a library of administration protocols or operating parameters for different medications and a means for identifying from the canister the medicinal contents of the canister for customizing operation of the apparatus.

9 Claims, 17 Drawing Sheets

DELIVERY OF AEROSOL MEDICATIONS FOR INSPIRATION

CROSS-REFERENCES TO RELATED APPLICATIONS

This application is a continuation of our earlier filed application Ser. No. 08/457,148, filed Jun. 1, 1995, still pending, which is a divisional of application Ser. No. 08/353,162, filed Dec. 9, 1994, still pending, which is a continuation of application Ser. No. 07/664,758, filed Mar. 5, 1991, now issued as U.S. Pat. No. 5,404,871 to which we claim priority under 35 USC §120 and which are incorporated herein by reference in their entirety.

This invention relates to delivery of aerosolized materials and specifically to improvements in the delivery of aerosolized medications for inspiration by patients for more effective therapeutic and diagnostic purposes.

BACKGROUND OF THE INVENTION

Devices for the delivery of aerosol medications for inspiration are known. One such device is a metered dose inhaler which delivers the same dosage of medication to the patient upon each actuation of the device. Metered dose inhalers typically include a canister containing a reservoir of medication and propellant under pressure and a fixed volume metered dose chamber. The canister is inserted into a receptacle in a body or base having a mouthpiece or nosepiece for delivering medication to the patient. The patient uses the device by manually pressing the canister into the body to close a filling valve and capture a metered dose of medication inside the chamber and to open a release valve which releases the captured, fixed volume of medication in the dose chamber to the atmosphere as an aerosol mist. Simultaneously, the patient inhales through the mouthpiece to entrain the mist into the airway. The patient then releases the canister so that the release valve closes and the filling valve opens to refill the dose chamber for the next administration of medication. See, for example, U.S. Pat. No. 4,896,832 and a product available from 3M Healthcare known as Aerosol Sheathed Actuator and Cap.

A major problem with metered dose inhalers is that the patient frequently actuates the device at the incorrect time during inspiratory flow to obtain the benefits of the intended drug therapy, e.g., too early or too late in the flow cycle or during expiration.

Another device is the breath actuated metered dose inhaler which operates to provide automatically a metered dose in response to the patient's inspiratory effort. One style of breath actuated device releases a dose when the inspiratory effort moves a mechanical lever to trigger the release valve. Another style releases the dose when the detected flow rises above a preset threshold, as detected by a hot wire anemometer. See, for example, U.S. Pat. Nos. 3,187,748; 3,565,070; 3,814,297; 3,826,413; 4,592,348; 4,648,393; 4,803,978.

Existing breath actuated devices have not, however, been entirely successful in overcoming the problem of timing drug delivery to the patient's inspiration. For one thing, breath activated drug delivery is triggered on crossing a fixed threshold inspiratory effort. Thus, an inspiration effort may be sufficient to release a metered dose, but the inspiratory flow following the release may not be sufficient to cause the aerosol medication to pass into the desired portion of the patient's airways. Another problem exists with some patients whose inspiratory effort may not be sufficient to rise above the threshold to trigger the release valve at all.

Other attempts have been made to solve the patient inspiration synchronization problem. U.S. Pat. No. 4,484,577 refers to releasing a dosage of drug into a bag for the patient to inhale and using a bidirectional reed whistle to indicate to the patient the maximum rate of inhalation for desired delivery of the drug or a flow restrictor to prevent the patient from inhaling too rapidly. U.S. Pat. No. 3,991,304 refers to using biofeedback techniques to train the patient to adopt a breathing pattern including tidal volume, respiratory frequency, and inspiration and expiration times for efficient delivery of aerosols for inhalation therapy. U.S. Pat. No. 4,677,975 refers to detecting the beginning of inspiration, and using audible signals and preselected time delays which are gated on the detection of inspiratory flow to indicate to the patient when to inspire and expire, and delivering inhalable material to the mouthpiece a selected time after the detected onset of flow. U.S. Pat. No. 4,932,402 refers to modifying continuous gas flow devices by determining the patient's breathing cycle rate over a period of several breaths and providing pulses of oxygen or other medicinal gases for inhalation during inspiration such that the volume of gas delivered changes in response to changes in the patient's breathing rate. However, these devices also suffer from improper operation by patients who do not conform their breathing to the instructed breathing pattern or whose inspiratory flow does not provide adequate delivery of the medication.

It also is noted that devices exist to deliver dry powdered drugs to the patient's airways as in U.S. Pat. No. 4,524,769 and to deliver an aerosol by heating a solid aerosol precursor material as in U.S. Pat. No. 4,922,901. These devices typically operate to deliver the drug during the early stages of the patient's inspiration by relying on the patient's inspiratory flow to draw the drug out of the reservoir into the airway or to actuate a heating element to vaporize the solid aerosol precursor. However, these devices are subject to improper and variable delivery of the powdered drug or vaporized aerosol, depending on the variations of the patient's inspiration effort and any sustained flow.

A problem with metered dose inhalers is that patients' abilities to use or to be trained to use the device properly vary widely. Thus, whether or not the device is breath actuated, patients may inspire too little medication. Further, in the event that a patient administers an additional dose to compensate for an actual or perceived partial prior dose, too much medication may be inspired. This produces inconsistent and hence inadequate therapy.

Another problem with metered dose inhalers is that they always provide a fixed, uniform dose of medication which is delivered at the time the device is activated. However, in many inhalation therapy programs a gradual reduction in the dose would be more appropriate for the treating the patient's gradually improved condition. In addition, delivery of the dose at different points in the inspiratory flow cycle may be more efficacious than delivery of a single bolus.

It is known that the therapeutic effect of an inhaled drug is affected by where it is deposited in the lungs. The human respiratory tract branches about twenty-three times. The resulting bronchial tree thus contains airway segments having lengths that vary from 12 cm to 0.05 cm, and corresponding diameters that vary from 1.80 cm to 0.041 cm, for an average adult. The smallest airways give rise to the alveoli, the air sacs in contact with the blood stream where gas exchange occurs.

The bronchial tree can be broadly divided into two groups, small airway populations and large airway populations. Specific drugs have different optimal delivery sites within the bronchial tree. For example, bronchodilators used for treating asthma should be deposited in both large and small airways, whereas drugs intended for systemic absorption such as peptides, e.g., insulin, should be deposited as far in the peripheral large airways of the lung as possible.

Studies in Bryon (ed.), *Respiratory Drug Delivery*, CRC Press, Inc. (1990); Newman et al., *Thorax* 1981, 36:52–55; Newman et al. *Thorax*, 1980, 35:234; Newman et al., *Eur. J. Respir. Dis.*, 1981, 62:3–21; and Newman et al., *Am. Rev. Respir. Dis.*, 1981, 124:317–320 indicate that during a single breath of an aerosol compound, only about ten percent of the total aerosol material presented is deposited into the lungs and that the location of deposition in the lung depends upon 1) breath parameters such as volume of inspiration, inspiratory flow rate, inspiratory pause prior to expiration, the lung volume at the time the bolus of medication is administered, and expiratory flow rate, 2) the size, shape and density of the aerosol particles (i.e., the medicinal compound, any carrier, and propellant), and 3) the physiological characteristics of the patient.

Bryon reports that if the deposition fraction is plotted as a function of the airway generation number (See Table I), a bimodal distribution is obtained as illustrated in FIG. 1. The first peak is produced because inertial impact is maximal in the larger airways where airways velocity is highest. This effect is not seen in medium sized airways where velocity is lower and airway size is too large to permit deposition by sedimentation under gravity. The second peak appears in the more distal and smaller airways where velocity is slowest and deposition by sedimentation occurs.

TABLE I

Airway Lengths and Diameters from the Morphological Model of Weibel (Bryon, Respiratory Drug Delivery, CRC Press (1990))

| Generation | Length (cm) | Diameter (cm) |
|---|---|---|
| 0 | 12.000 | 1.800 |
| 1 | 4.760 | 1.220 |
| 2 | 1.900 | 0.830 |
| 3 | 0.760 | 0.560 |
| 4 | 1.270 | 0.450 |
| 5 | 1.070 | 0.350 |
| 6 | 0.900 | 0.280 |
| 7 | 0.760 | 0.230 |
| 8 | 0.640 | 0.186 |
| 9 | 0.540 | 0.154 |
| 10 | 0.460 | 0.130 |
| 11 | 0.390 | 0.109 |
| 12 | 0.330 | 0.095 |
| 13 | 0.270 | 0.082 |
| 14 | 0.230 | 0.074 |
| 15 | 0.200 | 0.066 |
| 16 | 1.165 | 0.060 |
| 17 | 0.141 | 0.054 |
| 18 | 0.117 | 0.050 |
| 19 | 0.099 | 0.047 |
| 20 | 0.083 | 0.045 |
| 21 | 0.070 | 0.043 |
| 22 | 0.059 | 0.041 |
| 23 | 0.050 | 0.041 |

The Bryon and Newman studies also suggest that the modal distribution pattern, and thus the relative location of deposited medication, can be modified by changing those parameters.

The Newman references refer to measuring inspired air with a pneumotachograph to obtain a flow rate signal, which is integrated by a computer to determine lung capacity. A determined lung capacity, as a percent of vital capacity, is used as a threshold to actuate a solenoid to depress the canister of a metered dose inhaler on the inspiration of the predetermined lung volume.

A problem with existing metered dose inhalers, whether or not breath actuated, is that they are factory preset for a given particle size distribution and that distribution cannot be varied. Thus, those devices are not capable of selecting a maximum desired respirable fraction of the aerosol mist that is suitable for a desired location of delivery of the medication. Further, metered dose devices, and in particular breath actuated devices, cannot deliver a metered dose having a selectable respirable fraction in response to an identified point in the patient's inspiratory flow to provide for selective deposition of the medication in selected areas of the lungs.

Devices for controlling particle size of an aerosol are known. U.S. Pat. No. 4,790,305 refers to controlling the particle size of a metered dose of aerosol for delivery to the walls of small bronchi and bronchioles by using a first container into which the medication is delivered prior to inspiration by the patient and a second collapsible container which contains a fixed volume of air to be inspired immediately prior to inspiration of the metered dose of medication, and flow control orifices to control the flow rate. U.S. Pat. No. 4,926,852 refers to metering a dose of medication into a flow-through chamber that has orifices to limit the flow rate to control particle size. U.S. Pat. No. 4,677,975 refers to a nebulizer device that uses baffles to remove from an aerosol particles above a selected size which particles may be returned to the nebulizer for reuse. U.S. Pat. No. 3,658,059 refers to a baffle that changes the size of an aperture in the passage of the suspension being inhaled to select the quantity and size of suspended particles delivered. A problem with these devices is that they process the aerosol after it is generated and thus are inefficient and wasteful.

It is well known that pulmonary functions, such as forced expiratory volume in one second, forced vital capacity, and peak expiratory flow rate, can be measured based on measured flow rates and used both to diagnose the existence of medical conditions, and to ascertain the efficacy of a drug therapy program. See for example, U.S. Pat. Nos. 3,991,304 and 4,852,582 and the Newman references discussed above. Heretofore, these tests have been performed using available spirometers. U.S. Pat. No. 4,852,582 also refers to using a peak flow rate meter to measure changes in peak flow rate before and after administration of a bronchodilator. The results of such tests before and after administration of several different medications are used to evaluate the efficacy of the medications,. which are then used and compared to various laboratory standard or predetermined data to make a diagnosis and prescription for treatment of the patient's condition.

A problem with the foregoing pulmonary function test devices is that they are complicated for most patients to perform. Another problem is that the test data must be examined and interpreted by a trained medical practitioner to be meaningful. Another problem is that they do not provide adequately for altering the dosage of the medication administered in a single patient during the course of therapy, or from patient to patient, using the same delivery device for generating an aerosol of the same or different medications.

SUMMARY OF THE INVENTION

It is, therefore, an object of this invention to provide improved apparatus, systems, and methods for delivering aerosol compounds for inspiration by a patient.

It is another object of this invention to provide improved apparatus, systems, and methods for delivering for inspiration an aerosol having a particle size distribution favorable for selective deposition into desired locations in a patient's pulmonary system. It is another object to release a controlled amount of aerosol in one or more pulses having a selected pulse size, shape, and frequency and number of pulses to produce a selected particle size distribution. It is another object to provide a variably actuated valve mechanism having an open state and a closed state for controlling the medication pulse size, shape, and frequency, to produce a pulse train having a selected particle size distribution at a selected point or a series of selected points in the patient's inspiratory flow and, further, to produce a pulse train so that the particle size distribution delivered at different points in the flow may be different.

It is another object of the invention to deliver aerosolized compounds in response to a measure of a patient's breathing pattern during inspiration. It is another object to select the optimal point or points for release of one or more pulses of medication based on an analysis of the patient's inspiratory flow in a first detected flow and to release the medication on the occurrence of the determined point or points during a subsequently detected inspiratory breath.

It is another object to select the location of deposition of the medication in the patient's airway by selecting the optimal point or points in the inspiratory flow to achieve such deposition. It is another object to deposit selectively the medication based on a selected optimal flow point and a selected pulse train to obtain a desired respirable fraction for such deposition. It is another object to prompt the patient to hold his or her breath for an optimal period of time at the end of inspiration to optimize delivery of the aerosolized compound being administered.

It is another object of the invention to release automatically a controlled amount of medication when the patient's detected inspiratory flow exceeds a preselected or default delivery threshold, and, if the first detected flow does not exceed (or satisfy) the default delivery threshold, to determine a new delivery threshold based on a detected flow maxima parameter of the previously detected inspiratory flow not exceeding the prior delivery threshold and to release a controlled amount of medication when a subsequently detected flow exceeds the new determined delivery threshold. The determined threshold is thus recursively determined for each detected inspiratory flow not exceeding the previously established delivery threshold, whether that threshold is the preselected default triggering threshold or a subsequently determined threshold.

It is another object of this invention to provide improved apparatus, systems, and methods for delivering aerosolized compounds for inspiration by a patient by incorporating a measure of a patient's pulmonary function to provide for varying the dosage or controlled amount of the aerosolized compound delivered for inspiration by the patient in response to detected changes in the patient's pulmonary function during a course of therapy directed to improving pulmonary function.

It is another object to provide improved apparatus, systems, and methods for delivering aerosol compounds for inspiration by a patient by incorporating a measure of a patient's pulmonary function and an acuity display of that function to the patient, for example, to provide for alerting the patient whether the patient's determined function indicates whether the patient should continue the inhalation drug therapy program or seek immediate medical attention.

It is another object of the present invention to provide a programmable, durable variable dose inhaler whereby the medication being administered can be selected and the inhaler can be programmed to provide for efficacious delivery of the selected medication to a given patient. It is another object to provide such a device with a library of information regarding medications to be administered and their respective administration protocols. It is another object to provide an improved inhaler with audible, visual or audiovisual feedback for prompting the patient to obtain a suitable breathing pattern for delivering a selected medication at an appropriate time based on the patient's detected inspiratory flow and, optionally, for measuring a pulmonary function. It is another object to provide feedback for prompting the patient's breathing pattern in response to previously measured pulmonary or flow parameters for automatic administration of the selected medication. It is another object to provide a visual display of the adequacy of a dosage delivered and other parameters regarding the course of therapy, such as time of next dose to be administered. It is another object to provide the medical examiner with a history log of drug administration and points of drug delivery for evaluation.

A further object of the present invention is to provide a hand held microprocessor controlled inhaler device for use in outpatient aerosol drug therapy that is capable of autonomously modifying the initial therapy program based on detected progressive changes in the patient's breath flow and corresponding pulmonary functions. It is another object to provide for communications between the device and a remote station for remote reprogramming of the microprocessor controlled device for external modification of the therapy or for transmitting historical log data for evaluation.

It is another object to provide a disposable mouthpiece containing a nozzle for dispensing medication and a flow rate sensor located in the flow path to detect flow so that it does not interfere with generation of an aerosol for inspiration by a patient.

The present invention increases the effectiveness and utility of devices for delivering aerosolized medications and overcomes the problems of the prior known devices. Broadly, the invention concerns methods and apparatus for achieving the above objectives based on detecting the patient's inspiratory flow and releasing one or more pulses of an aerosol medication respectively at one or more identified points in the detected flow to provide an efficacious delivery of a selected amount of medication.

The following terms are used in describing the present invention. The term "delivery point" refers to a point in the detected inspiratory flow at which an amount of aerosol is to be delivered. The term "amount of aerosol" refers to the amount released in response to the occurrence of a delivery point. The amount may be either a single pulse, or a preselected number of pulses, e.g., four pulses having the same shape and frequency. The term "delivery schedule" refers to one or more delivery points in the detected inspiratory flow such that a full dosage of aerosol is delivered in accordance with the delivery schedule. Thus, a delivery schedule that includes only one delivery point will deliver an amount of aerosol in response to the occurrence of that point in the detected inspiratory flow that corresponds to a full dosage, and a delivery schedule that includes more than one delivery point will deliver an amount of aerosol in response to the occurrence of each point in the delivery schedule in the detected inspiratory flow such that the sum of the amounts total the full dosage. The term "delivery threshold" refers to the first delivery point in the delivery schedule such that if a detected inspiratory flow satisfies the delivery threshold, the event is considered to be a successful delivery of aerosol, notwithstanding that for delivery schedules having more than one delivery point, subsequent delivery points in the delivery schedule may not be satisfied such that a full dosage is not delivered. The term "flow" refers to one of a flow rate in volume per time, a flow volume (which may be calculated from the time integral of the determined flow rate), and a combination of flow rate and flow volume.

One aspect of the invention concerns an oral drug delivery device that delivers each dosage as a sequence of pulses selected to increase the effective respirable fraction of medication delivered compared to a conventional metered dose inhaler device. More particularly, each pulse is provided with a selected pulse width, shape, and frequency that will maximize the respirable fraction of the aerosolized compound being delivered. This pulse selection also will allow manipulation of the cumulative particle size distribution so as to enhance delivery of the aerosolized compound to desired loci in the airway.

One preferred embodiment of this aspect of the invention is directed toward an apparatus for controlling the particle size distribution to maximize the respirable fraction of an aerosol. One such device includes:

(a) a source of aerosol generating material;
(b) a valve, associated with the source, having a first state for releasing an amount of aerosol generating material and a second state for not releasing an amount of aerosol generating material;
(c) means for selecting the relative time the valve is in the first state and the second state to maximize respirable fraction of an aerosol pulse, the valve being in the first state for a time selected from between about 10 to about 1000 msecs; and
(d) means for cycling the valve between states in response to the selected relative time to release an amount of aerosol having the maximized respirable fraction, wherein the valve is cycled at a rate at or below 100 cycles per second.

Another preferred embodiment of this aspect of the invention concerns a method for controlling the respirable fraction of an aerosol in an aerosol drug delivery device having a source of aerosol generating material and a valve having a first state for releasing an amount of aerosol generating material and a second state for not releasing an amount of aerosol generating material. One such method includes:

(a) selecting the relative time the valve is in the first state and the second state to select the maximum respirable fraction of an aerosol pulse, the valve being in the first state for a time selected from between about 10 to about 1000 msecs; and
(b) cycling the valve from the second state to the first state to the second state in response to the selected relative time to release an amount of aerosol having the maximized respirable fraction, the cycling occurring at a rate at or below 100 cycles per second.

In varying embodiments of the apparatus or method, the valve may be opened in the first state for a time in the range of from 10 to about 1000 msecs, otherwise being in the second state for the duration of the cycle, to produce a mist having a cumulative particle size distribution selectively favoring small or large particles. The relative time the valve is in the first state and the second state may be selected so that the valve is operated asynchronously or synchronously to produce one or more pulses such that each full dosage of aerosol includes one pulse or more than one pulse of non-uniform or uniform pulse widths, shapes, and intervals between pulses. Preferably, the valve is cycled in response to a detected inspiratory flow satisfying a provided delivery schedule. Further, the pulses may be provided with selected particle size distributions that vary from pulse to pulse whether in response to the same or different delivery points.

In a preferred embodiment, the valve and the operating valve means are an electromechanically controlled valve actuator, such as an integral solenoid and valve, for metering the contents of a pressurized canister to provide an aerosol pulse train having, for example, synchronous pulses of uniform size, asynchronous pulses of uniform size, synchronous pulses of non-uniform size, asynchronous pulses of non-uniform size, and combinations thereof. The integral solenoid and valve device is preferably interposed in a flow channel from the source of aerosol generating material to a nozzle that produces the aerosol. Preferably, a series of four pulses having a duty cycle of from 8 to 15% are used to deliver an amount of aerosol in response to each delivery point in a delivery schedule satisfied by the flow. Thus, the delivery schedule provided may be selected so that the given respirable fraction of the one or more pulses will be deposited in a desired location in the patient's airways. In this regard, particles intended for deep airway deposition would be delivered in the inspiratory flow earlier, or at lower flow rates and volumes, than particles intended for deposition in peripheral airways.

Another aspect of the present invention concerns an apparatus for selecting the delivery schedule based on the patient's measured inspiratory flow.

In a preferred embodiment, the apparatus has a preprogrammed, default delivery schedule whereby if the patient's first detected inspiratory flow does not satisfy the first delivery point, namely, the delivery threshold, for the default delivery schedule, the apparatus enters a calibration mode. The delivery schedule is further selected for depositing the particles in the desired location for efficacious treatment of the patient. In this embodiment the term "first detected inspiratory flow" refers to the first inspiratory flow detected subsequent to a selected event, i.e., a reset flow event, for example, the apparatus being turned on, the device being reset, a successful delivery of an aerosol, and the expiration of a selected time interval without delivery of an aerosol.

In the calibration mode, the apparatus selects a new delivery schedule of one or more points based on the preceding inspiratory flow (which failed to satisfy its delivery threshold), prompts the patient to take another breath, and, on satisfaction of the newly selected delivery threshold during the subsequently detected inspiratory flow, delivers the aerosol in accordance with the delivery schedule to the extent that any subsequent delivery points are satisfied by the detected inspiratory flow. Thus, the patient receives the selected aerosol medication at the determined optimal delivery point or points for depositing the administered aerosolized compound at preferred loci in the lung.

Once in the calibration mode, if a subsequent breath does not satisfy the newly determined delivery threshold, a recursive routine is used for selecting a new delivery threshold for each successive inspiratory effort that does not satisfy a delivery point threshold which results in successively lowering the delivery threshold by a predetermined amount. The predetermined amount is preferably a sequence of predetermined percentages of the measured flow of the preceding inadequate breath. For delivery schedules having more than one delivery point, typically all delivery points will be lowered by the same percentage as the threshold point. Thus, the device is configured to deliver eventually medication to the patient taking into consideration the patient's inspiratory abilities at the time of dosage administration and the aerosol medication to be delivered. The delivery threshold may be based on an inspiratory flow rate, more particularly, a selected rate prior to the occurrence of the peak inspiratory flow rate, e.g., for a preselected threshold a rate in the range of 20 to 30 liters per minute, an inspiratory flow volume e.g., for a preselected threshold a volume of about 1.0 liter, or, more preferably, a combination of a flow rate and a flow volume. Preferably, once a delivery of aerosol is made, the apparatus will return to its preprogrammed default operating mode and preselected delivery schedule whether or not the full dosage of aerosol has been administered.

One preferred embodiment of this aspect of the invention is directed towards an apparatus for delivering an aerosol from a supply of aerosol generating material for inspiration by a person in response to the detected inspiratory flow of the person. One such apparatus includes:

a valve in communication with the supply of aerosol generating material;

means for operating the valve to release an amount of aerosol generating material to form an aerosol;

means for detecting an inspiratory flow of the person;

means for controlling the valve operating means in response to the detected inspiratory flow comprising:

first means for determining whether each detected inspiratory flow is one of a first flow or a subsequent flow, the first flow corresponding to one of the first attempt to deliver an amount of aerosol and the first attempt to deliver an amount of aerosol following delivery of an amount of aerosol, the subsequent flow corresponding to an inspiratory flow detected subsequent to a preceding detected inspiratory flow not followed by delivery of an amount of aerosol;

means for providing a delivery threshold corresponding to a point in the detected inspiratory flow at which an amount of aerosol is to be delivered, the provided delivery threshold being a preselected delivery threshold in response to the detected inspiratory flow being determined to be a first flow, and a determined delivery threshold in response to the detected inspiratory flow being determined to be a subsequent flow, the providing means including means for calculating the determined delivery threshold based on the preceding detected inspiratory flow; and second means for determining whether or not the detected inspiratory flow satisfies the provided delivery threshold so that the controlling means operates the valve to deliver an amount of aerosol in response to the second determining means determining that the detected inspiratory flow satisfies the provided delivery threshold.

Another aspect of this embodiment of the invention is directed toward a method of delivering an aerosol to a person for inspiration using a device having a supply of aerosol generating material and a valve for releasing an amount of aerosol generating material to form an aerosol, and a means for detecting inspiratory flow of the person. One such method includes the steps of:

(a) detecting an inspiratory flow of the person;

(b) determining whether each detected inspiratory flow is one of a first flow or a subsequent flow, the first flow corresponding to one of the first attempt to deliver an amount of aerosol and the first attempt to deliver an amount of aerosol following delivery of an amount of aerosol, the subsequent flow corresponding to an. inspiratory flow detected subsequent to a preceding detected inspiratory flow not followed by delivery of an amount of aerosol;

(c) selecting a delivery threshold corresponding to a point in the detected inspiratory flow at which an amount of aerosol is to be delivered so that a preselected delivery threshold is selected in response to determining that the detected inspiratory flow is a first flow, and a determined delivery threshold is selected in response to determining that the detected inspiratory flow is a subsequent flow; and (d) determining whether or not the detected inspiratory flow satisfies the selected delivery threshold; and (i) in response to the detected inspiratory flow satisfying the selected delivery threshold, operating the valve to release an amount of aerosol generating material to form an aerosol; or (ii) in response to determining that the detected inspiratory flow did not satisfy the selected delivery threshold, calculating a new delivery threshold based on the detected inspiratory flow so that the selected delivery threshold for the next detected inspiratory flow determined to be a subsequent flow is the calculated delivery threshold.

In a preferred embodiment of this aspect of the invention, the calculating means and method step for providing the determined delivery threshold determines the delivery threshold based on the detection of an inspiratory flow not satisfying the provided delivery threshold, and can recursively determine new delivery thresholds for each successive detected inspiratory flow that fails to satisfy each provided delivery threshold, notwithstanding that the delivery thresholds are successively lowered. One such calculating means includes:

means for measuring a selected flow parameter of the detected inspiratory flow in response to second determining means determining that the detected inspiratory flow did not satisfy the provided delivery threshold; and means for adjusting the provided delivery threshold in response to the measured flow parameter, thereby providing the determined delivery threshold.

One method includes measuring a selected flow parameter of the detected inspiratory flow in response to determining that the detected inspiratory flow did not satisfy the selected delivery threshold and adjusting the selected delivery threshold in response to the measured flow parameter. The selected flow parameter may be a point corresponding to the detected maxima of flow rate, flow volume, or some combination of flow rate and flow volume, such that the adjustment is a percentage of the detected flow parameter.

Preferably, the delivery threshold further comprises a delivery schedule including the delivery threshold as the first delivery point and one or more additional delivery points in the detected flow following the delivery threshold, such that an amount of aerosol is to be delivered at each delivery point in the schedule. Also, for detected inspiratory flows that are determined to be subsequent flows, adjusting the delivery schedule adjusts every point in the delivery schedule and determining whether or not the detected inspiratory flow satisfies the delivery threshold also determines whether or not each delivery point in the delivery schedule is satisfied so that an amount of aerosol is delivered for each delivery point in the delivery schedule that is satisfied by the detected inspiratory flow.

In an alternate embodiment of this aspect of the invention, concerning selecting the delivery schedule based on the person's measured inspiratory flow, the apparatus is configured to operate in a mode whereby a first inspiratory flow is detected, a delivery schedule corresponding to the optimal delivery threshold (and optionally additional delivery points) for the administration of the selected aerosol medication is determined based on a measure of the detected inspiratory flow parameters, and a subsequently detected inspiratory flow is detected and compared to the delivery schedule whereby an amount of aerosol will be delivered in accordance with the delivery schedule upon satisfaction of each delivery point in the determined delivery schedule by the subsequently detected inspiratory flow.

One such apparatus includes:

(a) a reservoir containing an aerosol generating material;

(b) valve means for releasing an amount of the aerosol generating material from the reservoir, thereby to form an aerosol;

(c) means for detecting an inspiratory flow of the person including a first inspiratory flow and a second inspiratory flow occurring subsequent to the first inspiratory flow;

(d) first means for evaluating the first detected inspiratory flow to identify an appropriate delivery threshold for the delivery of an aerosol;

(e) second means for evaluating the second detected inspiratory flow and determining whether the second detected flow satisfies the determined delivery threshold; and (f) means for actuating the valve means in response to the second detected inspiratory flow satisfying the delivery threshold, thereby to deliver an amount of aerosol during the second detected inspiratory flow.

Another aspect of this alternate embodiment of the invention is directed to a method of administering a controlled amount of medication using a device having a supply of aerosol generating material and a valve for releasing an amount of aerosol generating material to form an aerosol and a means for detecting an inspiratory flow of a person. One such method includes the steps of:

(a) detecting a first inspiratory flow of the person;

(b) determining a delivery threshold for the delivery of an amount of aerosol based on the first detected inspiratory flow;

(c) detecting a second inspiratory flow of the person;

(d) determining whether or not the detected second inspiratory flow satisfies the determined delivery threshold; and (e) operating the valve to deliver the amount of aerosol in response to determining that the second inspiratory flow satisfies the determined delivery threshold.

Preferably, in the apparatus and methods of this alternate embodiment, for each second inspiratory flow that does not satisfy a determined delivery threshold, the second inspiratory flow is treated as the first inspiratory flow such that the first determining means determines a new delivery threshold based on the evaluation of that detected inspiratory flow. Another inspiratory flow is then detected (the third) and treated as the second detected inspiratory flow. Thus, the second determining means evaluates the latter flow and determines whether it satisfies the determined delivery threshold based on the preceding flow. The apparatus will continue to determine a new delivery threshold based on a selected detected inspiratory flow, which threshold is used for a following detected inspiratory flow. In this manner, the apparatus will eventually deliver an amount of aerosol medication to the person, even in the event of a degrading inspiratory flow effort. In other respects, this alternate embodiment is similar in operation to the previously described embodiment.

In either embodiment the dosage of aerosol medication may be adjusted over time based on measured changes in the patient's pulmonary functions and, further, each dosage is released based on a delivery schedule, either determined, preprogrammed or recursively determined, so that the administration of aerosol medication occurs automatically in accordance with a desirable delivery schedule in the patient's detected inspiratory flow and with a particle size distribution to maximize the efficacy of the medication.

In either embodiment of this aspect of the invention, the means for detecting the inspiratory flow is preferably a tube defining an inspiratory flow path having a mouth end and an open end and a flow transducer disposed in the flow path. The flow transducer may be selected from among a flow resistive device which generates a pressure drop across the device (referred to as a differential pressure transducer) and an associated means for converting the measured differential pressure into an inspiratory flow rate, e.g., a pneumotach, a hot wire anemometer and means for converting the measured temperature changes into an inspiratory flow rate, and similar devices for providing a flow rate signal. Preferably, the inspiratory flow path includes a means for providing a laminar flow through the inspiratory flow path so that the flow transducer detects the differential pressure across a laminar air flow. The laminar flow provides a flow and a flow path having linear characteristics for converting the differential pressures to flow rate. In embodiments not having a laminar flow means or using transducers and/or inspiratory flow paths not having such linear flow characteristics, such as venturi ports or a single resistive flow screen, the flow path may be encoded by an array of predetermined calibration constants such that nonlinear characteristics of the differential pressures detected across the flow resistive device may be converted by use of the calibration constant array for the range of pressures detected to flow rates, directly or indirectly. Preferably, a differential pressure transducer for use in the present invention will have a differential pressure sensitivity in the range of ±25.4 cm of water corresponding to a flow rate of from about 0 to about 800 liters per minute.

Another aspect of the invention concerns methods and apparatus for monitoring the patient's breath flow patterns during the course of an aerosolized medication inspiration therapy program and determining the patient's pulmonary function based on detected flow. In one embodiment, a display device is provided for displaying the patient's determined pulmonary function. The display device may be used to indicate the patient's instantaneous condition when an instantaneous pulmonary function is measured, to indicate relative changes in condition when a subsequent measure of the pulmonary function is compared to a prior measure or historical average of the measures (e.g. a weighted average) of that pulmonary function, or both. Importantly, this display will indicate to the patient when measured functions indicate that the patient should seek medical attention. Thus, the present invention is believed to overcome the problem of patients not knowing whether their medical condition is better, worse or unchanged, or is being adequately treated during the course of medication.

In another embodiment, the relative changes in measured pulmonary function, whether the change is determined from one administration of medication to the next, or from a baseline measured pulmonary function (or a weighted average historical record) to the next administration of medication, in addition to displaying the condition, also may be used to adjust the dosage of medication based on the determined changes in the determined function. Thus, this aspect of the present invention provides for optimizing the effectiveness of the medication within the limits of preselected parameters, considering such things as maximum allowable dosages for the given patient and the frequency of medication.

One embodiment of this aspect of the invention is directed towards an apparatus and method for measuring the patient's pulmonary function and displaying a visual acuity of the measured function to the patient. One such apparatus includes

- means for detecting a breath parameter of the person selected from among one or more of inspiratory flow and expiratory flow;
- means for determining a pulmonary function of the person based on a measure of at least one of the detected breath parameters;
- a first visual indicator corresponding to a first range of pulmonary conditions for the determined pulmonary function; and
- a second visual indicator corresponding to a second range of pulmonary conditions for the determined pulmonary function, the first and second ranges being contiguous;
- means for evaluating the determined pulmonary function and illuminating the one of the first and second visual indicators whose corresponding range includes the determined pulmonary function.

More than one visual indicator may be used, more preferably three visual indicators corresponding to three contiguous ranges of conditions, respectively, nominal condition, marginal condition, and unacceptable condition.

In a preferred embodiment, the apparatus of this aspect of the invention may be configured to acquire a second measure of pulmonary function, compare that measure to a prior measure, and display trend data to the patient, thereby to indicate whether the person's medical condition is improving, degrading, or remaining about the same. One such apparatus includes:

- means for comparing a first determined pulmonary function to a second determined pulmonary function and indicating whether or not the patient's determined pulmonary function has changed from the first to the second determinations, the first determined pulmonary function being based on a first detected breath parameter and the second determined pulmonary function beign based on a second detected breath parameter subsequent to the first detected breath parameter; and
- means for displaying whether the detected pulmonary function has improved on a first visual indicator, remained nominally the same on a second visual indicator, and degenerated on a third visual indicator in response to the indicated change in the first and second determined pulmonary functions.

One method of this aspect of the invention includes the steps of:

(a) detecting a breath parameter of the person selected from among one or more of an inspiratory flow and an expiratory flow;

(b) determining a pulmonary function of the person based on a measure of at least one of the detected breath parameters;

(c) selecting a first range of pulmonary conditions for the determined pulmonary function and a second range of pulmonary conditions for the determined pulmonary functions, the first and second ranges being contiguous;

(d) providing a first visual indicator corresponding to the first selected range and providing a second visual indicator corresponding to the second selected range;

(e) evaluating the determined pulmonary function with respect to the first and second selected ranges and identifying which range includes the determined pulmonary function; and (f) illuminating the visual indicator corresponding to the identified selected range including the determined pulmonary function.

Preferably, the method includes providing more than two contiguous ranges of pulmonary conditions and more than two corresponding visual indicators for each selected range so that, for example, the measured pulmonary function can be compared to ranges of nominal, marginal, and unacceptable ranges of pulmonary conditions, and the visual indicator corresponding to the selected range including measured pulmonary function can be illuminated.

In an alternate embodiment of the above method, the method includes acquiring a second breath parameter subsequent to the previously measured pulmonary function and measuring a second pulmonary function, comparing the second measured pulmonary function to the first measured pulmonary function, indicating whether or not the patient's determined pulmonary function has changed from the first to the second determinations, providing a first, second, and third visual indicators, and displaying whether the second measured pulmonary function has improved on the first visual indicator, remained nominally the same on the second visual indicator, and degenerated on the third visual indicator, relative to the previously measured pulmonary function.

Another preferred embodiment of this aspect of the invention is directed to an apparatus for selecting the dose of aerosol medication for inspiration by a patient in response to detected changes in pulmonary function. One such apparatus comprises:

(a) a reservoir containing an aerosol generating material including medication;

(b) means for detecting a patient's breath flow;

(c) means for calculating a pulmonary function in response to a detected breath flow;

(d) means for determining a first pulmonary function in response to a first detected breath flow;

(e) means for determining a second pulmonary function corresponding to a second detected breath flow, the second detected breath flow occurring subsequent to the first detected breath flow;

(f) means for comparing the first determined pulmonary function and the second determined pulmonary function to identify relative changes in pulmonary function over time; and (g) means for releasing a controlled amount of medication from the reservoir in response to the first and second determined pulmonary functions so that the controlled amount is adjusted for identified relative changes in the first and second determined pulmonary functions.

Preferably, the apparatus and methods further provide means for identifying the appropriate delivery schedule in a detected inspiratory flow for releasing the dosage of aerosol medication, and means for delivering a dosage of aerosol adjusted in response to identified relative changes in the first and second pulmonary functions, a subsequently detected inspiratory flow satisfying the delivery schedule. Means for recursively adjusting the delivery schedule may be provided when a detected inspiratory flow does not satisfy a delivery threshold.

This aspect of the invention also is directed to a method for adjusting the controlled amount of medication in response to detected changes in pulmonary function over time. One such method includes the steps of:

(a) detecting a patient's first breath flow;

(b) determining a first pulmonary function in response to the detected first breath flow;

(c) detecting a patient's second breath flow subsequent to the first breath flow;

(e) determining a second pulmonary function in response to the detected second breath flow;

(f) comparing the first and second determined pulmonary functions and identifying relative changes between the first and second determined pulmonary functions; and (g) adjusting the amount of aerosol to be delivered in response to the identified changes in pulmonary function.

It should be understood that, in the context of comparing two measured pulmonary functions, the term first breath flow or first detected pulmonary function may be one of the previously acquired measurement, a baseline measurement made at the beginning of the medication therapy, and a changing weighted average of previously acquired measurements, whereby the weights may be selected to favor more recently acquired or less recently acquired measurements. Thus, the latter acquired measurement may be compared to such a first measurement for indicating short term relative changes, absolute changes from a baseline, or more long term relative changes.

Another aspect of the invention concerns providing the device with a memory for containing a library of administration protocols or parameters for different medications and their applications and a means for identifying the medicinal contents of the canister, and optionally, the application for such medication. Preferably, the canister is provided with a code identifying the medication, and the device receptacle for the canister includes means for reading the canister code when the canister is inserted in the receptacle. The information is then used for reprogramming the device for delivering the medication identified, for example, during a power-up or reset operation. Suitable canister codes include product labeling such as a bar code, a factory set resistor value, or a read only memory device, e.g., a byte of digital data, such that the means for reading the code can read the bar code, resistor value or memory byte contents, which information is then used to identify the medication by, for example, reference to a look-up table or preprogrammed software control subroutines.

One embodiment of this aspect of the invention is directed toward a system for releasing an aerosol for inspiration by a patient comprising:

(a) a reservoir of a selected medication;

(b) means for identifying the selected medication, said means being associated with the reservoir;

(c) valve means for releasing the selected medication from the reservoir, thereby to form an aerosol;

(d) means for actuating the valve means to deliver a controlled amount of the selected medication as an aerosol; and (e) means for controlling the actuating means comprising:

(i) means responsive to the identifying means for obtaining the identity of the selected medication, and (ii) means for containing the operating parameters for administering a controlled amount of the selected medication, whereby the controlling means controls the actuating means to release a controlled amount of the selected medication in accordance with the operating parameters associated with the identified selected medication.

In one preferred embodiment the containing means includes a library containing the operating parameters for each of a plurality of medications so that identification of the selected medication in the reservoir provides for the controlling means, preferably a microprocessor device, selecting from the library the operating parameters corresponding to the identified selected medication for use in controlling the release of the selected medication for inspiration by the patient. In an alternate embodiment, the apparatus also includes a means for receiving operating parameters for identified medications not within the containing means, whether or not the containing means includes a library of medications, and for providing the received operating parameters to the controlling means. Such input may be provided externally by a medical practitioner or by memory contained in a read only memory device associated with the canister.

Another embodiment of this aspect of the invention is directed towards a method for releasing an aerosol for inspiration by a patient in a device including a reservoir of aerosol generating material including a medication, a valve for releasing medication from the reservoir, and a means for controlling the valve for delivering an amount of the aerosol medication for inspiration by the patient. One such method includes the steps of:

(a) providing the reservoir with an associated code corresponding to the medication in the reservoir;

(b) providing the controlling means with the operating parameters for releasing a dosage of the medication;

(c) identifying the code associated with the reservoir;

(d) selecting the operating parameters for the medication of the identified codes from the operating means; and (e) operating the valve to deliver the dosage of aerosol medication in accordance with the selected operating parameters for the medication.

In a preferred embodiment, the method step (b) includes providing a library of operating parameters for a plurality of medications and step (d) includes selecting from the library the operating parameters corresponding to the medication identified from the code associated with the reservoir. In another preferred embodiment, step (c) includes reading the code from the reservoir when the reservoir is inserted into a suitable receptacle in the device.

Preferably, the apparatus releases one or more pulses at the appropriate points in the patient's inspiratory flow to optimize the deposition of the administered aerosolized medication within the desired loci within the lung. The apparatus also may adjust the controlled amount of medication delivered and/or the particle size in each dosage of medication delivered in response to detected changes in the patient's pulmonary function.

Another aspect of the invention concerns a portable, hand held device for use in delivering aerosolized medications to a patient. One such apparatus includes:

a tube forming a flow path having a mouth end and an open end;

a nozzle disposed in the tube directed toward the mouth end;

a flow transducer disposed in the inspiratory flow path for detecting the patient's breath flow including an inspiratory flow;

a receptacle for receiving a supply of aerosol generating material;

an aerosol flow path extending from the receptacle to the nozzle;

a valve interposed in the aerosol flow path for opening and closing the flow path; and means for actuating the valve to open and close the flow path for delivering an amount of aerosol out the nozzle.

In a preferred embodiment, the device further include, means for detecting the patient's inspiratory flow and operating the actuating means to deliver an amount of aerosol to the patient during the detected inspiratory flow.

In another embodiment, the device also could include means for reading a code associated with a supply of aerosol such that the medication contained in the supply can be identified and the appropriate operating parameters for that medication can be selected for controlling the valve accordingly. Preferably, the code reading means is disposed interior to the receptacle so that the code associated with the supply is read as the supply is inserted into the receptacle. Further, means for receiving a supply of power for operating the device may be disposed in the receptacle so that the receiving means can electrically connect to a source of power, e.g., a battery, associated with the supply of medication.

In another embodiment of this aspect of the invention, the valve and actuating means may be an electromechanical device, such as an integrated solenoid and valve. More preferably, the solenoid is operated to deliver the aerosol at a pulse cycle of one or more pulses to provide the aerosol with a selected particle size distribution so as to maximize the respirable fraction of the administered aerosolized compound. Also, the flow transducer is preferably a differential pressure transducer and the means for detecting the patient's inspiratory flow converts the detected differential pressures into flow measurements. In one embodiment, the flow transducer is accompanied by a laminar flow device so that the differential pressures are directly related to measured flow. In an alternate embodiment, the flow transducer does not use a laminar air flow and the detecting means uses a set of calibration constants to convert the detected differential pressures into measured flow. It should be understood, however, that most air flow paths have some degree of non-linearity which can be corrected by use of calibration constants. A filter may be provided between the mouth end of the tube and the flow transducer to prevent particulate matter from interfering with the flow measurement or clogging the flow transducer, particularly differential flow pressure transducers.

In another embodiment of this aspect of the invention, the tube, including the flow path, the flow transducer (and any filter associated therewith), a portion of the aerosol flowpath, and the nozzle may be detachable from the other portions of the device so that it may be replaced after use. In this embodiment, the aerosol flow path may be comprised of two interconnecting channels, one extending from the receptacle to a port proximate to the tube, and the other extending from that port to the nozzle.

BRIEF DESCRIPTION OF THE DRAWINGS

Further features of the invention, its nature and various advantages will be-more apparent from the accompanying drawings and the following detailed description of the invention in which like reference numerals refer to like elements and in which.

DETAILED DESCRIPTION OF THE INVENTION

Figure 1:
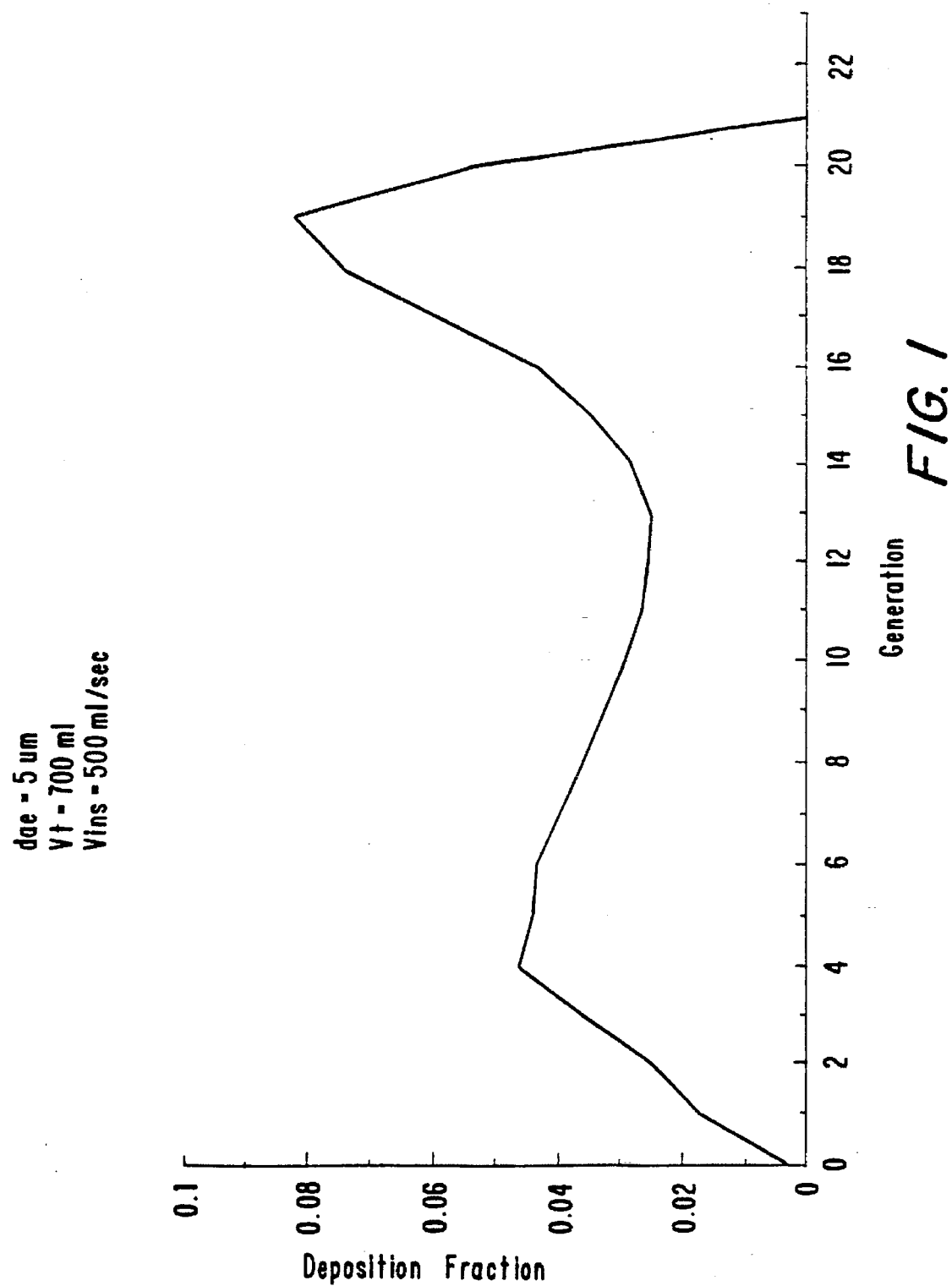
FIG. 1 is a representative plot of the predicted fraction of particles entering the trachea that deposit in each airway generation for fixed particle size and breathing pattern.
Figure 2A:
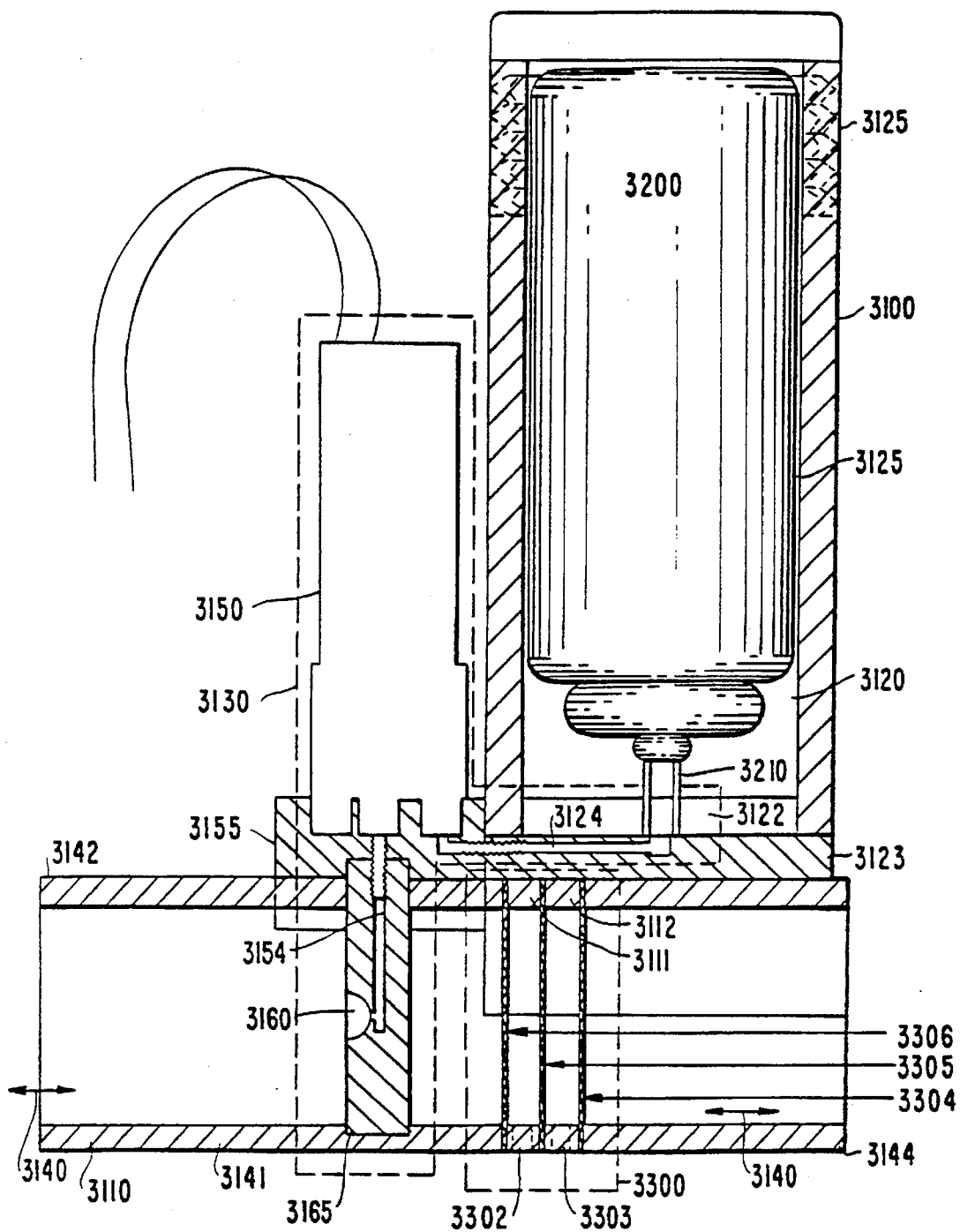
FIG. 2A is a side cross sectional view of an embodiment of the present invention.
Figure 2B:
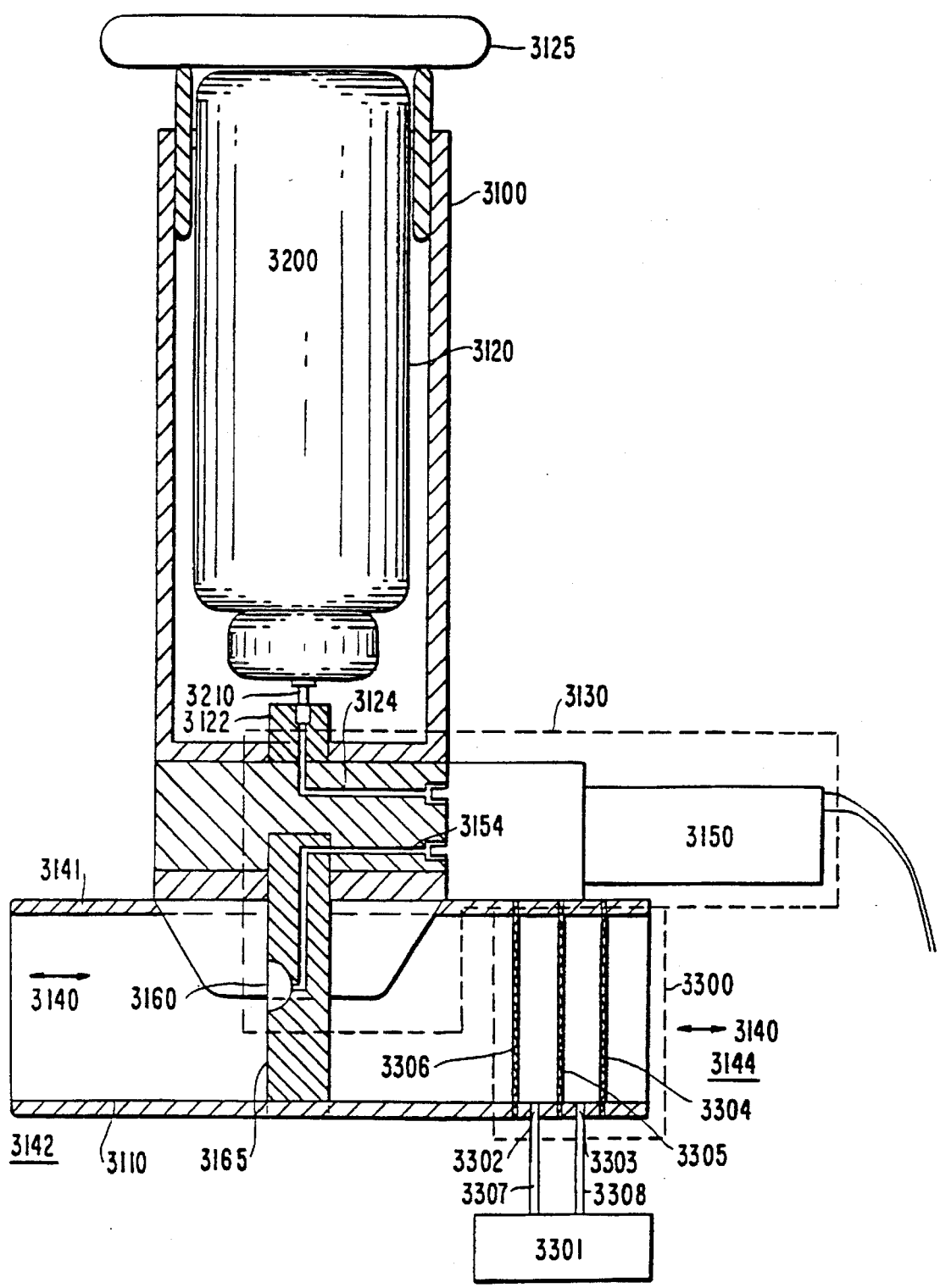
FIG. 2B is side cross sectional view of an embodiment of the present invention.
Figure 3:
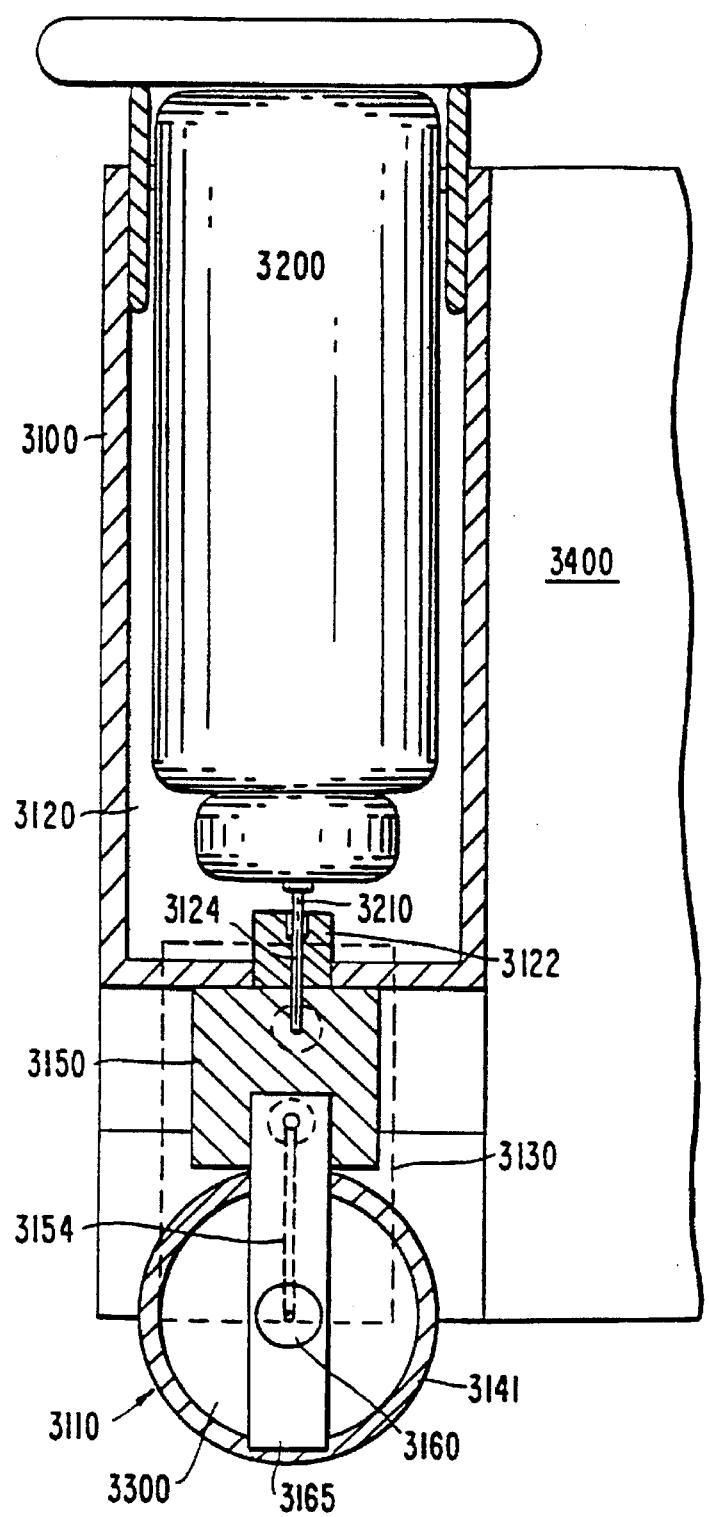
FIG. 3 is a front partial sectional view taken along line 3—3 of FIG. 2B.

Referring to FIGS. 2A, 2B, and 3, one embodiment of the present invention includes base 3100, canister 3200, flow sensor 3300, solenoid valve 3150, aerosol delivery system 3130, mouthpiece 3110, and control circuits 3400 (circuits 3400 not shown in FIG. 2A). Canister 3200 preferably contains a medication under pressure and has a valve 3210 for releasing medication. Base 3100 includes a receptacle 3120 for receiving canister 3200, a valve seat 3122 for receiving canister valve 3210, and means 3125 for retaining canister 3200 in receptacle 3120 as described herein. Means 3125 is preferably a threaded cap that screws into (FIG. 2b) or about (FIG. 2A) the open end of receptacle 3120 so that an inserted canister 3200 is fully seated in receptacle 3120 in a stationary position. In the fully seated position, canister valve 3210 is depressed open and the contents of canister 3200 are thus in communication with aerosol delivery system 3130.

Means 3125 may include alternate structures for locking canister 3200 in the fully seated position, for example, a locking hinged lid or a conventional bayonet mount connection wherein the canister body has one or more protrusions that mesh with one or more receptacles in receptacle 3120 when the canister is fully inserted and rotated in receptacle 3120.

Canister 3200 is preferably a conventional canister containing the medication to be delivered and a suitable propellant or carrier for the medication and having valve 3210 for controlling the release of medication when valve 3210 is depressed and thus opened. Such canisters 3200 are commercially available from a variety of sources and are well known in the art. One such canister is model No. C-128-S available from Prespart Co. and one suitable valve for that canister is a straight valve model no. BK-295, available from BESPAK, King's Lynn, England.

Aerosol delivery system 3130 operates under the control of control circuits 3400 and provides one or more pulses of medication from canister 3200 to airflow path 3140 and mouthpiece 3110 by selective control of solenoid valve 3150. System 3130 includes valve seat 3122, inlet channel 3124, solenoid valve 3150, outlet channel 3154, and aerosol nozzle 3160. Inlet channel 3124 forms a gas communication path between canister 3200 and solenoid valve 3150 for passing the pressurized contents of canister 3200 to valve 3150. Outlet channel 3154 forms a gas communication path from valve 3150 to nozzle 3160, for passing the pressurized contents of canister 3200 to nozzle 3160 to deliver an aerosol into air flow path 3140.

When solenoid valve 3150 is inactive or closed, inlet channel 3124 does not pass gas therethrough. Channel 3124 thus will equilibrate with the contents of canister 3200. Similarly, outlet channel 3154 does not pass gas therethrough and will equilibrate with the atmosphere. When valve 3150 is actuated or open, channels 3124 and 3154 are in open communication and the contents of canister 3200 are released to the atmosphere through nozzle 3160 to form an aerosol. Solenoid valve 3150 thus controls the delivery of the contents of canister 3200 to the patient as described further herein.

Referring to FIG. 2A, channel 3124 is tooled in manifold 3123 and manifold 3155, which respectively interface receptacle 3120 and solenoid 3150, and channel 3154 is TOOIED in manifold 3155 for interfacing solenoid 3150 and nozzle 3160. The use of manifolds provides for removable interconnections for repair, cleaning or replacement of parts of BASE 3100.

Air flow path 3140 is formed of a tube 3141, preferably having a flattened cylindrical cross section, and includes a mouthpiece 3110 at mouth end 3142 and flow sensor 3300 at back end 3144. Interposed between mouth end 3142 and back end 3144 is a projection 3165 which contains nozzle 3160 and is secured to the wall of air flow path 3140. Projection 3165 is provided with a dimension that does not interfere with flow through path 3140 and preferably extends diametrically across flow path 3140 so that nozzle 3160 is directed to release an aerosol into and in longitudinal alignment with air flow path 3140 for inspiration by the patient. Projection 3165 is preferably made of the same material as tube 3141 forming flow path 3140, e.g., an acrylic material, and more preferably is molded as a part of tube 3141. Nozzle 3160 is preferably provided with a configuration that facilitates aerosol generation and dispersion appropriate for the tube dimensions.

Tube 3141 preferably provides mouthpiece 3110 with a cylindrical cross section preferably larger than the aerosol plume delivery into the patient's mouth. Tube 3141 need not have a uniform cross section, but desirably has minimal pressure drop there across (excluding any pressure drop across sensor 3300). Alternate embodiments for the cross section of mouth end 3142 may include circular, oval or flattened oval cross sections or other configurations developed to provide a good seal between the patient's mouth and flow path 3140 so that the patient's inspiratory and expiratory flow passes substantially through tube 3141 along path 3140.

Flow sensor 3300 may be any sensor that provides a measure of flow at a rate of from about 0 to about 800 liters per minute. Flow sensor 3300 is located in flow path 3140 where it will not interfere with the delivery of aerosol to the patient, yet is able to measure both inspiratory and expiratory flow. In the preferred embodiment, sensor 3300 includes a flow resistor device that provides laminar air flow across sensor 3300, comprising three screens, 3304, 3305, and 3306, and two pressure ports 3302 and 3303. Associated with sensor 3300 are a conventional pressure differential transducer 3301 and circuits for obtaining a flow measurement (see FIGS. 4 and 6, transducer 3301 is illustrated in FIG. 2B for reference). Screens 3304, 3305 and 3306 are oriented perpendicular to air flow path 3140, spaced apart ¼" in parallel and secured to the inside of tube 3141 so that they extend across the cross sectional area of path 3140. Referring to FIG. 2A, tube 3141 is assembled by gluing together, in axial alignment, mouth tube section 3110, screen 3306, tube section 3111, screen 3305, tube section 3112, screen 3304, and end tube section 3144 whereby the lengths of tube sections 3111 and 3112 define the spacing between the screens.

Screen 3305 is a resistor screen across which a differential pressure is measured at ports 3302 and 3303 to obtain a measure of the flow rate. Screens 3304 and 3306 provide a laminar air flow across screen 3305 and through sensor 3300 which is suitable for obtaining air flow measurements. Port 3302 is located between screens 3306 and 3305, and port 3303 is located between screens 3305 and 3304. Referring to FIG. 2B, ports 3302 and 3303 are respectively connected to transducer 3301 by conventional flexible tubes 3307 and 3308 having about a 3 mm inner diameter and provide the differential pressures developed across resistive screen 3305 to transducer 3301. The differential pressures, preferably in the range of plus or minus 10 cm of water, are then used to provide a voltage proportional to flow through path 3140, and the sign of the voltage determines the direction of flow. One such preferred differential flow transducer 3301 is model No. NPH-8-2.5DH, commercially available from NOVASENSOR of Fremont, Calif. The flow through pathway 3140 may be sampled at 60 Hz to obtain the flow rate measurements.

Other forms of such a sensor 3300 may be other forms of a pneumotachograph, e.g., a temperature compensated device, or a thermal wire air flow measurement system. A pneumotachograph is a known sensor having a pneumatic resistor interposed in an air flow, such as a resistor screen, that maintains a laminar air flow having a pressure drop across the structure. The pressure drop is measured and can be directly related to air flow rates across the structure by the pneumatic equivalent of Ohm's law. Thus, once the sensor is calibrated, the air flow rate can be accurately determined based on the measured pressure drop for any air flowing across the structure within the operating range of the sensor.

In an alternate embodiment (not shown), a suitable differential pressure flow sensor could include, for example, a venturi device or a flow resistive screen not characterized by laminar flow, provided that the raw differential pressure measurement obtained across such a venturi device or the flow resistor is calibrated to account for the non-linearity of the air flow path so that the calibrated flow data correspond to data from a linear flow path.

In the preferred embodiment, flow path 3140, including mouthpiece 3110, protrusion 3165, and sensor 3300 (optionally not including transducer 3301) may be removable from body 3100 so that it may comprise a disposable part. A conventional detachable connection, not shown, may be provided. Accordingly, means for interconnecting channel 3154 to valve 3150, such as a male-female snap connection, may be incorporated into the design. Use of a disposable airway is desirable because debris will accumulate on the part so that it can be cleaned or a new mouthpiece provided. Similarly, if a filter is provided (not shown), that filter may be separately removable from the part for replacement.

Referring to FIGS. 2, 3, 4, and 5, control electronics 3400 for an embodiment of the present invention are shown. Electronics 3400 include a microprocessor 2000, an external memory subsystem 2100, a decoder circuit 2020, a latch device 2030, a reset circuit 2040, a clock oscillator 2010, a data acquisition subsystem 2200, three LED annunciator subsystems 2300, 2400 and 2500, a solenoid actuator subsystem 2600, an audio speaker subsystem 2700, and a character display subsystem 2800. The discrete components of electronics 3400 are conventional parts having input and output pins which are configured as illustrated in FIGS. 4–11 and described herein, which connections are made in accordance with the instructions provided by the device manufacturers, unless otherwise stated.

Use of CMOS technology for electronics 3400 is preferred because of the low power consumption of such devices. This permits the use of a battery powered, portable, hand-held device for patient use having a size that compares favorably to existing metered dose inhaler devices.

Microprocessor 2000 is provided with suitable software programming that controls the operation of the device. One embodiment of such software is set forth as a software appendix to this specification and is discussed below.

Optionally, electronics 3400 may include a voltage converter and an associated output port for converting the digital information to a voltage format compatible for communicating with another microprocessor device, for example, an RS232 port or a facsimile machine (not shown). Further, as discussed in detail below, electronics 3400 may include means for reading a canister code for identifying the contents of the medication to be administered and selecting the device administration protocol for the identified medication (not shown).

Figure 4:
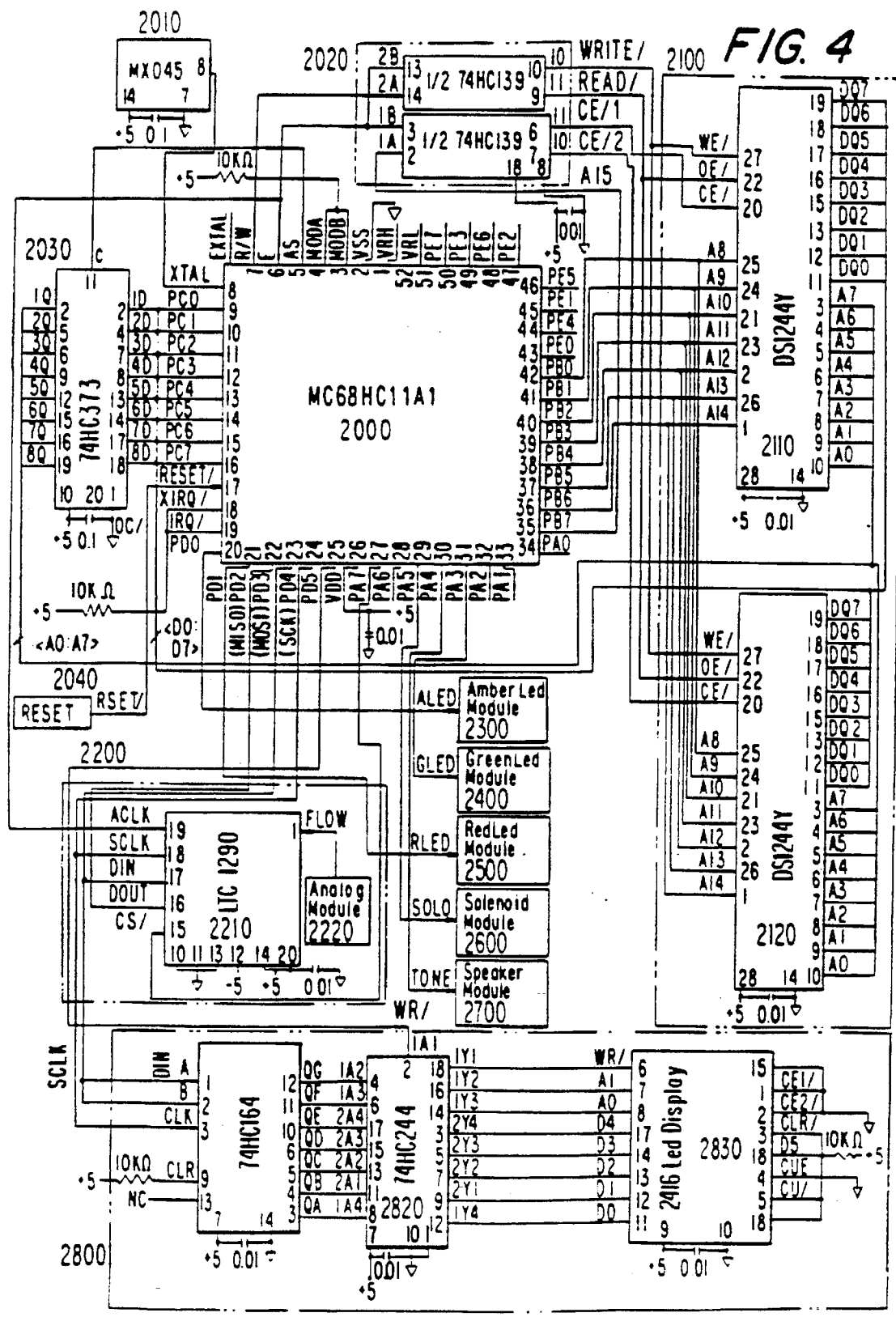
FIG. 4 is a schematic diagram of the digital control circuits of the device of FIG. 2B.

Referring to FIG. 4, microprocessor 2000 may be any software controlled device suitable for operating the data acquisition and determination functions and for controlling the operation of solenoid valve 3150 to release the selected member of pulses of medication at the desired points in the patient's inspiratory flow in accordance with the preferred embodiment of the invention. One suitable device for microprocessor 2000 is model no. MC68HC11A1, available from Motorola, Inc., Microcontroller Division, Austin, Tex., the use of which is described herein.

Microprocessor 2000 is preferably configured to run in an expanded multiplexed mode through connection of lines MODA and MODB at pins 2 and 3 to logic one, a reference voltage Vcc of +5 volt fed across a 10KΩ resistor. Latch device 2030 is preferably an 8 bit device that demultiplexes the address and data information transmitted along port c at pins 9–16 of microprocessor 2000 and allows addressing of the address space of memory subsystem 2100. Latch 2030 is preferably model 74HC373, available from National Semiconductor, Santa Clara, Calif.

Memory subsystem 2100 preferably has a 64K byte address space and includes two 32K byte non-volatile CMOS RAM devices 2110 and 2120, each containing an internal lithium battery. Preferably, RAM devices 2110 and 2120 each contain a non-volatile clock/calendar that is settable and accessible under software control by microprocessor 2000. In the preferred embodiment, only the clock/calendar of device 2110 is used. Non-volatile RAM devices 2110 and 2120 thus provide for maintaining a date and time record of the data acquired and the operation of the device for subsequent review and evaluation by appropriate medical practitioners. This will enable evaluation of the performance of the device for the delivery of medication and the efficacy of the drug therapy program for the patient, even in the event of general power loss of electronic control circuits 3400. The clock/calendar feature also can be used to perform the alarm clock feature to indicate to the patient that a dose is to be administered, for example, by reviewing a list of scheduled dosing times. Appropriate RAM devices 2110 and 2120 are preferably models DS1244Y, available from Dallas Semiconductor, Dallas, Tex.

The 64K byte address space of memory subsystem 2100 may be continuously addressed in the following manner. Signal AS at pin 4 of microprocessor 2000 causes the low 8 bits of a 16 bit address to be latched from port c at pins 9–16 of microprocessor 2000 into pins 2, 4, 7, 8, 13, 14, 17, and 18 of latch 2030. The latching of these address bits into latch 2030 allows 8 bits of data from port c, the high address bits from port b (pins 35–42 of microprocessor 2000) and the low 8 address bits from the output at pins 2, 5, 6, 9, 12, 15, 16, and 19 of latch 2030 to be available simultaneously.

Decoder device 2020 is used to decode the write enable WE/, output enable OE/, and chip enable CE/ control lines at pins 27, 22, and 20 respectively of each of RAMs 2110 and 2120. A suitable decoder device 2020 is model 74HC139, available from National Semiconductor, Santa Clara, Calif. Address line A15 from line PB7 at pin 35 of microprocessor 2000, is input to line 1A at pin 2 of decoder 2020 and is used to determine which 32K byte RAM bank to select for each memory access. Valid WRITE/, READ/, CE/1, and CE/2 signals respectively coming from pins 10, 9, 6, and 7 of decoder 2020 are all active low and are valid only when the signal E from pin 5 of microprocessor 2000 is raised active high. This procedure ensures that memory subsystem 2100 will be accessed only during valid memory references.

Clock 2010 provides a clock input for microprocessor 2000. Preferably, clock 2010 is a CMOS oscillator having a frequency of 8.0 MHz. A suitable device for clock 2010 is model MX045, available from CTS Inc., Japan.

Figure 5:
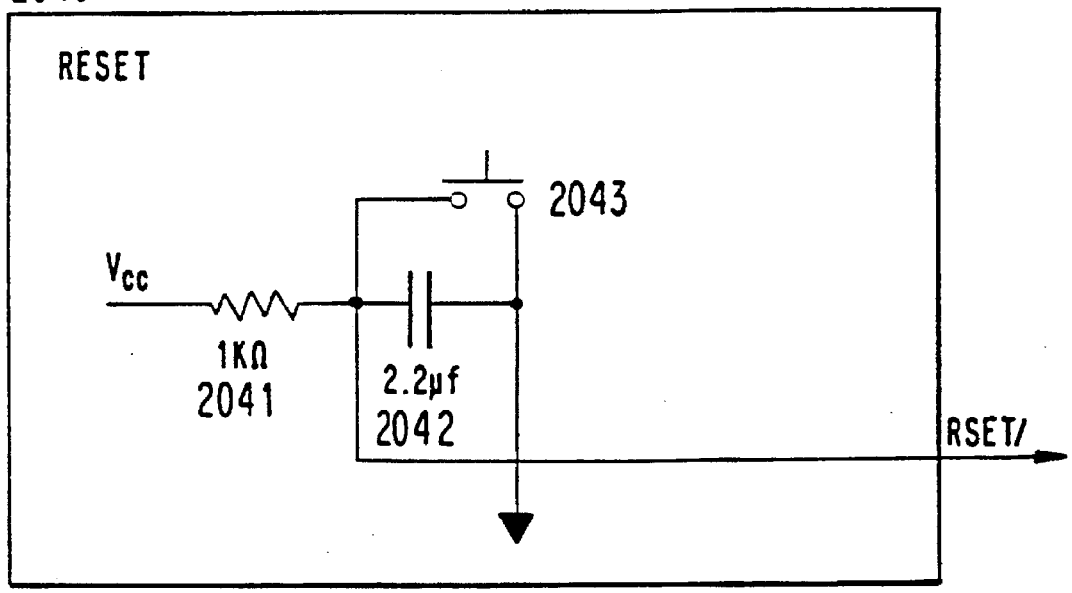
FIG. 5 is a schematic diagram of a reset circuit of FIG. 4.

Referring to FIGS. 4 and 5, reset circuit 2040 provides a power-on reset function. Reset circuit 2040 includes a reference voltage Vcc, resistor 2041, capacitor 2042 and switch 2043. When the system is turned on, a transient pulse from ground to voltage Vcc is generated. Vcc is preferably +5 volts, resistor 2041 is preferably 1KΩ, and capacitor 2042 is preferably 2.2 microfarads. Resistor 2041 thus presents a logic high signal to the non-grounding lead of capacitor 2042 when power is applied to the system. However, the potential across capacitor 2042 does not change instantaneously and a ground potential is presented to the RESET/line at pin 17 of microprocessor 2000 until capacitor 2042 charges. This provides for a reset of microprocessor 2000, its software routines, and the electronic system of the device. A manual reset may be obtained at an arbitrary time by closing switch 2043. This provides for discharging capacitor 2042 to obtain a transient ground pulse for resetting microprocessor 2000.

Referring to FIGS. 4–11, microprocessor 2000 is configured to be connected to and control data acquisition subsystem 2200, LED annunciator modules 2300, 2400, and 2500, solenoid control module 2600, speaker module 2700, and character display subsystem 2800.

Figure 6:
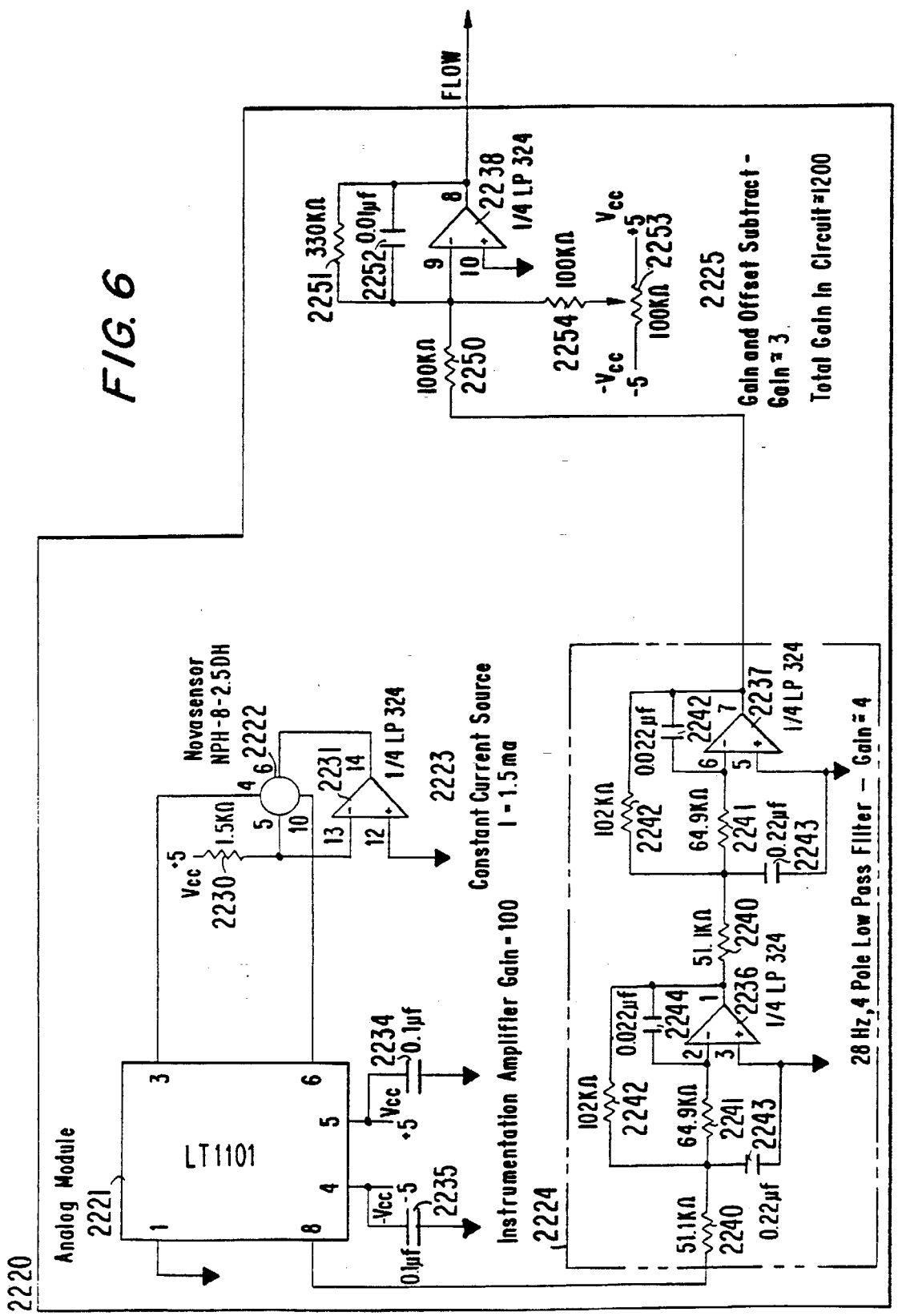
FIG. 6 is a schematic diagram of the analog module of FIG. 4.
Figure 7:
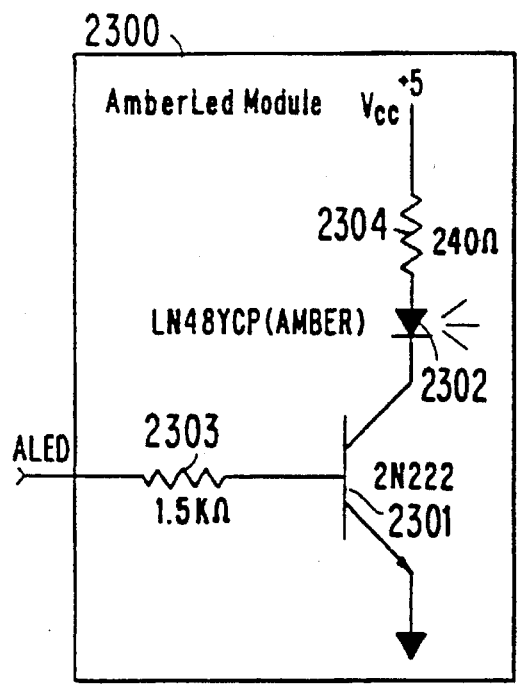
FIG. 7 is a schematic diagram of an LED annunciator module of FIG. 4.
Figure 8:
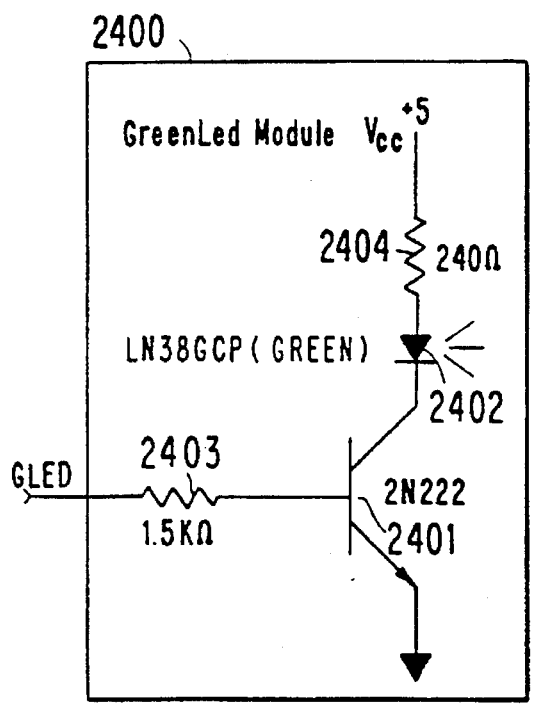
FIG. 8 is a schematic diagram of an LED annunciator module of FIG. 4.
Figure 9:
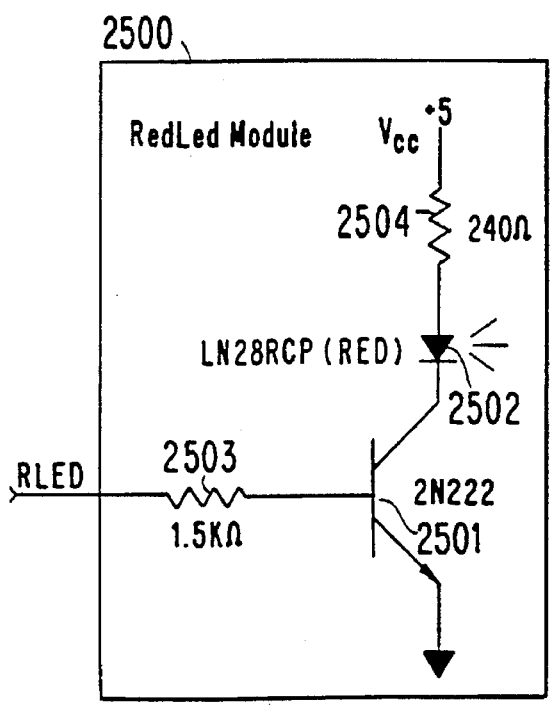
FIG. 9 is a schematic diagram of an LED annunciator module of FIG. 4.

With reference to FIGS. 4 and 6, data acquisition subsystem 2200 includes a 12 bit analog to digital converter (ADC) 2210 and an analog circuit 2220. ADC 2210 is preferably a model LTC1290, available from Linear Technology Corporation, Milpitas, Calif. and is interfaced to microprocessor 2000 via a three wire serial interface and a chip select line. The serial interface includes control lines serial clock SCLK, data in DIN, and data out DOUT, respectively at pins 18, 17, and 16 of ADC 2210. These control lines are connected to lines serial clock SCK, master out slave in MOSI, and master in slave out MISO at pins 24, 23, and 22 of microprocessor 2000.

Lines SCK, MOSI and MISO of microprocessor 2000 are internally associated with the serial peripheral interface (SPI) feature of microprocessor 2000 which is programmed to run as "master" in this embodiment. The SPI allows a stream of bytes of arbitrary length to be simultaneously sent and received by microprocessor 2000. Bytes sent serially to the DIN input of ADC 2210 are interpreted as digitized data points.

Input CS/at pin 15 of ADC 2210 is connected to line A7 at pin 27 of microprocessor 2000 and is manipulated under software control to facilitate communication to and from ADC 2210. A logic low signal on this line causes data to be simultaneously shifted in and out of lines DIN and DOUT, respectively. A logic high signal on this line cause ADC 2210 to ignore data present on line DIN and causes the DOUT line to float.

Analog module 2220 generates a voltage proportional to flow across sensor 3300 as determined by a differential strain gage pressure transducer 2222. Module 2220 includes an instrumentation amplifier 2221, pressure transducer 2222 (corresponding to element 3301 illustrated in FIG. 4), a constant current source 2223, a low pass filter circuit 2224, and a gain and offset circuit 2225.

Transducer 2222 is preferably a wheatstone bridge strain gage pressure transducer capable of producing a signal over a pressure range of plus or minus 10 inches of water. One such transducer device is model NPH-8-02.5DH available from Novasensor Inc., Fremont, Calif. Transducer 2222 is excited by constant current source 2223, an operational amplifier 2231 configured to provide approximately 1.5 ma. Input to transducer 2222 are the pressures communicated through tubes 3307 and 3308 from ports 3302 and 3303 of sensor 3300 which are converted to electrical signals by transducer 2222. The output electrical signals produced at pins 4 and 10 of transducer 2222 are provided to input pins 3 and 6 of instrumentation amplifier 2221. Input at pin 5 of transducer 2222 is a reference voltage Vcc of +5 volts fed across a resistor 2230 having a resistance of 1.5KΩ.

Instrumentation amplifier 2221 is preferably a model LT1101 available from Linear Technology, Fremont, Calif., and is configured with a reference voltage −Vcc of −5 volt input to pin 4, and a reference voltage Vcc of +5 volts input to pin 5, respectively fed across parallel decoupling capacitors 2233 and 2234 each having a capacitance of 0.1 microfarads. Amplifier 2221 provides a gain of about 100.

The outputs at pins 1 and 8 of amplifier 2221 are fed forward to filter 2224. Filter 2224 is configured as a 28 Hz, 4 pole active low pass filter having a gain of about 4. This circuit acts as an anti-aliasing filter prior to the anticipated 60 Hz sampling rate of analog to digital conversion. Filter circuit 2224 includes two operational amplifiers 2236 and 2237 having identical circuit configurations that are connected in series as illustrated in FIG. 6. Resistors 2240 are 51.1KΩ, resistors 2241 are 64.9KΩ. Resistors 2242 are 102KΩ. Capacitors 2243 are 0.22 microfarads and capacitors 2244 are 0.022 microfarads.

The filtered output signal is passed through circuit 2225 to offset adjust the signal for a final gain of about 1200. Circuit 2225 includes amplifier 2238 configured as illustrated in FIG. 6. Resistor 2250 is 100KΩ, resistor 2251 is 330KΩ, capacitor 2252 is 0.01 microfarads, resistor 2254 is 100KΩ, and potentiometer 2253 has a maximum resistance of 100KΩ. Potentiometer 2253 is preferably a conventional multiturn potentiometer that provides for nulling the offset prior to beginning any flow measurement. The function could be provided by a digitally controlled potentiometer under software program control. The four operational amplifiers of circuit 2220 are preferably contained within a single device, part No. LP324, available from National Semiconductor, Santa Clara, Calif.

The differential pressure inputs of transducer 2222 are in communication with airway 3140 through port 3302 and 3303 via tubes 3307 and 3308. Thus, in operation, air flow through sensor 3300 causes a pressure drop across resistor screen 3305 that varies with the flow. Analog module 2220 thus provides an output signal FLOW having a voltage proportional to flow and a sign, plus or minus, that indicates the direction of flow being detected.

Output FLOW of circuit 2220 is fed to pin 1 of ADC 2210 via channel 1 of the internal analog multiplexor. This input is configured under program control to function in a bipolar, singled ended mode.

Referring to FIGS. 4 and 7–9, LED annunciator modules 2300, 2400, and 2500 are similarly configured and each includes respectively one transistor switch 2301, 2401, and 2501 controlling a single light emitting diode 2302, 2402, and 2502, where each of diodes 2302, 2402 and 2502 emit light at a different color of the visible spectrum, more particularly amber, green and red respectively. Appropriate LEDs are part numbers LN48YCP (amber), LN48GCP (green) and LN48RCP (red), each available from Panasonic, Japan.

For each of modules 2300, 2400 and 2500, each switching transistor is driven, via a base current limiting resistor, by the corresponding digital output at each of pins 20, 31, and 21 of microprocessor 2000. When the transistor conducts, current flows through the LED to ground through a collector current limiting resistor. Each of the circuits are respectively configured with transistors 2301, 2401, and 2501 having base resistors 2303, 2403, and 2503 of 1.5KΩ, LEDs 2302, 2402, and 2502 in series with collector resistors 2304, 2404, and 2504 each having 240 Ω in series with reference voltage Vcc of +5 volts, and the transistor emitters tied to ground.

Figure 10:
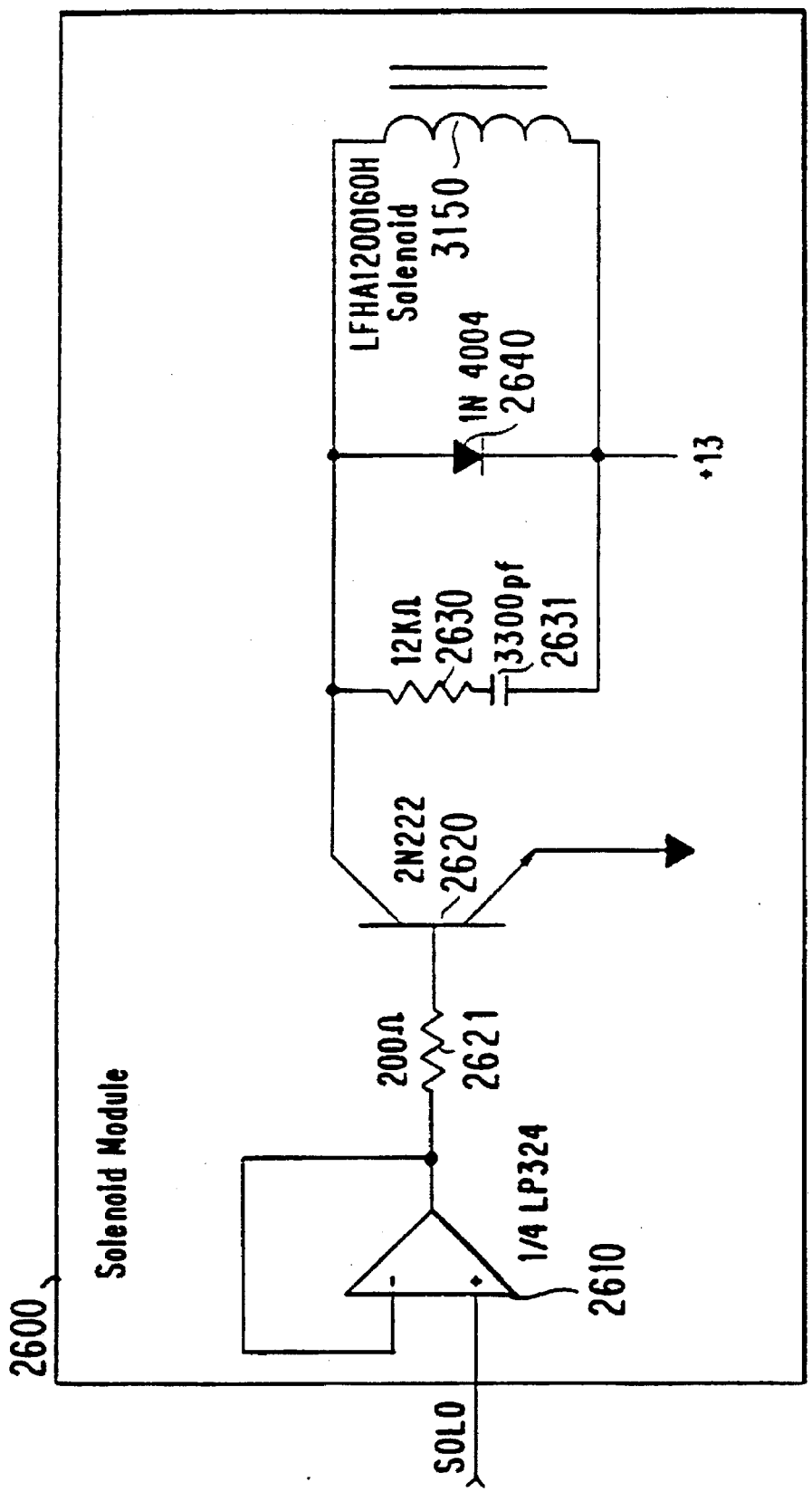
FIG. 10 is a schematic diagram of the solenoid control module of FIG. 4.

Referring to FIGS. 4 and 10, microprocessor 2000 controls the operation of solenoid valve 3150 under software control through module 2600. In operation, module 2600 causes solenoid valve 3150 to deliver a pulse of aerosolized medication when the digital output line PA5 at pin 29 of microprocessor 2000, delivered to module 2600 as line SOLO, is brought high. Module 2600 includes amplifier 2610, current limiting base resistor 2621 (200 Ω), switching transistor 2620, resistor 2630 (12KΩ) and capacitor 2631 (3300 picofarads) connected in series, and collectively in parallel with diode 2640 and in parallel with the inputs of solenoid valve 3150 as illustrated in FIG. 10. Solenoid valve 3150 is preferably model No. LFHA1200160H, available from Lee Corporation, Westbrook, Conn., and includes an integral solenoid and valve mechanism wherein the valve is operated by the solenoid. Amplifier 2610 is preferably an amplifier from device model LP324 available from National Semiconductor, Santa Clara, Calif., and is configured in a voltage follower mode. The combination of resistor 2630, capacitor 2631 and diode 2640 suppresses surges during the firing of solenoid valve 3150. Diode 2640 is preferably a conventional model No. 1N4004 diode.

When input signal SOLO is brought high, transistor 2620, preferably a model 2N222 available from Motorola, Inc, Phoenix, Ariz., conducts to cause current to flow through solenoid valve 3150. This causes valve 3150 to open to release a dosage of medication from canister 3200 through flow system 3130 for delivery to and inspiration by the patient. When signal SOLO is brought low, the current stops and valve 3150 closes, terminating the dosage pulse. In accordance with the present invention, the operation of the solenoid valve 3150 is controlled by microprocessor 2000 under software control to provide for improved delivery of aerosolized drugs to the patient's lungs.

Figure 11:
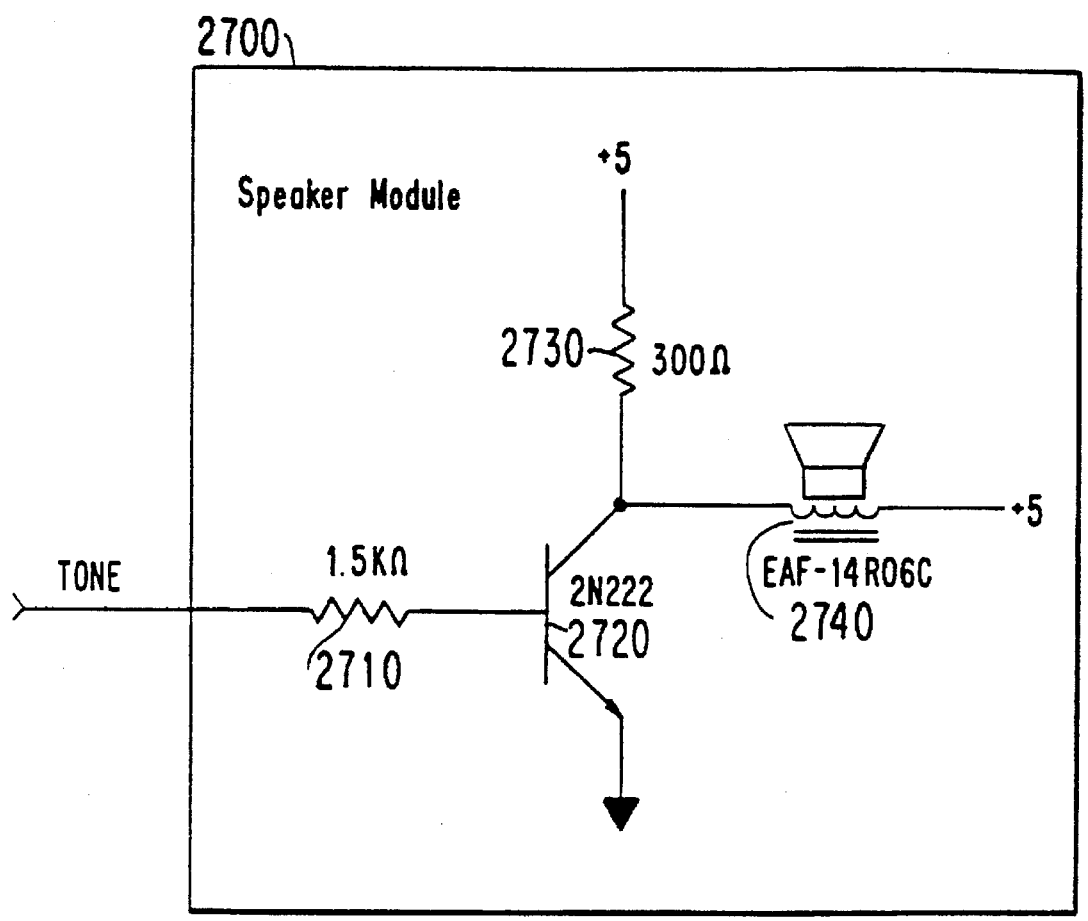
FIG. 11 is a schematic diagram of the speaker module of FIG. 4.

Referring to FIGS. 4 and 11, speaker module 2700 is a one transistor amplifier controlling an audio transducer 2740. A preferred transducer 2740 is model No. EAF-14RO6C, available from Panasonic, Japan. Module 2700 includes transistor 2720, preferably a model 2N222 available from Motorola, Inc., Phoenix, Ariz., configured with a base current limiting resistor 2730 having 1.5KΩ, a reference voltage Vcc of +5 volts fed across, in parallel, collector resistor 2730 having 300 Ω and audio transducer 2740. The transistor emitter is grounded. Input to module 2700 is signal TONE from line PA4 at pin 30 of microprocessor 2000. When transistor 2720 conducts, current flows through collector resistor 2730 and speaker 2740 through the collector of transistor 2720. The current through speaker 2740 is thus the collector current of transistor 2720 when saturated minus the current through resistor 2730. Line PA4 of microprocessor 2000 will be switched under program control so as to introduce a square wave of varying period to the input signal TONE. In this manner, an audible tone proportional to airway flow will be generated.

The audible tone is useful for cuing the patient to breathe in consistent patterns from time to time. In an alternate embodiment, a learning sequence can be programmed into microprocessor 2000 whereby a preselected signal TONE is generated to teach the patient to breath in accordance with a desired breathing pattern for optimal delivery of the particular drug to be administered. Thus, the flow detected can be compared to the preselected signal TONE such that feedback techniques, e.g., using the LED modules, can be use to train the patient to breath in a desirable manner.

In alternate embodiments, speaker 3740 could be replaced by a piezoelectric sheet or material capable of producing audible vibrations or tactile vibrations, the latter being particularly useful for deaf patients.

Referring to FIG. 4, character display subsystem 2800 allows bytes of numeric character data to be sent via the SPI of microprocessor 2000 to a multisegment LED character display 2830. A preferred display 2830 is a model No. NSM2416, available from National Semiconductor, Santa Clara, Calif. The byte representing a single character to be displayed is sent to shift register 2810 via the SPI of microprocessor 2000. This serial interface is configured in a unidirectional manner so that data can be provided by microprocessor 2000 but no data can be sent to microprocessor 2000 over line MISO. All data sent over the SPI will appear on input line DIN at pins 1 and 2 of shift register 2810 and will be clocked in. However, data will only be loaded into display 2830 when the digital output line PD5 at pin 25 is asserted by being brought low. Each byte sent to shift register 2180, preferably model no. 74HC164, available from Motorola, Inc., Phoenix, Ariz., intended for character display must contain the ASCII code of the character to be displayed in bits <0:4> and the two bit position address (00=display position 0; 11=display position 3) of the display location in which the character is to appear in bits <5:6>. The most significant bit (bit <7:7>) is ignored. The outputs of shift register 2810 and display 2830 select line are conditioned by buffers 2820, (preferably part No. 74HC244, available from National Semiconductor, Santa Clara, Calif.). This is done to allow CMOS level signals from microprocessor 2000 and shift register 2810 to drive inputs of the TTL display 2830.

In an alternate embodiment, display module 2800 may be configured under appropriate software instruction (not shown) and with additional hardware and wire connections so that the full set of ASCII coded bits can be transmitted for providing visual prompt alphanumeric information to the patient and to display various measured parameters to the patient and the medical examiner. Such a display module 2800 could be used to instruct the patient how to use the device for measuring a pulmonary function, specifically FEV1, or to obtain a desirable inspiratory flow. These instructions could include, for example, "take a breath now" indicating that the device is ready, "hold your breath longer" during an inspiratory pause period or other messages, for example, whether or not to breath harder on expiration. Thus, in addition to displaying the number of does remaining, display module 2500 can be used on the one hand to prompt the patient to breathe in accordance with selected flow patterns for measuring specific pulmonary functions, and on the other hand to prompt the patient to breathe consistently from breath to breath and thus optimize use of the device for the intended drug therapy.

Further, display module 2800 also could be used under appropriate software programming (not shown) to display the amount of medication dispensed or given effectively, which may differ from the amount dispensed and the amount of medication remaining, and provide a clinical acuity index more detailed than that provided by LED annunciator modules 2300, 2400 and 2500. Also, display module 2800 be used to instruct the patient to contact the medical examiner in the event of a determined lack of improvement in the patient's measured pulmonary functions over a predetermined period of time during the course of treatment, a determined decline in condition or a repeated inability to deliver medication in either or both of ProgBreathMode or CalBreathMode (as described below).

Similarly, display module 2800 can provide the patient alphanumeric information regarding the times and dates medication is to be administered, battery condition, and diagnostics for the condition and operation of the device, and, in conjunction with microprocessor 2000 and speaker 2740, generate a tone when the conditions require servicing the device or a battery needs to be changed.

Referring to FIGS. 12 and 13A–13E and the software appendix, a software flowchart and subroutine calling chain corresponding to the program of the software appendix are illustrated. Subroutines 100 automatically perform system initialization on Reset. Control then transfers to system main loop IdleLoop 000 which repetitively executes subroutines CheckAlarm 200, GetDataPoint 300, CheckThreshold 400, IntegrateOn 500, LoggingOn 600, ProcessBreath 700, IntegrateOff 1000, and LoggingOff 1010, in accordance with the algorithm described below, forever.

Subroutine 200 checks the system's real time clock and compare the current time (in hours) to a stored list of recommended dosing times for the patient and the selected medication. If the current hour appears on this list, subroutine 210 causes microprocessor 2000 to provide a signal TONE to generate an audible alarm on module 2700 once for that hour. In the present embodiment the alarm serves as a recommendation to the patient that a dose is to be taken, but does not control or alter the function of the rest of the program. After the alarm clock functions have been performed, control transfers to subroutine GetDataPoint at branch point 300 which measures the instantaneous flow in airway 3140.

Figure 12:
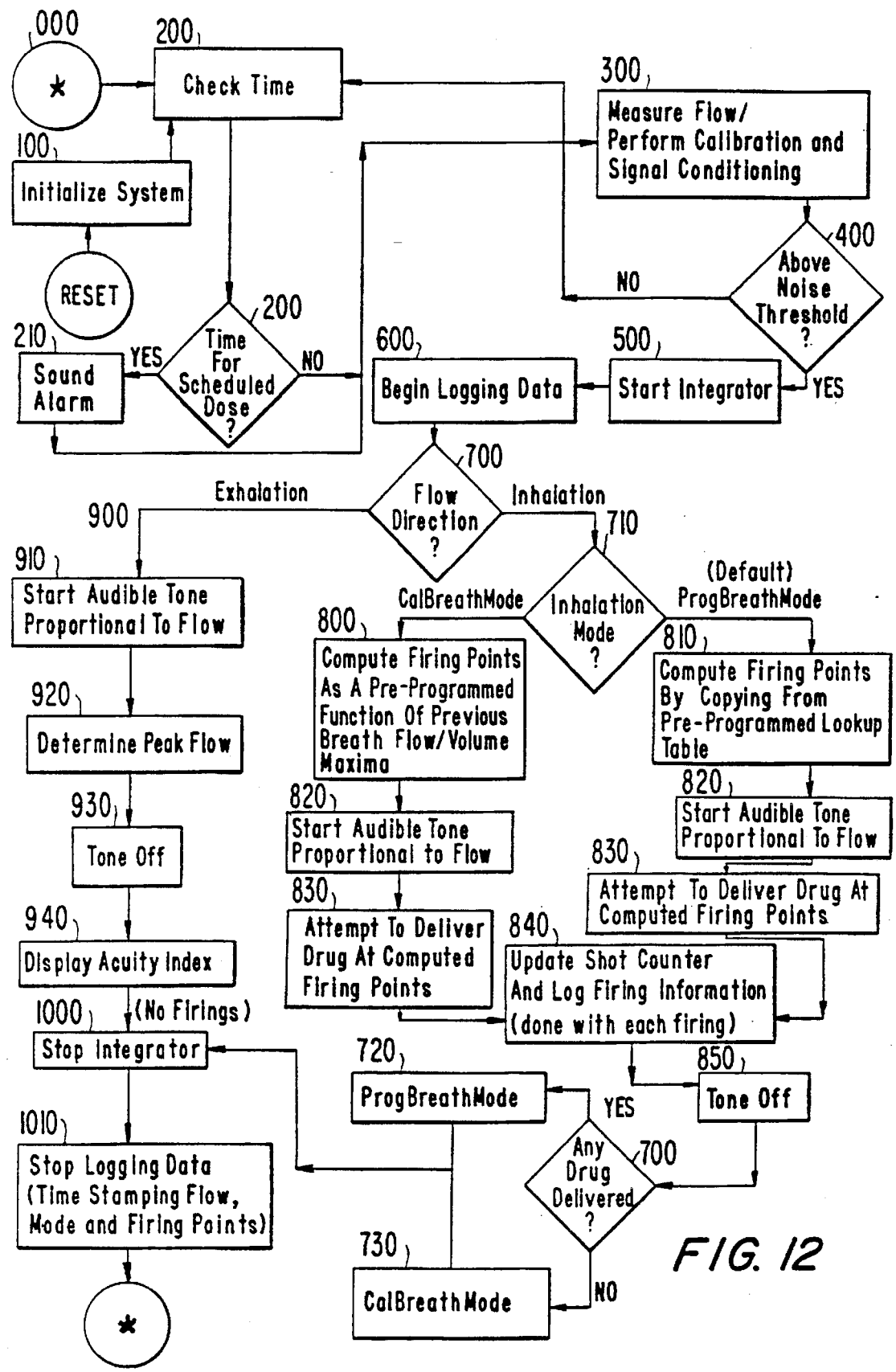
FIG. 12 is a flow chart of the software of a preferred embodiment of the device of FIG. 4 in accordance with the present invention.
Figure 13A:
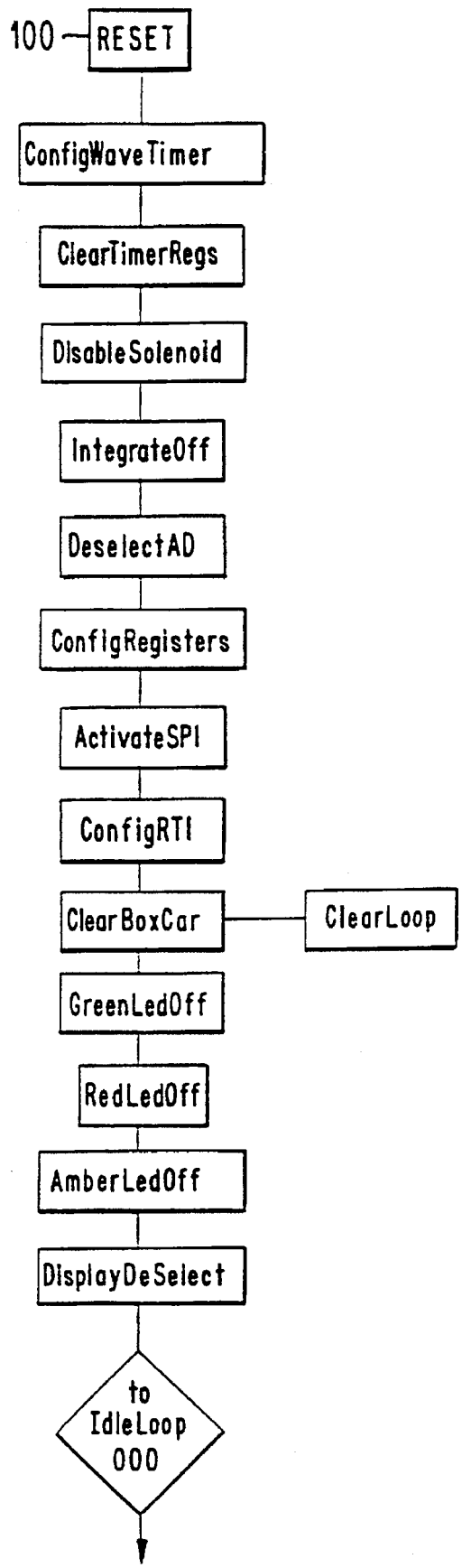
FIGS. 13A–13F are collectively a flow chart of the subroutine calling chain of the software embodiment of FIG. 12 and the software appendix.
Figure 13B:
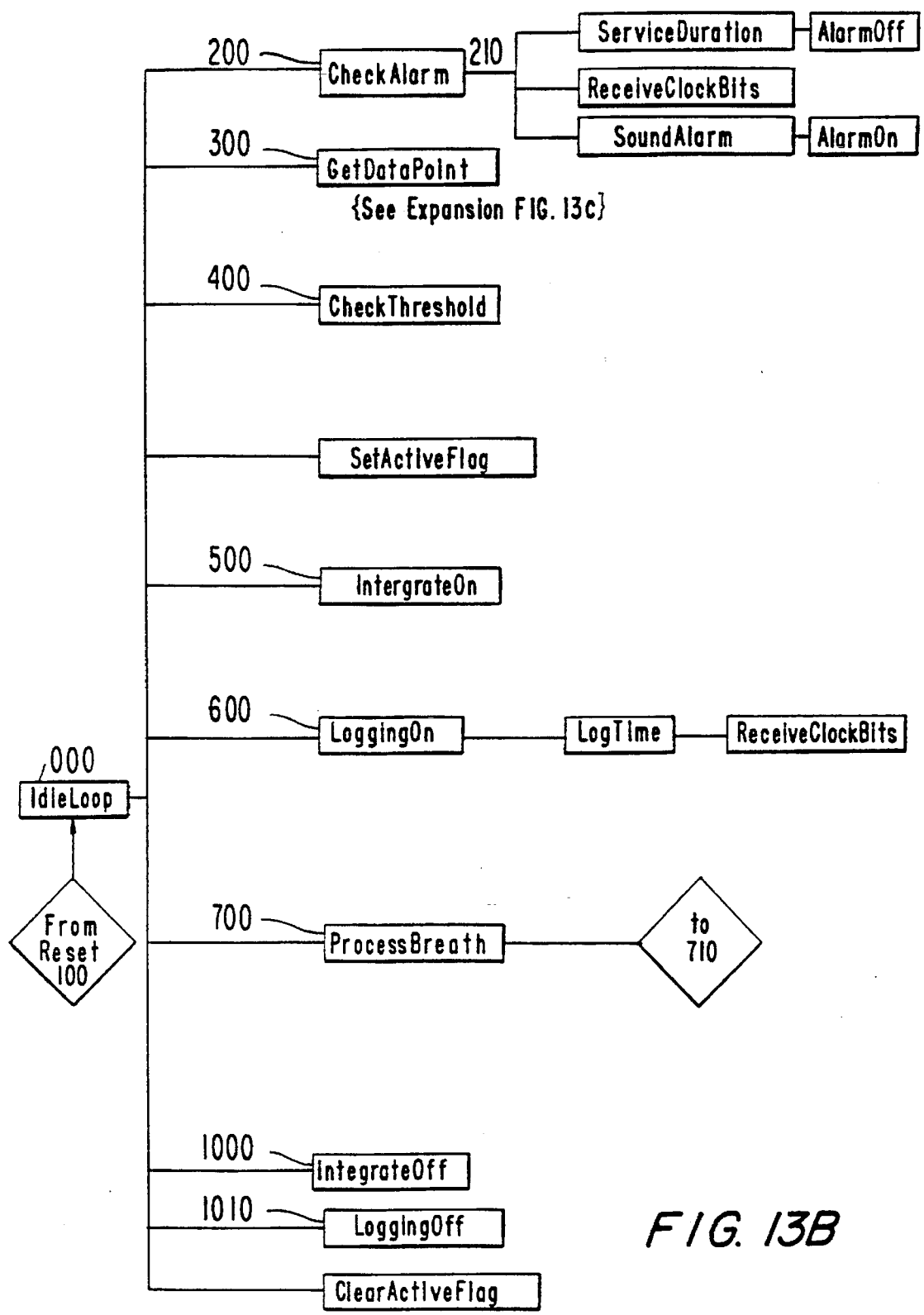
Figure 13C:
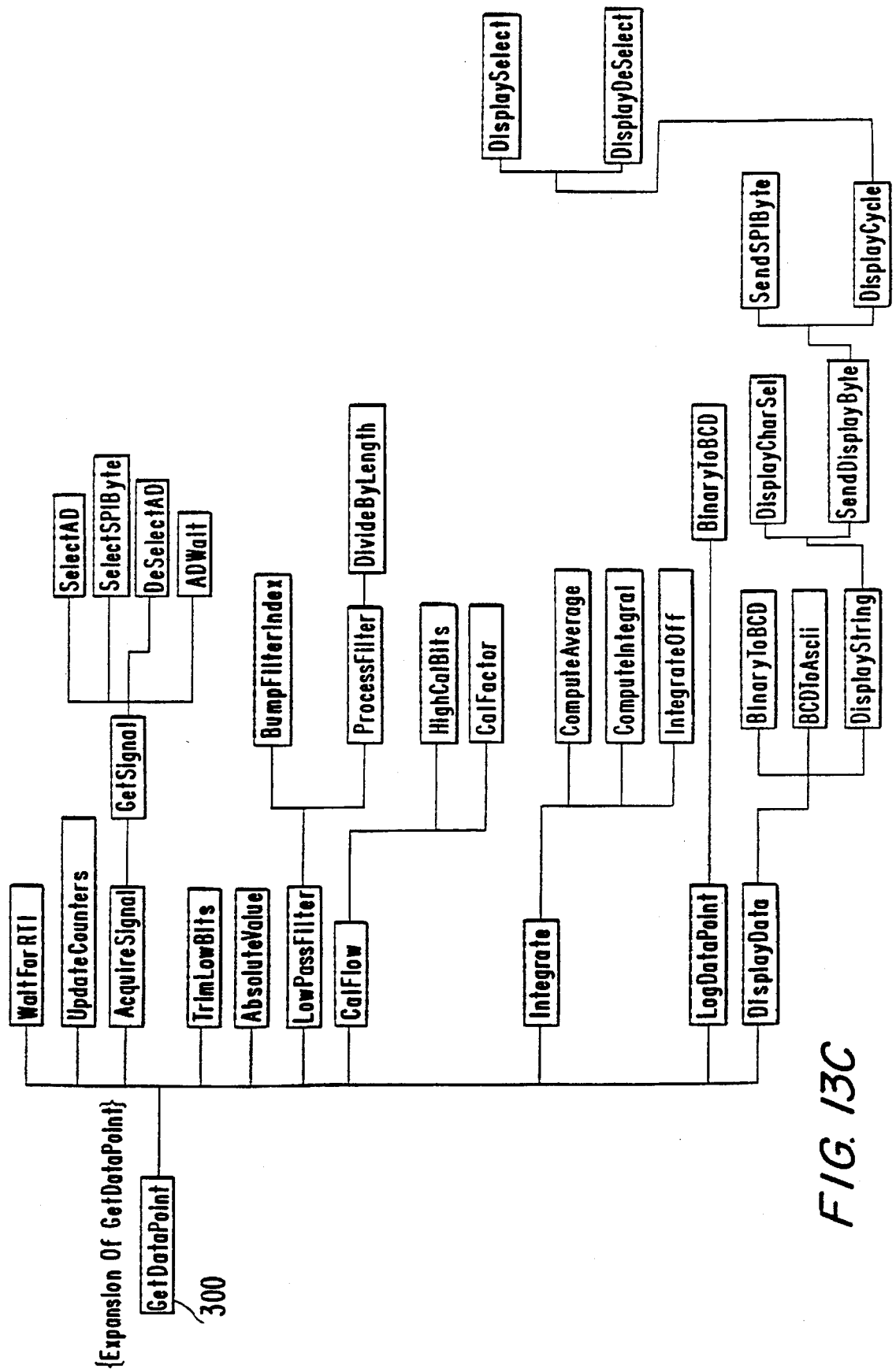

Referring to FIGS. 12 and 13C, flow is measured by the series of routines beginning with GetDataPoint. These routines perform data acquisition, signal processing, calibration, integration, data logging and information display functions.

Routine GetDataPoint begins by holding for a real time interrupt WaitForRTI, resulting in a 60 Hz sample rate because of initial configuration by the ConfigRTI routine executed during the Reset sequence. On a 1/60 second real time event mark, a flow data point is acquired from ADC 2210 by routine AcquireSignal.

The datapoint obtained from ADC 2210 by AcquireSignal is a 12 bit signed quantity (without sign extension). Signal processing begins by removing the lower two bits, which are assumed to be noise, by routine TrimLowBits, and proceeds with subsequent application of an 8 element moving average low pass digital filter by routine LowPassFilter.

The trimmed, low pass filtered flow data point value is then converted to its absolute value by routine AbsoluteValue and the sign bit stored for subsequent use by decision points requiring flow direction information (sign bit unity=>inhalation, sign bit zero=>exhalation).

The absolute value of the trimmed, filtered flow data point is then converted to a binary representation of flow in liters per minute by application of routine CalFlow. A rough conversion is first obtained by multiplying the uncalibrated value by two. A more accurate calibration is possible by applying correction factors to this rough calibrated value as a function of value. In the limit, one could store $2^n-1$ correction factors for an N bit value, thereby forming a calibration array for application to each digitized data point for overcoming arbitrary nonlinearity in the mapping of the differential pressure and the flow rate. In this embodiment, the array comprises 16 correction factors which are stored in a lookup table and applied to the rough calibrated value based on the value of the high four bits. Such an approach enables airway pneumotachs with non-linear pressure/flow characteristics to be employed. The details of the calibration algorithm are explained in the software appendix code listing under the section labeled Flow Calibration Data, although the calibration constants were set to zero in that embodiment for testing purposes.

The processed flow data point is then sent as argument to the integration routines Integrate. An integration algorithm described in detail in the code listing section labeled Integration Data is then performed.

The processed flow data point is then logged and the data display (showing the value of the shot counter, i.e., how many dosages of medication remain in canister 3200) is updated. If this flow is above the noise threshold, program control is transferred to branch point 500 and the breath processing functions, otherwise control returns to branch 200 and CheckAlarm and the alarm check functions are again executed.

Referring to FIGS. 12 and 13B, the breath processing functions begin at point 500 which starts the real time integration of measured airway flow to yield volume. Data logging is then begun at branch point 600 by storing the date, time and mode information in the data logging array in memory module 2100. The mode information is either ProgBreathMode at branch point 720 or CalBreathMode at branch point 730 as described below.

Subroutine ProcessBreath next begins at branch point 700 by further branching based on flow direction to the exhalation (peak flow meter function) or inhalation (drug delivery) routines.

Figure 13D:
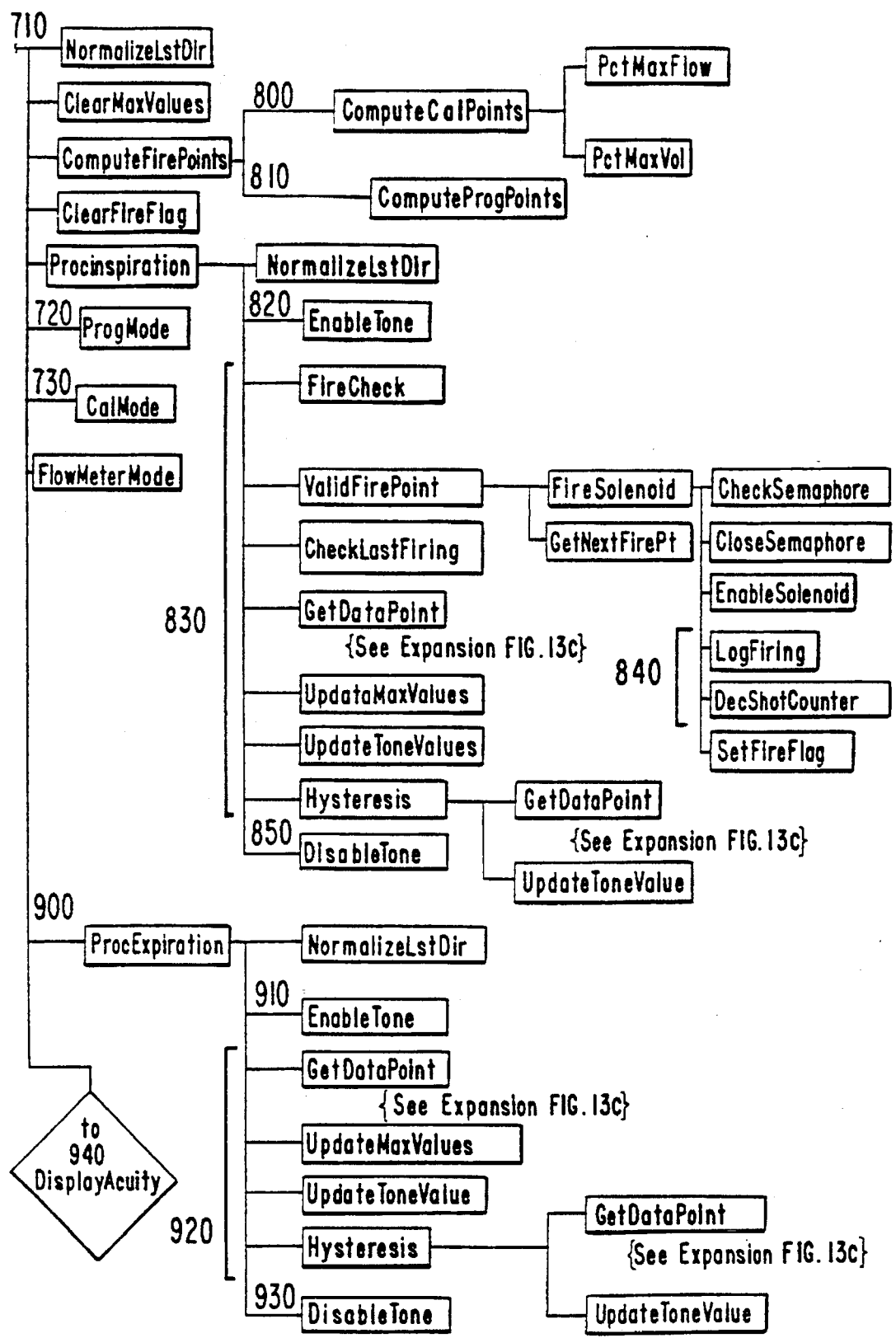
Figure 13E:
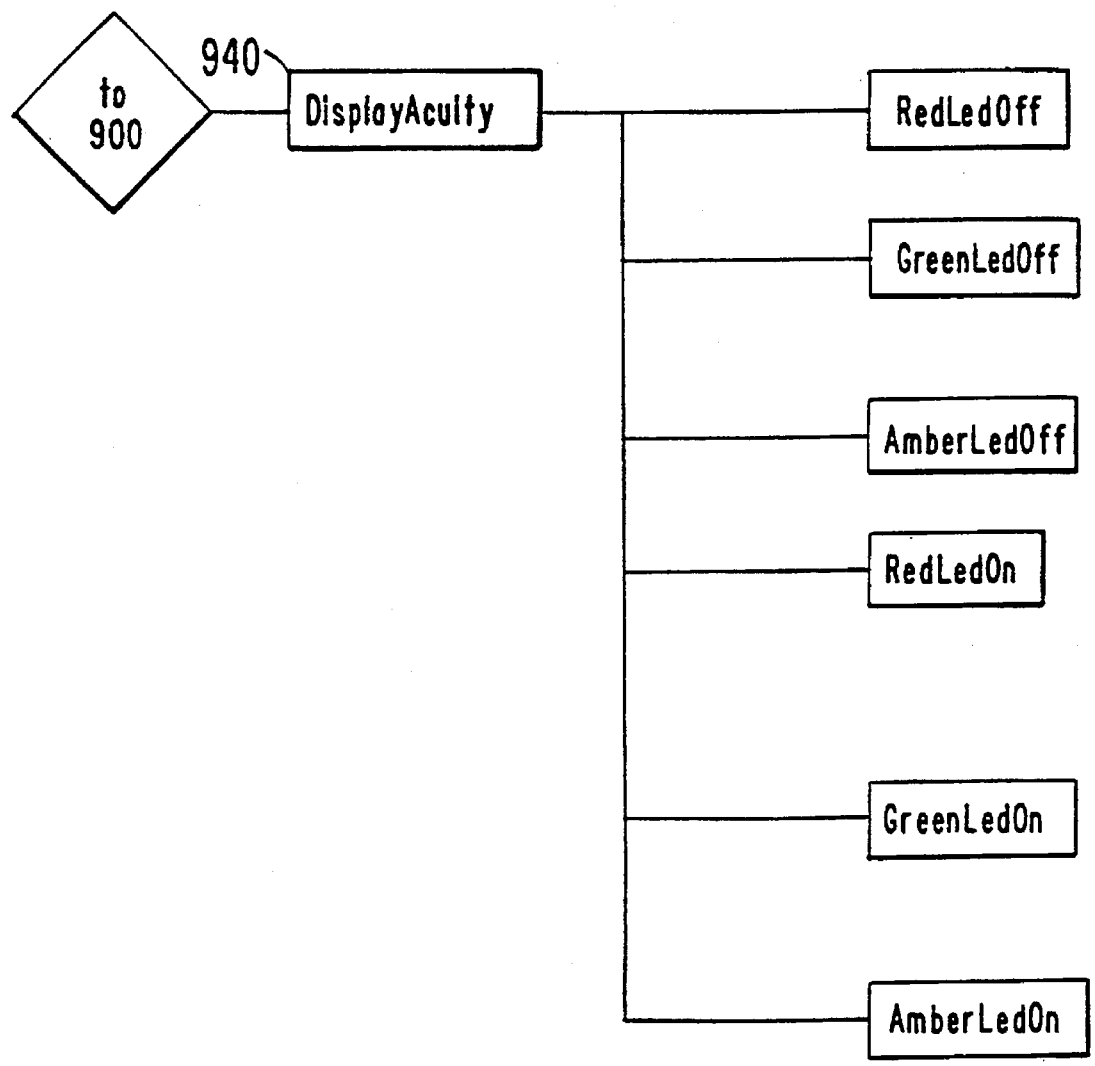
Figure 13F:
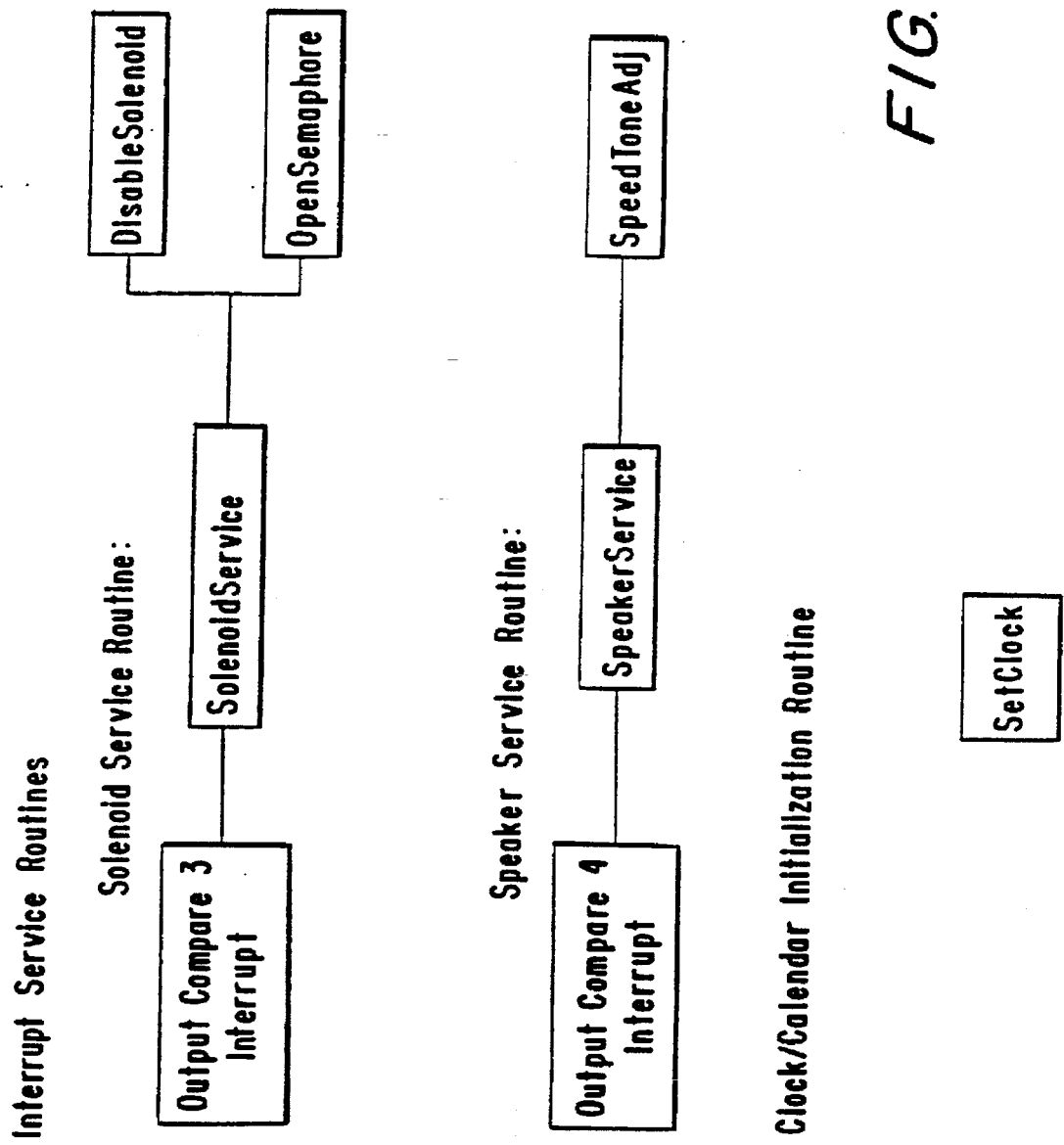

Referring to FIGS. 12 and 13D, the inhalation function begins at branch point 710 by checking for the current mode for drug delivery. If the device is in ProgBreathMode, or the device operates in the default mode (ProgBreathMode), the routine ProcessInspiration attempts to deliver drug at preprogrammed absolute flow and volume firing points. This process begins at branch point 810 where the flow and volume firing points pre-programmed in non-volatile system memory are copied into vectors FlowPoints and VolPoints (see Firing Point Data area the software appendix in code listing). This process results in the production of "scheduled flow/volume firing points." An audible tone proportional to the instantaneous measured airway flow is started at point 820. Routines 830 continuously monitor the measured flow rate and volume during the inspiration and deliver drug as each successive pre-programmed flow/volume firing point now in vectors FlowPoints and VolPoints is reached. A flow/volume firing point is defined as a point during inspiration where both the instantaneous flow rate and flow volume are greater than or equal to a preprogrammed flow rate and flow volume pair.

Routines 830 then deliver drug as each firing point is reached. Routines 840 decrement the shot counter which provides a numeric character display for the user indicating the number of doses of drug remaining, and advance pointers stored at NxtFireFlow and NxtFireVol. These pointers will then be indicating the next flow/volume firing point (if preprogrammed) stored in vectors FlowPoints and VolPoints.

Flow/volume firing information for the Programmed Breath Mode is stored in the Firing Point Data area in the software appendix code listing. The FireCount variable encodes the maximum number of possible firing points. Vectors FireFlow and FireVolume together encode flow/volume firing point pairs where FireFlow[i] and FireVolume [i] refer to firing point i. Flow rate is expressed in liters per minute, flow volume in liters. Preferably, as each firing point is reached, a uniform pulse is generated In an alternate embodiment, variable size pulses may be generated in accordance with a selected schedule relating the time of delivery of the successive firing points to the desired location of deposition of the aerosol particles.

If the system is currently in CalBreathMode, i.e., calibration breath mode, control is transferred at branch point 710 to the routines ComputeCalPoints at branch point 800. These latter routines load the FlowPoints and VolPoints flow/volume firing point data arrays. Instead of copying preprogrammed flow/volume firing point data into the FlowPoints and VolPoints arrays as was done by routine ComputeProgPoints, routines at branch point 810, routines ComputeCalPoints at point 800 calculate flow/volume firing points based on the flow/volume maxima achieved during the preceding breath. This process results in the production of "scheduled flow/volume firing points."

Vectors PctFireFlow and PctFireVol contain the preprogrammed percent of maxima information used by routines ComputeCalPoints to make the flow/volume firing point calculations. These percent factors are encoded as the number of right shift operations needed to generate the desired percentage from a binary representation of the original value. Thus, unity represents 50%, two represents 25%, three represents 12.5% and so on.

Routines ComputeCalPoints apply percentage information contained in vectors PctFireFlow and PctMaxFlow to flow and volume maxima, respectively, measured during the last breath. A plurality of absolute flow/volume firing points (the exact number of firing points determined, as in ProgBreathMode, by the preprogrammed variable FireCount) are constructed, and placed in the FlowPoints and VolPoints vectors.

Control is then transferred to routines 820 and 830, and are again used, as they were in ProgBreathMode, to start an audible tone proportional to measured airway flow (routine EnableTone at branch point 820) and to deliver drug at the now appropriate flow/volume firing points (routines 830). The flow/volume firing points now resident in vectors FlowPoints and VolPoints are again consulted by routines 830 and used to trigger solenoid 3150 upon satisfaction of these thresholds.

It is the plurality of flow/volume firing point data loaded into the FlowPoints and VolPoints vectors by routines 800 and 810 respectively that distinguishes the behavior of the system during CalBreathMode and ProgBreathMode. In particular, during ProgBreathMode an attempt is made to deliver drug at invariant, pre-programmed firing points. During CalBreathMode, an attempt is made to deliver drug at flow/volume firing points determined through the application of pre-programmed percentage constants to the flow and volume maxima determined during the previous breath.

After all single inhalation scheduled drug deliveries have been made, or when measured flow changes direction, the audible tone proportional to flow is disabled by routine 850 and the appropriate mode for the next breath is determined at branch point 700. If some drug was delivered, it is assumed that the patient was making an acceptable inspiratory effort (even though all scheduled drug deliveries may not have taken place). In the case that some drug was delivered, the next mode will be ProgBreathMode, selected by routine ProgMode at branch point 720. On the other hand, if no drug was delivered, the assumption is made that the patient made an inadequate inspiratory effort, and was unable to meet any of the flow/volume firing point criteria for the previous breath. In this case, CalBreathMode is selected for the next breath by routine CalMode at branch point 730.

By entering CalBreathMode, the system is accommodating to individual patient characteristics when the patient has demonstrated an inability to generate sufficient inspiratory flow and volume to meet even one scheduled flow/volume firing point. By calculating new firing points as a fraction of flow/volume parameters actually achieved during the previous breath, the chance of achieving a drug delivery during the subsequent breath becomes more likely. In other words, if none of the more desirable (i.e., relatively late in the cycle) scheduled flow/volume firing points can be met by a patient's inspiratory effort, then new scheduled flow/volume firing points occurring earlier in the inspiratory cycle, i.e., at relatively lower flow rates and flow volumes, are more desirable than no drug delivery at all.

In accordance with the present invention, if no drug is delivered during an inspiration in the CalBreathMode, CalBreathMode will again be entered, and new scheduled flow/volume points corresponding to lower flow rates and volumes will be calculated based on the new flow/volume maxima achieved during the most recent previous breath. This strategy virtually ensures that some drug will be eventually delivered, even if the patient's inspiratory effort is deteriorating from breath to breath.

Referring to FIGS. 12, 13B, and 13D, after selection of the next breath mode by routines ProgMode at point 720 or CalMode at point 730, the integration process is stopped by routine IntegrateOff at point 1000 and the data logging stopped by routine LoggingOff at point 1010. During each breath, a log of all measured flow data is kept in an array into which is also stored the time and date, mode and (flow) points in the array where drug was delivered. The format of this array can be found in the software appendix code listing in the section labeled Data Logging Area.

This completes the description of the behavior of the software branching routines during an inhalation.

Referring to FIGS. 12, 13B, and 13D, if an exhalation is detected at decision branching point 700, control is transferred to exhalation handling routines ProcExpiration at branching point 900. Routine EnableTone at point 910 activates an audible tone proportional to measured airway flow. Flow is continuously measured and data points are logged until flow direction reverses. Routines 920 detect peak flow by noting the flow prior to the point of flow reversal. This peak flow point is mapped into a three level clinical acuity index by routines DisplayAcuity at point 940 through the use of pre-programmed constants stored at AcuityGreen, AcuityAmber and AcuityRed. The appropriate declarations can be found in the software appendix code listing in the section labeled Pulmonary Function DATA.

If the measured peak flow is greater than or equal to the value stored at AcuityGreen, a green light emitting diode is illuminated by routines 940 indicating that the patient's condition is nominal. If the measured peak flow is greater than or equal to the value stored at AcuityAmber, and less than the value stored at AcuityGreen, an amber light emitting diode is illuminated by routines 940 indicating that the patient's condition is marginal. If the measured peak flow is greater than or equal to the value stored at AcuityRed, and less than the value stored at AcuityAmber, a red light emitting diode is illuminated by routines 940 indicating that the patient's condition is unacceptable.

Subsequent to display of the acuity index, the integration is stopped by routine IntegrateOff at point 1000. Note that volume information is not used during the processing of an exhalation by this embodiment. However, in an alternate embodiment, such volume data could be used to calculate valuable pulmonary function indices such as the FEV1 (volume exhaled in one second) and vital capacity (VC). The FEV1 could be used to provide more clinical acuity information to the patient than the three level index based on peak expiratory flow now displayed. Further note that, although the volume information is not being used to calculate the FEV1 in this embodiment, the FEV1 could be calculated later through analysis of the logged flow points of data.

Control then continues to routine LoggingOff at point 1010 which stops data logging, as was done during inhalation mode described earlier.

The preferred embodiment makes extensive use of internally programmed constants which influence the system behavior. These constants are readily changed in the current embodiment through the use of a microprocessor emulator system which allows an MS-DOS computer to be used to arbitrarily modify a plurality of non-volatile system memory locations containing either program or data.

It is intended that the software programs be flexible in design so that the system can be configured for use with a particular patient by selecting certain processing subroutines, calibration coefficients, and operating parameters from a library of such information, or from an external source, for use by the main program to accommodate patient specific or drug specific requirements in different applications to treat predetermined medical conditions. Thus, the software controlling the device can be configured or customized for a specific use by a specific patient. Accordingly, when the device is used for a different patient or medication or both, the software can be reconfigured for such use.

In another alternate embodiment of the present invention, the software is programmed to measure pulmonary function periodically, preferably prior to each administration of a dosage, and look for changes in the detected flow patterns and measured pulmonary functions of the patient during the course of treatment. Those detected changes are then used to modify the treatment parameters in accordance with the improved or degenerated condition of the patient. -For example, the dosage per administration and the frequency of administration could be adjusted as indicated by detected changes in the patient's condition. Similarly the dosage could be adjusted from administration to administration by measuring the time between administration to determine a maximum allowed dosage based on accepted medical practices.

In another alternate embodiment of the present invention, each canister 3200 is provided with a code that identifies the contents of the canister, and system electronics 3400 includes means (not shown) for reading a code associated with canister 3200. In one such embodiment, the code is entered externally and in another such embodiment the code is provided automatically when canister 3200 is inserted into base 3100. The code may be read each time canister 3200 is inserted into base 3100 and used by microprocessor 2000 to customize the software programming for delivery of the particular medication. In one embodiment, the code is in the form of product labeling, e.g., a universal bar code, and a code sensor for reading a printed universal bar code (not shown) comprises a photodetector array and a light emitting diode to provide illumination for the photodetector array to read the bar code. Preferably, the bar code is of the circular form so that it can be read regardless of the orientation of canister 3200 in base 3100. In another embodiment, the code may be a digital word integral with the canister and a code sensor for reading the digital word could include electrodes in the base for engaging the code that are connected to the microprocessor. If necessary, the changes in the software for delivery of a particular drug that cannot be provided by a code scheme could be installed in microprocessor 2000 software at the time the device and medication are given to the patient. Alternately, the microprocessor could be configured to request the information from an external source when the code provided is not in the library of selected medications. This programming may be performed by changing the EEPROM or its contents by providing appropriate instructions to microprocessor 2000 or its associated memory through a conventional external communications port.

Preferably, the code also identifies the application for that medication in circumstances where the medication is useful for more than one application or may be used in conjunction with more than one carrier composition having different affinities for deposition. Thus, the code will provide information concerning dosage amounts and times and will provide the information for controlling solenoid 3150 to select an aerosol having a desired particle size distribution for favorable deposition into desired locations in the patient's pulmonary system. This will ensure that the medication is delivered in accordance with its intended delivery characteristics and protocols.

In an alternate embodiment, the software routine could be modified to operate in the calibrated breath mode all the time such that a first breath flow must be acquired and evaluated to identify initial desired threshold firing point or points in the measured flow to administer the medication for the most efficacious inspiration, and to use that information during a second inspiratory flow to actuate solenoid valve 3150 to administer the medication when the flow in a second acquired inspiration corresponds to the identified threshold desired points. In this embodiment, speaker module 2700 could be driven by microprocessor 2000 to prompt the patient to conduct the second inspiration with the same breathing pattern used in the first measured inspiration by recording the flow rate tones of the first inspiration and regenerating those tones in the second breath.

Measuring flow without drug delivery also provides several advantages. For example, displaying the visual acuity index corresponding to the measured expiratory flow can instruct the patient to seek immediate medical attention. Thus, the patient is advised of the need for medical attention when they might not otherwise realize that they need it. This is of particular concern when a patient has just been to a doctor and, absent such displayed information, would not think it necessary to return to the doctor so soon, waiting instead for the prescribed medication to take effect. For another example, it permits obtaining an initial or baseline breath pattern for the patient based on one or more inspirations and expirations e.g., FEV1, vital capacity, and peak expiratory flow. If more than one breath pattern is used to obtain the baseline, the recorded data can be averaged to form the baseline pattern. This baseline can be used to determine gross changes in the patient's pulmonary functions which can be displayed to the patient or relayed to the medical examiner or both to provide an ongoing assessment of the therapy program.

Obtaining a baseline pattern provides several advantages. First, the determined pattern can be used to determine the optimum point or points in the inspiratory flow for delivery of aerosolized medication for the selected medication in its particular application. Thus, the administration of the drug can be based on the patient's actual flow patterns, including inspiratory flow, inspiratory pause, and expiratory flow, and automatically released when the predetermined point or points in the flow occurs. This permits adapting the device to the patient and providing a more effective means for delivering aerosolized medication.

Second, the patient's determined baseline flow pattern can be used as a predictor to account for changes in the patient's breath patterns. Thus, a subsequent inspiration, during which the aerosolized medication will be delivered, can be detected in real time and compared to the previously determined baseline pattern. Any differences in the patterns can be identified. The baseline pattern can then be used to predict the remaining portion of the real time inspiratory flow taking into account the prior deviations in the real time inspiration. This permits adjusting in real time the actual point or points to administer medication, as compared to basing the administration on the occurrence of the predetermined optimal point or points derived from the baseline pattern. Thus, breath to breath variations in the patient's breathing patterns can be identified and used to adjust the administration of medication.

Third, the determined pattern can be used to generate an audible prompt, for example, a tone generated by speaker 2740 that changes in volume or frequency to correspond to changes in the predetermined baseline breath pattern. Thus, the tone can be used to prompt the patient to follow the previously determined baseline breathing pattern so that the delivery of aerosolized medication can be predictably delivered at the desired point or points in the patient's breathing pattern. The prompt, based on the predetermined breathing pattern, thus helps improve the efficiency of the drug delivery.

Fourth, the determined baseline pattern can be compared to a preferred ideal breathing pattern for optimal delivery of the medication. If substantial differences are found to exist, which differences might affect the efficacy of the drug, the prompt then could be used to drive the patient's breathing pattern, i.e., to prompt the patient to modify his or her regular "baseline" breathing pattern to conform more or less to the ideal desired pattern for that medication. Thus, the prompt can improve the efficiency of the drug delivery.

In addition, by recording a series of actual inspiratory and expiratory flow data taken over extended time periods, with or without the contemporaneous administration of medication, trend data can be obtained for analyzing the relative success of the drug therapy. This can then be used by microprocessor 2000 in accordance with its software instructions to alter the drug therapy, for example, the dosage of the medication delivered with each administration or the frequency of administration or both. Also, the trend data can be used by the medical examiner to provide additional data regarding the drug therapy to study the drug therapy originally prescribed and to alter the drug therapy as necessary.

Microprocessor 2000 also may be programmed to review the history of the last several administrations of medication prior to an indicated administration to prevent a patient from administering an overdose of medication or to indicate to the patient that insufficient amounts of medication have been administered.

In an alternate embodiment, each canister 3200 may be provided with a battery supply (not shown) and appropriate electrodes to interface with a corresponding receptacle with electrodes on base 3100 (not shown) for powering some portion or all of electronics 3400 of the device. In one embodiment, the battery supply has an expected lifetime that will be sufficient to actuate whatever electromechanical valve is used to administer all of the contents of the canister, and, where appropriate, perform the anticipated flow measurements taken with or without administration of medication, for a given course of therapy involving that particular medication. This advantageously provides for an adequate power supply for operation of the device with a particular medication without requiring the patient to obtain a supply of batteries for use and without regard to what medication is to be administered. In another embodiment, the canister battery is used for example, to power the electromechanical device used to actuate the valve to release aerosol medication, but not to power the flow measuring electronics, the latter being powered by a separate battery located in base 3100 (not shown).

It has been discovered, using the method of cascade impingement to determine an aerodynamic diameter, that by delivering the aerosolized medication in a series of pulses, as contrasted with a single metered dose, the respirable fraction of the delivered aerosolized compound is substantially increased. More particularly, it has been discovered that the aerosol particle size distribution in a pulse sequence is related to the duration of the pulse within the sequence and can be changed by adjusting the duty cycle of the pulses used to generate the aerosol. This effect may be due to more rapid evaporation of propellent or carrier during a short duty cycle pulse sequence as compared with a single pulse.

In one example, a conventional metered dose inhaler device was compared to a device of the present invention using the method of cascade impingement. It was empirically determined that the metered dose inhaler produced a respirable fraction of about 36%. In contrast, the device in accordance with the present invention, operating to deliver the same dose (by weight) in a pulsatile fashion having four uniform discrete pulses, each pulse having a duty cycle of 13% having a pulse width of 112 msec, corresponding to an on time of 14.56 msec and an off time of 97.44 msec, provided a respirable fraction of about 41%. This is believed to be a substantial improvement in aerosol drug delivery.

The method of cascade impingement can be used in an iterative manner to determine empirically the pulse parameters for maximizing the respirable fraction of the aerosolized compound to be delivered. It should be understood, however, that the term "maximized respirable fraction" refers to a selected respirable fraction that is substantially improved as compared to the respirable fraction produced by a standard metered dose inhaler device, but is not intended to refer to an absolute maximum respirable fraction relative to that produced by a metered dose inhaler device.

In accordance with the present invention, valve 3150 is controlled by microprocessor 2000 and is used as a high frequency switch to release a series of pulses of the aerosol medication having a selectable width, shape, and frequency. The pulses are delivered to the patient through nozzle 3160 mouth end 3142 mouthpiece 3110. By selecting the time period and frequency that valve 3150 is open, the pulse width and interval between adjacent pulses can be selected. Having selected for the desired particle size, the patient's breathing pattern can then be used to identify the optimal points or points at which to deliver the pulses of aerosol medication for delivery to the desired locus or loci in the airway. Further, the selected particle size can then be used with an optimal inspiratory flow, inspiratory pause, expiratory flow, and tidal volume to deliver the aerosol medication to the most therapeutically efficacious locations in the patient's airway. It should be understood that each such dose given as a sequence of pulses can be deposited at different loci by changing the delivery schedule with respect to at which point or points in the inspiratory flow the aerosol is delivered for inspration.

Valve 3150 also can be used to control the total dosage delivered during a single administration by providing a selected number of pulses of equal width, or a first selected number of pulses of a first width and a second selected number of pulses of a second width, whether those first and second pulses are delivered in succession, alternately, or randomly, synchronously or asynchronously. Further, valve 3150 could be used to administer the desired dosage over more than one inspiration in the event that the drug therapy requires a dosage that could not be practicably administered in a single inspiration. Changes in the location or the total dosage can be made through changing the control information provided to solenoid valve 3150 by microprocessor 2000 to produce the desired number and size of pulses in response to the desired delivery schedule.

In accordance with this alternate embodiment of the invention, another function of microprocessor 2000 is to select an optimum particle size and delivery schedule for the medication to be administered for the patient. This is achieved by evaluating the specific medication to be delivered, and the nature of the condition, e.g., whether the drug is to be delivered to the large airways, small airways, or both. This function may be enhanced by also evaluating measured flow and determining optimum points in the measured flow to administer the medication, and using that information in a successive inspiratory flow to administer the medication at an appropriate time as discussed herein.

In accordance with an alternate embodiment, the canisters containing the medication could be constructed with an electromechanical valve actuator integral to the canister. Preferably, the actuators are powered by a battery supplied with the canister. In such an embodiment (not shown) the microprocessor would interface with the canister to provide control signals to actuate the valve actuator to select the desired pulse width, interval, and frequency as appropriate for the given circumstances.

In accordance with another embodiment, the apparatus may be provided with a motion detector for determining when the canister of aerosol generating material has been adequately agitated. In this embodiment, the motion detector can be used to prevent delivery of any aerosol until the device indicates that the material has been agitated to cause the material to be sufficiently mixed to provide the desired aerosol. This device is believed to overcome the problem of segregation or sedimentation of the medication and any aerosol precursor, propellant, or carrier material, which is common to canisters containing medication to be delivered in an aerosol, including metered dose devices. Examples of suitable motion detectors include mercury switches that generate a signal in response to the degree of agitation, which signal is then processed to determine when a sufficient amount of agitation has occurred, whereupon the device is then enabled for delivery of an amount of aerosol.

It also should be understood that other valve switch means for releasing pulses of aerosol could be used in place of an integral solenoid and valve. For example, a solenoid could be used to depress the valve stem of a simple canister valve or to move the canister relative to the valve stem, thereby to provide the appropriate pulses.

One preferred application for the present invention is for bronchodilator therapy for asthma. In this embodiment, the device can be used to select for the proper particle size and dosage by providing a plurality of pulses having different or nonuniform widths at different points in the inspiratory cycle to provide small particles for deposition in the small airways and large particles for deposition in the large airways in sufficient amounts to treat effectively the condition. Measured improvements in pulmonary function can then be used to reduce the dosage both in terms of number of pulses and frequency of administrations.

In another application, the device could be used for treatment of a bronchial constriction in the small airways by providing high frequency pulses during optimal points in the inspiratory flow to produce small particles that deposit in the small airways. Measured improvements in pulmonary function can then be used to reduce the dosage both in terms of number of pulses in a given administration and in the frequency of administrations.

Other anticipated uses of the present invention could be to provide optimal delivery of drugs in aerosol form, based on measured inspiratory and expiratory flow, such as beta-agonists, e.g., albuterol for bronchial-constriction, inhaled steroids for bronchial inflammation, pentamidine for pneumocystis prophylaxis in patients who have tested positive for HIV, narcotics, e.g., morphine or other opiate derivatives, for patients having chronic pain, allowing for effective self-medication exploiting the rapid onset of an aerosol medication administration technique, and without substantial risk of overdosing, and with providing the medical examiner a record of the drug administration for evaluation in the event of continued therapy. See also, e.g., the medications identified in D. Kohler, *Lung* (1990) supp., p. 679. The terms inspiration and inhalation are used interchangeably herein and the terms expiration and exhalation are used interchangeably herein. It also should be understood that in place of a software driven microprocessor the present invention could be implemented using a finite state machine, including without limitation solid state finite state machines.

It also should be understood that the terms aerosol and aerosol generating material are used, in the context of this invention, generally to include the medicinal compound and any carrier or propellant, whether a liquid, gas, or solid material.

One skilled in the art will appreciate that the present invention can be practiced by other than the described embodiments, which are presented for purposes of illustration and not of limitation, and the present invention is limited only by the claims. appendix.

The Engineers Collaborative, Inc. 68H  ross Assembler V1.0

SOFTWARE APPENDIX
77 PAGES

```
;                    * * * * * * * * * * *
;                    *  SmartMist(TM) V2.0 *
;                    *      11/25/90       *
;                    *  (C) Reid Rubsamen  *
;                    *   Miris Medical     *
;                    * * * * * * * * * * *

; SmartMist second prototype firmware developed by Reid Rubsamen
; 11/25/90 - 1/26/91. Comments edited 2/27/91.
;
; The second prototype version has the following features:
;
; 1) 68HC11A1 microprocessor operating in expanded multiplexed mode.
; 2) 2*32K Dallas Semiconductor non-volitile SRAM with internal lithium
;    battery and clock/calander function (DS1244Y).
; 3) LTC1290 12 bit serial A/D.
; 4) National Semiconductor 2416 four character LED display interfaced
;    via a shift register as a 3 wire serial device.
; 5) On-board 8MHz crystal oscillator.
; 6) Audio transducer powered by one-transistor amplifier.
; 7) Three LED indicators for display of a three level acuity index.
;
; Copyright (C) 1990,1991 Miris Medical
; This is an original, unpublished work and is proprietary to Miris
; Medical, and may not be divulged or copied in any form whatsoever
; without express written permission from Miris Medical.
;
;                    * * * * * * * *
;                    *  Memory Map *
;                    * * * * * * * *

0000    IntRam        equ    $0000     ; Internal Ram Start
1000    RegBase       equ    $1000     ; Register Start
1040    ExtRam1       equ    $1040     ; External ram block
B800    ExtRam2       equ    $b800     ; External ram block
DFFF    StackInit     equ    $dfff
2000    ClockScratch  equ    $2000     ; Dummy write byte for phantom clock
                                       ; (Dallas 1244Y ram chips have
                                       ; self contained clock. Pick this
                                       ; bank for clock ram since do not
                                       ; want PC to point to clock ram
                                       ; bank during clock ram access)
2001    ExtRam3       equ    $2001     ; External ram block
B600    eeprom        equ    $b600     ; Internal EEPROM Start
BF40    boot          equ    $bf40     ; Special boot rom
BFC0    modes         equ    $bfc0     ; Special modes interrupt vectors
E000    rom           equ    $e000     ; Internal rom Start
FFD6    vectors       equ    $ffd6     ; Regular Interrupt Vectors ;                    * * * * * * * * *
;                    *  Register Map *
```

A1

CONFIDENTIAL

The Engineers Collaborative, Inc. 68   Cross Assembler V1.0

```
                    ;        * * * * * * * * *
                    ;
0000      porta     equ      $00         ; Port a data
0001      res1      equ      $01         ; Reserved
0002      pioc      equ      $02         ; Parallel i/o control
0003      portc     equ      $03         ; Port c data
0004      portb     equ      $04         ; Port b data (output)
0005      portcl    equ      $05         ; Alternate latched c
0006      res2      equ      $06         ; Reserved
0007      ddrc      equ      $07         ; Data direction for c
0008      portd     equ      $08         ; Port d data
0009      ddrd      equ      $09         ; Data direction for d
000A      porte     equ      $0a         ; Input port E
000B      cforc     equ      $0b         ; Compare force register
000C      oc1m      equ      $0c         ; oc1 Action Mask
000D      oc1d      equ      $0d         ; oc1 Action Data
000E      tcnt      equ      $0e         ; Timer counter register
          ;         equ      $0f         ; (two byte register)
0010      tic1      equ      $10         ; Input Capture 1
          ;         equ      $11         ; (two byte register)
0012      tic2      equ      $12         ; Input Capture 2
          ;         equ      $13         ; (two byte register)
0014      tic3      equ      $14         ; Input Capture 3
          ;         equ      $15         ; (two byte register)
0016      toc1      equ      $16         ; Output Compare 1
          ;         equ      $17         ; (two byte register)
0018      toc2      equ      $18         ; Output Compare 2
          ;         equ      $19         ; (two byte register)
001A      toc3      equ      $1a         ; Output Compare 3
          ;         equ      $1b         ; (two byte register)
001C      toc4      equ      $1c         ; Output Compare 4
          ;         equ      $1d         ; (two byte register)
001E      toc5      equ      $1e         ; Output Compare 5
          ;         equ      $1f         ; (two byte register)
0020      tctl1     equ      $20         ; Timer Control 1
0021      tctl2     equ      $21         ; Timer Control 2
0022      tmsk1     equ      $22         ; Timer Interrupt Mask 1
0023      tflg1     equ      $23         ; Timer Interrupt Flag 1
0024      tmsk2     equ      $24         ; Timer Interrupt Mask 2
0025      tflg2     equ      $25         ; Timer Interrupt Flag 2
0026      pactl     equ      $26         ; Pulse Accumulator Control
0027      pacnt     equ      $27         ; Pulse Accumulator Count
0028      spcr      equ      $28         ; SPI Control
0029      spsr      equ      $29         ; SPI Status
002A      spdr      equ      $2a         ; SPI Data
002B      baud      equ      $2b         ; SCI Baud Rate Control
002C      sccr1     equ      $2c         ; SCI Control 1
002D      sccr2     equ      $2d         ; SCI Control 2
002E      scsr      equ      $2e         ; SCI Status
002F      scdr      equ      $2f         ; SCI Data
0030      adctl     equ      $30         ; A/D Control
0031      adr1      equ      $31         ; A/D Result 1
0032      adr2      equ      $32         ; A/D Result 2
0033      adr3      equ      $33         ; A/D Result 3
0034      adr4      equ      $34         ; A/D Result 4
035       res3      equ      $35         ; Reserved
```

A2

CONFIDENTIAL

The Engineers Collaborative, Inc. 68i    Cross Assembler V1.0

```
0036        res4       equ      $36         ; Reserved
0037        res5       equ      $37         ; Reserved
0038        res6       equ      $38         ; Reserved
0039        option     equ      $39         ; System Config Options
003A        coprst     equ      $3a         ; Arm/Reset Watchdog Timer
003B        pprog      equ      $3b         ; EEPROM Programming Control
003C        hprio      equ      $3c         ; Highest Pri I-bit and Misc
003D        init       equ      $3d         ; Ram and I/O Mapping
003E        test1      equ      $3e         ; Factory Test Control
003F        config     equ      $3f         ; COP, ROM and EEPROM enable ;                    * * * * * * * * * *
            ;                    * Port a Pin Map  *
            ;                    * * * * * * * * * *

0080        ddra7      equ      %10000000       ; Pin 7 direction
                                                ; (in pulse acc reg)

0008        GreenLed   equ      %00001000       ; Light Green Led
                                                ; (via switching NPN)

0010        speaker    equ      %00010000       ; Speaker waveform 0020        solenoid   equ      %00100000       ; Solenoid waveform 0080        SerialAD   equ      %10000000       ; Serial A/D select ;                    * * * * * * * * * *
            ;                    * Port b Pin Map  *
            ;                    * * * * * * * * * *

; Port B configured for expanded mux mode

;                    * * * * * * * * * *
            ;                    * Port c Pin Map  *
            ;                    * * * * * * * * * *

; Port C configured for expanded mux mode

;                    * * * * * * * * * *
            ;                    * Port d Pin Map  *
            ;                    * * * * * * * * * *

; Port D configured as SPI with HC11 as master:
            ;      MISO fed by serial output of A/D
            ;      MOSI feeding serial inputs of A/D and display module
            ;      SCK  feeding serial clocks of A/D and display module
            ;      !SS tied high ;                    * * * * * * *
            ;                    * SPI Equates *
            ;                    * * * * * * *

0080        spie       equ      %10000000
0040        spe        equ      %01000000
0020        dwom       equ      %00100000
```

A3

CONFIDENTIAL

The Engineers Collaborative, Inc. 68h Cross Assembler V1.0

```
0010        mstr            equ     %00010000
0008        spol            equ     %00001000
0004        cpha            equ     %00000100
0002        spr1            equ     %00000010
0001        spr0            equ     %00000001

0038        SpiDirMsk       equ     %00111011       ; RxD and TxD both configured
                                                    ; as outputs for use as
                                                    ; LED controls.
0053        SpiControlMsk   equ     %01010011

;                       * * * * * * *
            ;                       * SCI Equates *
            ;                       * * * * * * *

; Control Register 1:

0080        r8              equ     %10000000
0040        t8              equ     %01000000
0008        m               equ     %00001000
0004        wake            equ     %00000100

; Control Register 2:

0080        tie             equ     %10000000
0040        tcie            equ     %01000000
0020        rie             equ     %00100000
0010        ilie            equ     %00010000
0008        te              equ     %00001000
0004        re              equ     %00000100
0002        rwu             equ     %00000010
0001        sbk             equ     %00000001

; TxD and RxD ports used as outputs to control Light Emitting Diodes
            ; (via switching transistors)

0001        AmberLed        equ     %00000001       ; Light Amber Led

0002        RedLed          equ     %00000010       ; Light Red Led

;                       * * * * * * * * * *
            ;                       * Port e Pin Map *
            ;                       * * * * * * * * * *

; Internal A/D convertor not used

;                       * * * * * * * * * * * *
            ;                       * Hardware Interrupts *
            ;                       * * * * * * * * * * * *

; !XIRQ and !IRQ are tied high

;                       * * * * * * * * * * * * * *
            ;                       * Mode Select Pin Config *
            ;                       * * * * * * * * * * * * * *

; Both mode pins are tied high (external mux mode)
```

A4

CONFIDENTIAL

The Engineers Collaborative, Inc. 68H... Cross Assembler V1.0

```
                      ;              * * * * * * * *
                      ;              * SCI Config   *
                      ;              * * * * * * * *

; SCI pins are used to control LED's (see SPI equates above)

;              * * * * * * * * *
                      ;              * Timer Control *
                      ;              * * * * * * * * *

0001    SpeedCntrl       equ    %00000001    ; Divide E by 4
0080    TimerIntConfig   equ    %10110000
007F    TimerOvfFlgClr   equ    %01111111

; Tone timer equates

0004    ToggleToneSet    equ    %00000100    ; Set for toggle mode
0008    ToggleToneClr    equ    %00001000    ; Clear for toggle mode
0010    ToneInt          equ    %00010000    ; Mask for tmsk
00EF    ToneFlgClr       equ    %11101111    ; OC4 flag clear mask
0080    LowestToneValue  equ    $0080        ; Lowest allowable value for
                                             ; speaker tone pulse width
                                             ; (ie. highest tone frequency)
0100    ToneOffset       equ    $0100        ; Added into all tone values ; Solenoid timer equates 0010    ToggleSoloPin    equ    %00010000    ; Mask for tctl1 (toggle pin)
0020    SolenoidInt      equ    %00100000    ; Mask for tmsk
00DF    SolenoidFlgClr   equ    %11011111    ; OC3 flag clear mask
0020    SolenoidForce    equ    %00100000    ; Force output compare 3

;              * * * * * * * * *
                      ;              * Display Equates *
                      ;              * * * * * * * * *

0004    DisplayLength    equ    4            ; Number of characters in display
0002    HalfDisplayLen   equ    2            ; DisplayLength/2
0010    AsciiMask        equ    %00010000    ; Drop in b4 to convert to ascii
0020    DispSelPin       equ    %00100000    ; Portd pin to display write line
001F    CharAddrMask     equ    %00011111    ; Character address is dropped into
                                             ; bits 6 and 7.

;              * * * * * * * * *
                      ;              * BCD Conversion *
                      ;              * * * * * * * * *

000E    WordLength       equ    14           ; Largest binary word
                                             ; allowed for BCD conversion ;              * * * * * * * * *
                      ;              * Data Acquisition *
                      ;              * * * * * * * * *

002     SixtyHertzRTI    equ    %00000010
```

A5

CONFIDENTIAL

The Engineers Collaborative, Inc. 68h .ross Assembler V1.0

```
.40         EnableRTI       equ     %01000000
008F        RTIFlagClr      equ     %10111111
0040        RTIFlag         equ     %01000000
003C        MaxTics         equ     60              ; 60 tics/second 0032        ConvertDelay    equ     50

0008        FilterLength    equ     8
0003        LogLength       equ     3
0200        MaxValue        equ     512
000A        DtaWordLength   equ     10

0002        TrimBits        equ     2               ; lsb's to trim off of A/D
                                                    ; word prior to processing 0009        AbsWordLength   equ     DtaWordLength-1 ; Length of word without
                                                    ; sign bit 0004        CalFieldLength  equ     4               ; Number of (high) bits used as
                                                    ; argument to calibration table 0002        SignBitMask     equ     %00000010       ; Use to locate sign bit --
                                                    ; must be changed as a
                                                    ; function of TrimBits 0001        SignBitClr      equ     %00000001       ; Used to clear sign bit ;                       * * * * * * * * * * * *
            ;                       * Pulmonary Function *
            ;                       * * * * * * * * * * * *

0004        TicGroup        equ     4               ; Number of tics to average
                                                    ; together as one integrator
                                                    ; data point
0002        LogTicGroup     equ     2               ; Used to compute average 0014        UpdateTics      equ     20              ; Update integral time
0400        FlowConvert     equ     1024            ; Conversion factor divided into
                                                    ; running sum of tic groups.
000A        LogFlowConvert  equ     10              ; Used for divide 0004        IntegralSecs    equ     4               ; Integration window in seconds
003C        TicsPerSecond   equ     60              ; Determined by RTI rate 00F0        IntegralTics    equ     IntegralSecs*TicsPerSecond 0064        NoiseAmplitude  equ     100
0000        ExhaleSignBit   equ     0
0001        InhaleSignBit   equ     1

; PeakFlowMode  -> "Peak Flow Mode"
            ;                 Instrument records peak flow data and provides
            ;                 user with a severity of illness index expressed
            ;                 as one of the folowing colored LED indicators:
            ;                 Green -> Peak Flow nominal
            ;                 Amber -> Peak Flow marginal
            ;                 Red   -> Peak flow unacceptable
            ;
```

A6

CONFIDENTIAL

The Engineers Collaborative, Inc. 68H.. .ross Assembler V1.0

```
; ProgBreathMode -> "Programmed breath mode"
;                   The default drug delivery mode.
;                   Instrument measures and records inspiratory
;                   flow and volume data in real time and delivers
;                   drug at the programmed flow and volume point(s).
;
; CalBreathMode  -> "Calibration breath mode"
;                   CalBreathMode is automatically entered following
;                   a ProgBreathMode inspiration during which
;                   inspiratory effort was insufficient to meet
;                   the pre-programmed flow/volume delivery parameters.
;                   CalBreathMode flow/volume firing points are
;                   calculated from the previous breath flow/volume
;                   maxima. Factors used for this calculation are
;                   stored as percentages of peak inspiratory flow
;                   and peak inspiratory volume.
;

0002        PeakFlowMode    equ     2
0001        CalBreathMode   equ     1
0000        ProgBreathMode  equ     0

;                           * * * * * * * * * * * *
;                           * Data Logging Format *
;                           * * * * * * * * * * * *

;
; Logged data format array index information
;

0000        TimeOffset      equ     0
0007        ModeOffset      equ     7
0008        LengthOffset    equ     8
000A        DataOffset      equ     10

0007        TimeBytes       equ     7       ; Number of time bytes logged
B000        LogFileEnd      equ     $b000   ; Log file boundry (non-inclusive)
0320        MaxLogFileLen   equ     800     ; Maximum length of a single
                                            ; breath log file entry E000                        org     rom ;                           * * * * * * * * * * * *
;                           * Initialization Code *
;                           * * * * * * * * * * * *

PowerOnReset

E000 CE1000         ldx     #RegBase        ; Set up register pointer
E003 8EDFFF         lds     #StackInit      ; Set stack pointer E006 BDE588         jsr     ConfigWaveTimer E009 BDE57D         jsr     ClearTimerRegs E00C BDE874         jsr     DisableSolenoid
E00F BDE403         jsr     IntegrateOff
```

A7

The Engineers Collaborative, Inc. 6E   Cross Assembler V1.0

```
E012 BDE705           jsr     DeSelectAD
E015 BDE6F4           jsr     ConfigRegisters
E018 BDE6A9           jsr     ActivateSPI
E01B BDE576           jsr     ConfigRTI E01E 7FB820           clr     PulseCounter
E021 7FB810           clr     AlarmCounter
E024 7FB836           clr     TicCounter
E027 7FB837           clr     SecondsCntr
E02A 7FB856           clr     ActiveFlag
E02D 7FB84A           clr     FilterIndex16
E030 7FB848           clr     FilterIndex
E033 7FB854           clr     CurrentMode
E036 7FB855           clr     LastInhaleMode
E039 7FB84F           clr     LastDirection
E03C 7FB850           clr     LastMaxFlow
E03F 7FB852           clr     LastMaxVol E042 BDE4D2           jsr     ClearBoxCar E045 BDE71D           jsr     GreenLedOff
E048 BDE70D           jsr     RedLedOff
E04B BDE715           jsr     AmberLedOff
E04E BDE6A5           jsr     DisplayDeSelect E051 OE               cli ;                      * * * * * * *
       ;                      * Main Loop *
       ;                      * * * * * * *
              IdleLoop E052 BDE510           jsr     CheckAlarm       ; Need to sound alarm clock?
E055 BDE34A           jsr     GetDataPoint     ; Get A/D data, perform dsp
                                               ; and time-keeping functions
E058 BDE274           jsr     CheckThreshold   ; Check for flow above
                                               ; noise level E05B 8100             cmpa    #$00

E05D 26F3             bne     IdleLoop         ; Non-zero return indicates
                                               ; threshold not yet reached E05F BDE33F           jsr     SetActiveFlag    ; ActiveFlag used to lock
                                               ; alarm check functions
                                               ; while tone on E062 BDE3DB           jsr     IntegrateOn E065 BDE8E4           jsr     LoggingOn        ; Log all data points during
                                               ; breath processing E068 BDE076           jsr     ProcessBreath    ; Contains inspiration/
                                               ; expiration fork
E06B BDE403           jsr     IntegrateOff E06E BDE92B           jsr     LoggingOff
```

A8

CONFIDENTIAL

The Engineers Collaborative, Inc. 68HC    oss Assembler V1.0

```
E071 BDE346            jsr     ClearActiveFlag

E074 200C              bra     IdleLoop

;                   * * * * * * * * * * * * * * * *
              ;                   * Breath Processing Routines  *
              ;                   * * * * * * * * * * * * * * * *

;*
              ;* SUBROUTINE  : ProcessBreath
              ;* CALLED BY   : IdleLoop
              ;* ASSUMPTIONS : A valid breath is in progress.
              ;* DESCRIPTION : ProcessBreath forks on flow direction, passing
              ;*               control to the exhalation or inspiration handlers.
              ;*               After inhalation, calibration breath checking
              ;*               is done. After exhalation, peak flow is used
              ;*               to generate an acuity index (proportional to
              ;*               severity of the patient's disease).
              ;* REGISTERS   : All are saved.
              ;*

ProcessBreath

E076 36                psha

E077 BDE283            jsr     NormalizeLstDir
E07A BDE116            jsr     ClearMaxValues
E07D B6884F            ldaa    LastDirection
E080 8101              cmpa    #InhaleSignBit
E082 2702              beq     Inhalation
E084 2028              bra     Exhalation Inhalation E086 BDE154            jsr     ComputeFirePts E089 8601              ldaa    #InhaleSignBit
E08B B78884            staa    BreathDir           ; Save initial flow direction
                                                   ; because LastDirection will
                                                   ; be different when we return
E08E BDE863            jsr     ClearFireFlag
E091 BDE0E6            jsr     ProcInspiration E094 FC8887            ldd     MaxVolume
E097 FD8852            std     LastMaxVol
E09A FC8885            ldd     MaxFlow
E09D FD8850            std     LastMaxFlow E0A0 86202B            ldaa    FireFlag
E0A3 2602              bne     ProgBreath
E0A5 2705              beq     CalBreath ProgBreath E0A7 BDE123            jsr     ProgMode
E0AA 2015              bra     EndProcBreath
```

A9

The Engineers Collaborative, Inc. 68HC.. ross Assembler V1.0

```
                CalBreath

EOAC BDE12E           jsr     CalMode
EOAF 2010             bra     EndProcBreath Exhalation E0B1 8600             ldaa    #ExhaleSignBit
E0B3 B7B8B4           staa    BreathDir
E0B6 BDE139           jsr     FlowMeterMode
E0B9 BDE0C3           jsr     ProcExpiration
E0BC BDE2B7           jsr     DisplayAcuity
E0BF 2000             bra     EndProcBreath EndProcBreath E0C1 32               pula E0C2 39               rts ;*
;* SUBROUTINE  : ProcExpiration (meaning Process Expiration)
;* CALLED BY   : ProcessBreath
;* ASSUMPTIONS : An exhalation is in progress.
;* DESCRIPTION : Acquires data points until flow direction
;*               reverses, then holds until flow in noise band.
;* REGISTERS   : acca is used.
;*

ProcExpiration

E0C3 BDE2B3           jsr     NormalizeLstDir
E0C6 B6B84F           lda     LastDirection
E0C9 8101             cmpa    #InhaleSignBit
E0CB 2711             beq     EndProcExp
E0CD BDE620           jsr     EnableTone
E0D0 FCB840           ldd     SmoothValue
E0D3 BDE34A           jsr     GetDataPoint
E0D6 BDE28E           jsr     UpdateMaxValues
E0D9 BDE603           jsr     UpdateToneValue
E0DC 20E5             bra     ProcExpiration EndProcExp E0DE BDE2A7           jsr     Hysteresis      ; Hold until flow in noise band
E0E1 BDE62D           jsr     DisableTone E0E4 4F               clra E0E5 39               rts ;*
;* SUBROUTINE  : ProcInspiration (meaning Process Inspiration)
;* CALLED BY   : ProcessBreath
;* ASSUMPTIONS : An inhalation is in progress.
;* DESCRIPTION : Acquires data points until firing threshold
;*               reached or flow direction changes.
;*               Solenoid is fired as each firing threshold is reached.
```

A 10

CONFIDENTIAL

The Engineers Collaborative, Inc. 68h. Cross Assembler V1.0

```
;*                  After the last firing, or when flow direction
;*                  reverses, holds until the flow signal is in the
;*                  noise band.
;* REGISTERS   : acca
;*

ProcInspiration

E0E6 BDE283           jsr     NormalizeLstDir
E0E9 B6884F           lda     LastDirection
E0EC 8100             cmpa    #ExhaleSignBit
E0EE 2721             beq     EndProcInsp
E0F0 BDE620           jsr     EnableTone
E0F3 FCB84D           ldd     SmoothValue
E0F6 BDE228           jsr     FireCheck
E0F9 2608             bne     ContinueInsp
E0FB BDE26D           jsr     ValidFirePoint
E0FE BDE141           jsr     CheckLastFiring
E101 2708             beq     EndInspiration ContinueInsp E103 BDE34A           jsr     GetDataPoint
E106 BDE28E           jsr     UpdateMaxValues
E109 BDE603           jsr     UpdateToneValue
E10C 2008             bra     ProcInspiration EndInspiration 10E BDE2A7            jsr     Hysteresis          ; Hold until flow in noise band EndProcInsp E111 BDE62D           jsr     DisableTone E114 4F               clra E115 39               rts ;                          * * * * * * * * * * * * * * * *
;                          *  Breath Processing Utilities *
;                          * * * * * * * * * * * * * * * *
;*
;* SUBROUTINE   : ClearMaxValues
;* CALLED BY    : ProcessBreath
;* ASSUMPTIONS  : None
;* DESCRIPTION  : Clears the maximum flow and maximum integral variables.
;* REGISTERS    : Saved.
;*

ClearMaxValues

E116 36               psha
E117 37               pshb

E118 4F               clra
E119 5F               clrb
 1A FDB885            std     MaxFlow
```

A11

CONFIDENTIAL

The Engineers Collaborative, Inc. 68.    Cross Assembler v1.0

```
11D FDB887              std     MaxVolume

E120 33                 pulb
E121 32                 pula

E122 39                 rts

;*
                ;* SUBROUTINE  : ProgMode
                ;* CALLED BY   : ProcessBreath
                ;* ASSUMPTIONS : None
                ;* DESCRIPTION : Selects programmed drug delivery mode for the next breath.
                ;*               This routine will be called subsequent to a breath
                ;*               during which a successful firing took place.
                ;* REGISTERS   : Saved
                ;*

ProgMode
E123 36                 psha

E124 8600               ldaa    #ProgBreathMode
E126 B7B854             staa    CurrentMode
E129 B7B855             staa    LastInhaleMode
                ;       jsr     RedLedOff
                ;       jsr     GreenLedOn E12C 32                 pula E12D 39                 rts
                ;*
                ;* SUBROUTINE  : CalMode
                ;* CALLED BY   : ProcessBreath
                ;* ASSUMPTIONS : None
                ;* DESCRIPTION : Selects calibration breath drug delivery mode for the next
                ;*               breath. This routine will be called subsequent to a breath
                ;*               during which drug delivery failed to take place
                ;*               (due to inadequate volume and/or flow
                ;*               inspiratory effort).
                ;* REGISTERS   : Saved
                ;*

CalMode
E12E 36                 psha

E12F 8601               ldaa    #CalBreathMode
E131 B7B854             staa    CurrentMode
E134 B7B855             staa    LastInhaleMode
                ;       jsr     GreenLedOff
                ;       jsr     RedLedOn E137 32                 pula E138 39                 rts
                ;*
                ;* SUBROUTINE  : FlowMeterMode
                ;* CALLED BY   : ProcessBreath
                ;* ASSUMPTIONS : None
                ;* DESCRIPTION : Indicates current breath is an exhalation (ie.
```

A12

CONFIDENTIAL

The Engineers Collaborative, Inc. 68H_ _ross Assembler V1.0

```
;*            being used to measure peak flow).
;* REGISTERS  : Saved
;*

FlowMeterMode

E139 36           psha

E13A 9602         ldaa    PeakFlowMode
E13C B78854       staa    CurrentMode

E13F 32           pula

E140 39           rts
;*
;* SUBROUTINE  : CheckLastFiring
;* CALLED BY   : ProcInspiration
;* ASSUMPTIONS : None
;* DESCRIPTION : Checks to see if all scheduled firings for
;*               the current breath have taken place. Returns
;*               zero if no scheduled firings remain and unity
;*               otherwise.
;* REGISTERS   : Saved
;*

CheckLastFiring

'141 36           psha

E142 B6B889       ldaa    FireCount
E145 B12008       cmpa    FireCounter
E148 2705         beq     ClearReg0
E14A CC0001       ldd     #1
E14D 2003         bra     EndCheckLast
            ClearReg0
E14F CC0000       ldd     #0

EndCheckLast

E152 32           pula

E153 39           rts
;*
;* SUBROUTINE  : ComputeFirePoints
;* CALLED BY   : ProcessBreath
;* ASSUMPTIONS : None
;* DESCRIPTION : Based on current inspiratory mode, computes
;*               absolute flow and volume firing points for
;*               current breath. If mode is CalBreathMode,
;*               these points are computed using specified
;*               precentages of the last breath maxima for
;*               flow and volume, respectively. If mode
;*               is ProgBreathMode, specified flow and volume
;*               data points are taken unmodified. In both
;*               cases, the flow and volume firing information
;*               is placed into the FlowPoints and VolPoints
;*               arrays.
```

A13

CONFIDENTIAL

The Engineers Collaborative, Inc. 68H₁  ross Assembler V1.0

```
                    ;* REGISTERS    : Saved.
                    ;*

ComputeFirePts

E154 36                     psha
E155 37                     pshb
E156 183C                   pshy
E158 3C                     pshx E159 86B855                 ldaa    LastInhaleMode      ; Enter programmed breath
E15C 8100                   cmpa    #ProgBreathMode     ; mode if (1) last breath was
E15E 270B                   beq     ProgModePts         ; associated with a successful
E160 8102                   cmpa    #PeakFlowMode       ; firing or (2) last breath
E162 2707                   beq     ProgModePts         ; was an exhalation (ie.
                                                        ; peak flow mode)
E164 2000                   bra     CalModePts CalModePts E166 8DE1BD                 jsr     ComputeCalPts
E169 2005                   bra     EndComputeFire ProgModePts E16B 8DE176                 jsr     ComputeProgPts
E16E 2000                   bra     EndComputeFire EndComputeFire E170 38                     pulx
E171 1838                   puly
E173 33                     pulb
E174 32                     pula E175 39                     rts
                    ;*
                    ;* SUBROUTINE   : ComputeProgPoints
                    ;* CALLED BY    : ComputeFirePoints
                    ;* ASSUMPTIONS  : None
                    ;* DESCRIPTION  : Called by ComputeFirePts. Copies specified
                    ;*                 flow and volume firing data into the
                    ;*                 FlowPoints and VolPoints arrays.
                    ;* REGISTERS    : Saved
                    ;*

ComputeProgPts

E176 36                     psha
E177 37                     pshb
E178 3C                     pshx
E179 183C                   pshy E17B CEB8D0                 ldx     #FireFlow
E17E 18CEB8C0               ldy     #FlowPoints
E182 86B889                 ldaa    FireCount
E185 48                     asla                        ; Bytes = words*2
```

A/4

CONFIDENTIAL

The Engineers Collaborative, Inc. 68HC   ross Assembler V1.0

```
                FlowPtsLoop
E186 E600               ldab    0,x
E188 18E700             stab    0,y
E18B 1808               iny
E18D 08                 inx
E18E 4A                 deca
E18F 26F5               bne     FlowPtsLoop E191 CEB8D4             ldx     #FireVolume
E194 18CEB8C8           ldy     #VolPoints
E198 B68889             ldaa    FireCount
E19B 48                 asla                    ; Bytes = words*2
                VolPtsLoop
E19C E600               ldab    0,x
E19E 18E700             stab    0,y
E1A1 1808               iny
E1A3 08                 inx
E1A4 4A                 deca
E1A5 26F5               bne     VolPtsLoop E1A7 18CEB8C0           ldy     #FlowPoints
E1AB 18FFB88C           sty     NxtFireFlow E1AF 18CEB8C8           ldy     #VolPoints
 1B3 18FFB88E           sty     NxtFireVol E1B7 1838               puly
E1B9 38                 pulx
E1BA 33                 pulb
E1BB 32                 pula E1BC 39                 rts
```

```
;*
;* SUBROUTINE  : ComputeCalPoints
;* CALLED BY   : ComputeFirePoints
;* ASSUMPTIONS : None
;* DESCRIPTION : Called by ComputeFirePts. Computes
;*               flow and volume firing points by taking
;*               specified percentages of flow and volume
;*               maxima from previous breath.
;* REGISTERS   : Saved.
;*
                ComputeCalPts
E1BD 36                 psha
E1BE 37                 pshb
E1BF 3C                 pshx
E1C0 183C               pshy E1C2 CEB8D8             ldx     #PctFireFlow
 1C5 18CEB8C0           ldy     #FlowPoints
 1C9 B68889             ldaa    FireCount
```

A15

CONFIDENTIAL

The Engineers Collaborative, Inc. 68HC11 Cross Assembler V1.0

```
E1CC 48                    lsla
E1CD B7B8DC                staa    CalScratch CalFlowLoop E1D0 EC00                  ldd     0,x
E1D2 BDE20A                jsr     PctMaxFlow
E1D5 18ED00                std     0,y
E1D8 08                    inx
E1D9 08                    inx
E1DA 1808                  iny
E1DC 1808                  iny
E1DE 7AB8DC                dec     CalScratch
E1E1 26ED                  bne     CalFlowLoop E1E3 CEB80A                ldx     #PctFireVol
E1E6 18CEB8C8              ldy     #VolPoints
E1EA B6B889                ldaa    FireCount
E1ED 48                    lsla
E1EE B7B8DC                staa    CalScratch CalVolLoop E1F1 EC00                  ldd     0,x
E1F3 BDE219                jsr     PctMaxVol
E1F6 18ED00                std     0,y
E1F9 08                    inx
E1FA 08                    inx
E1FB 1808                  iny
E1FD 1808                  iny
E1FF 7AB8DC                dec     CalScratch
E202 26ED                  bne     CalVolLoop E204 1838                  puly
E206 38                    pulx
E207 33                    pulb
E208 32                    pula E209 39                    rts ;*
;* SUBROUTINE  : PctmaxFlow
;* CALLED BY   : ComputeCalPoints
;* ASSUMPTIONS : Number of bits to right shift in accb
;* DESCRIPTION : Called by ComputeCalPts. Takes percentage
;*               of number passed in register D. (See
;*               comments in Firing Point Data area at end
;*               of code).
;* REGISTERS   : acca,accb
;*

PctMaxFlow

E20A F7B8DD                stab    PctScratch
E20D FCB850                ldd     LastMaxFlow
E210 0C                    clc MaxFlowLoop
```

A16

CONFIDENTIAL

The Engineers Collaborative, Inc. 6E    Cross Assembler V1.0

```
E211 46                 rora
E212 56                 rorb
E213 7AB80D             dec     PctScratch
E216 26F9               bne     MaxFlowLoop E218 39                 rts
```

```
;*
;* SUBROUTINE  : PctmaxVol
;* CALLED BY   : ComputeCalPoints
;* ASSUMPTIONS : Number of bits to right shift in accb
;* DESCRIPTION : Called by ComputeCalPts. Takes percentage
;*               of number passed in register D. (See
;*               comments in Firing Point Data area at end
;*               of code).
;* REGISTERS   : acca, accb
;*
```

PctMaxVol

```
E219 F7B80D             stab    PctScratch
E21C FCB852             ldd     LastMaxVol
E21F 0C                 clc
```

MaxVolLoop

```
E220 46                 rora
E221 56                 rorb
 222 7AB80D             dec     PctScratch
E225 26F9               bne     MaxVolLoop E227 39                 rts
```

```
;*
;* SUBROUTINE  : FireCheck
;* CALLED BY   : ProcInspiration
;* ASSUMPTIONS : Register D contains latest flow data point.
;* DESCRIPTION : Checks to see if (1) current flow is greater
;*               than or equal to current flow firing point and
;*               (2) current volume is greater than or equal to
;*               current volume firing point. If BOTH of these
;*               conditions are true, zero is returned. Otherwise
;*               the routine returns unity.
;* REGISTERS   : acca, accb
;*
```

FireCheck
```
E228 183C               pshy

E22A 18FEB8BC           ldy     NxtFireFlow
E22E CDA300             cpd     0,y
E231 2402               bhs     CheckVolume
E233 2013               bra     ReturnUnity
```

CheckVolume
```
'235 18FEB8BE           ldy     NxtFireVol
```

A17

CONFIDENTIAL

The Engineers Collaborative, Inc. 6     Cross Assembler V1.0

```
E239 FCB870            ldd    Integral
E23C CDA300            cpd    0,y
E23F 2402              bhs    ReturnZero
E241 2005              bra    ReturnUnity ReturnZero E243 CC0000            ldd    #0
E246 2005              bra    EndFireCheck ReturnUnity E248 CC0001            ldd    #1
E24B 2000              bra    EndFireCheck EndFireCheck E24D 1838              puly
E24F 39                rts
;*
;* SUBROUTINE  : GetNextFirePt
;* CALLED BY   : ValidFirePoint
;* ASSUMPTIONS : None
;* DESCRIPTION : Advances firing point array indicies to their
;*               next position. This routine is called after
;*               each solenoid firing.
;* REGISTERS   : Saved
;*

GetNextFirePt

E250 183C              pshy

E252 18FEB88C          ldy    NxtFireFlow
E256 1808              iny
E258 1808              iny
E25A 18FFB88C          sty    NxtFireFlow E25E 18FEB88E          ldy    NxtFireVol
E262 1808              iny
E264 1808              iny
E266 18FFB88E          sty    NxtFireVol E26A 1838              puly E26C 39                rts
;*
;* SUBROUTINE  : ValidFirePoint
;* CALLED BY   : ProcInspiration
;* ASSUMPTIONS : Flow/Volume firing point parameters have been met.
;* DESCRIPTION : We are at a valid firing point so fire the solenoid
;*               and advance pointers to the next flow/volume
;*               firing point information.
;* REGISTERS   : None
;*
```

A18

CONFIDENTIAL

The Engineers Collaborative, Inc. 68H.  ross Assembler V1.0

```
                ValidFirePoint

E260 BDE7F9             jsr     FireSolenoid
E270 BDE250             jsr     GetNextFirePt E273 39                 rts ;*
                ;* SUBROUTINE  : CheckThreshold
                ;* CALLED BY   : IdleLoop
                ;* ASSUMPTIONS : Value to be checked is at SmoothValue.
                ;* DESCRIPTION : Compare current value at SmoothValue with
                ;*               NoiseAmplitude constant, return zero if signal
                ;*               greater than or equal to noise and unity otherwise.
                ;* REGISTERS   : acca and accb are used.
                ;*

CheckThreshold

E274 FC884D             ldd     SmoothValue
E277 1A830064           cmpd    #NoiseAmplitude
E27B 2404               bhs     ClearAcc
E27D 8601               ldaa    #1
E27F 2001               bra     EndCheckThr ClearAcc
E281 4F                 clra EndCheckThr
E282 39                 rts ;*
                ;* SUBROUTINE  : NormalizeLstDir
                ;* CALLED BY   : ProcessBreath, ProcInspiration, ProcExpiration
                ;* ASSUMPIONS  : Value at LastDirection is zero or non-zero.
                ;* DESCRIPTION : In order to branch easily off of LastDirection,
                ;*               it is desirable to compare LastDirection to
                ;*               ExhaleSignBit or InhaleSignBit. In order to do
                ;*               this, LastDirection must be zero or unity. This
                ;*               routine does nothing if LastDirection is zero
                ;*               and changes it to unity if it is non-zero.
                ;* REGISTERS   : acca
                ;*

NormalizeLstDir

E283 B6884F             lda     LastDirection
E286 2702               beq     EndNormalize
E288 8601               ldaa    #1

EndNormalize

E28A B7884F             staa    LastDirection

E28D 39                 rts

;*
                ;* SUBROUTINE  : UpdateMaxValues
```

CONFIDENTIAL

The Engineers Collaborative, Inc. 68H    Cross Assembler V1.0

```
;*  CALLED BY   : ProcInspiration, ProcExpiration
;*  ASSUMPTIONS : New max value candidates are at CalValue and Integral
;*  DESCRIPTION : Updates flow and volume maxima.
;*  REGISTERS   : acca, accb
;*
        UpdateMaxValues E28E FC886A             ldd     CalValue
E291 1A8388B5           cmpd    MaxFlow
E295 2F03               ble     MaxIntegral
E297 FD88B5             std     MaxFlow MaxIntegral E29A FC8870             ldd     Integral
E29D 1A8388B7           cmpd    MaxVolume
E2A1 2F03               ble     EndUpdateMax
E2A3 FD88B7             std     MaxVolume EndUpdateMax E2A6 39                 rts ;*
;*  SUBROUTINE  : Hysteresis
;*  CALLED BY   : ProcInspiration, ProcExpiration
;*  ASSUMPTIONS : None
;*  DESCRIPTION : Acquires data points until signal down in the
;*              : noise band.
;*  REGISTERS   : acca, accb
;*
        Hysteresis E2A7 BDE34A             jsr     GetDataPoint
E2AA BDE603             jsr     UpdateToneValue
E2AD FCB84D             ldd     SmoothValue
E2B0 1A830064           cpd     #NoiseAmplitude
E2B4 24F1               bhs     Hysteresis E2B6 39                 rts ;           * * * * * * * * * * * * * * * * *
;           *   Peak Flow Meter Routines    *
;           * * * * * * * * * * * * * * * * *

;*
;*  SUBROUTINE  : DisplayAcuity
;*  CALLED BY   : ProcessBreath
;*  ASSUMPTIONS : Determine acuity index based on value in MaxFlow.
;*  DESCRIPTION : Value in MaxFlow is compared to the three acuity
;*              : index threshold constants. The appropriate single
;*              : LED is illuminated.
;*  REGISTERS   : acca, accb
;*
```

A20

CONFIDENTIAL

The Engineers Collaborative, Inc. 66    Cross Assembler V1.0

```
                DisplayAcuity

E2B7 BDE700             jsr     RedLedOff
E2BA BDE71D             jsr     GreenLedOff
E2BD BDE715             jsr     AmberLedOff E2C0 FC8885             ldd     MaxFlow E2C3 1AB3B8DE           cmpd    AcuityGreen
E2C7 2408               bhs     SignalGreen E2C9 1AB3B8E0           cmpd    AcuityAmber
E2CD 2407               bhs     SignalAmber E2CF 200A               bra     SignalRed SignalGreen E2D1 BDE719             jsr     GreenLedOn
E2D4 200A               bra     EndAcuity SignalAmber E2D6 BDE711             jsr     AmberLedOn
E2D9 2005               bra     EndAcuity SignalRed E2DB BDE709             jsr     RedLedOn
E2DE 2000               bra     EndAcuity EndAcuity
E2E0 39                 rts ;            * * * * * * * * * * * * * * *
        ;            * Flow Calibration Routines *
        ;            * * * * * * * * * * * * * * *

;*
        ;* SUBROUTINE  : HighCalBits
        ;* CALLED BY   : CalFlow
        ;* ASSUMPTIONS : Flow value in register D
        ;* DESCRIPTION : Calibration correction logic is based on the
        ;*               high bits (CalFieldLength) of the flow word.
        ;*               This routine returns these bits in accb.
        ;* REGISTERS   : acca, accb
        ;*

HighCalBits

E2E1 36                 psha
E2E2 8605               ldaa    #AbsWordLength-CalFieldLength
E2E4 B78867             staa    CalByte
E2E7 32                 pula
E2E8 0C                 clc DoubleRotate
```

A21

The Engineers Collaborative, Inc. 68\ Cross Assembler V1.0

```
                                        ; Create an rord instruction
                                        ; by doing an rora followed
                                        ; by an rorb
E2E9 46             rora
E2EA 56             rorb
E2EB 7A8867         dec     CalByte
E2EE 26F9           bne     DoubleRotate
E2F0 C40F           andb    #%00001111          ; Mask off any unexpected
                                                ; trash.

E2F2 39             rts
;*
;* SUBROUTINE  : CalFactor
;* CALLED BY   : CalFlow
;* ASSUMPTIONS : Flow vaue to be calibrated is in SmoothValue,
;*               correction factor is in CalByte.
;* DESCRIPTION : This integer routine multiplies smooth value by
;*               two (approximate correction to liters per minute)
;*               and then subtracts a fraction of the result from
;*               itself. This fraction is encoded in CalByte
;*               (see memory area at the end of code listing for
;*               description of the encoding). The result is
;*               returned in register D.
;* REGISTERS   : acca, accb
;*
            CalFactor
E2F3 4F             clra
E2F4 5F             clrb
E2F5 FD8868         std     CalWord E2F8 FCB840         ldd     SmoothValue
E2FB 7CB867         inc     CalByte             ; Allow early dec and check
                                                ; for zero E2FE 05             asld                        ; Multiply raw value by two E2FF 36             psha
E300 37             pshb E301 7A8867         dec     CalByte
E304 270A           beq     EndCalFactor CalRotate
E306 47             asra
E307 56             rorb
E308 7A8867         dec     CalByte
E30B 26F9           bne     CalRotate
E30D FD8868         std     CalWord EndCalFactor
E310 33             pulb
E311 32             pula
E312 B3B868         subd    CalWord             ; Calibrated flow =
                                                ; ((Original Flow)*2) -
                                                ; ((Original Flow)*2)*Fraction
                                                ; Where Fraction is encoded in
```

A22

The Engineers Collaborative, Inc. 68HL  Cross Assembler V1.0

```
                                                        ; CalByte
E315 39                 rts ;*
                ;* SUBROUTINE  : CalFlow
                ;* CALLED BY   : GetDataPoint
                ;* ASSUMPTIONS : Flow to be calibrated is at SmoothValue
                ;* DESCRIPTION : Raw A/D flow data is calibrated to liters
                ;*              per minute. The high CalFieldLength bits
                ;*              of the raw data word are used as arguments
                ;*              into a lookup table of correction factors.
                ;*              The calibrated result is placed in CalValue.
                ;* RESISTERS   : All saved
                ;*

CalFlow
E316 36                 psha
E317 37                 pshb
E318 183C               pshy E31A 7F8868             clr     CalWordHigh E31D FC884D             ldd     SmoothValue
E320 BDE2E1             jsr     HighCalBits E323 F78869             stab    CalWordLow
E326 CC8857             ldd     #CalTable
E329 F38868             addd    CalWord
E32C 188F               xgdy
E32E 18A600             ldaa    0,y
E331 878867             staa    CalByte         ; CalByte now contains right shift
                                                ; count for conversion factor
                                                ; calculation
E334 BDE2F3             jsr     CalFactor       ; Fine tune with calibration
                                                ; table
E337 FD886A             std     CalValue E33A 1838               puly
E33C 33                 pulb
E33D 32                 pula E33E 39                 rts ;               * * * * * * * * * * * * * * *
                ;               * Data Acquisition Routines *
                ;               * * * * * * * * * * * * * * *

;*
                ;* SUBROUTINE  : SetActiveFlag
                ;* CALLED BY   : IdleLoop
                ;* ASSUMPTIONS : None
                ;* DESCRIPTION : Sets the ActiveFlag. This flag is used to indicate
                ;*              that a breath is being processed. This also means
                ;*              that the tone is enabled. This information
                ;*              is used to avoid interrupt processing which would cause
                ;*              annoying clicking.
                ;* REGISTERS   : None
```

CONFIDENTIAL

The Engineers Collaborative, Inc. 68.   Cross Assembler V1.0

```
                    ;*
                    SetActiveFlag

E33F 7FB856             clr     ActiveFlag
E342 7CB856             inc     ActiveFlag
E345 39                 rts
                    ;*
                    ;* SUBROUTINE  : ClearActiveFlag
                    ;* CALLED BY   : IdleLoop
                    ;* ASSUMPTIONS : None
                    ;* DESCRIPTION : Clears the active flag
                    ;* REGISTERS   : None
                    ;*
                    ClearActiveFlag E346 7FB856             clr     ActiveFlag
E349 39                 rts ;*
                    ;* SUBROUTINE  : GetDataPoint
                    ;* CALLED BY   : IdleLoop, ProcInspiration, ProcExpiration, Hysteresis
                    ;* ASSUMPTIONS : An RTI will occur.
                    ;* DESCRIPTION : Polls for an RTI and then gets a data point from
                    ;*               the A/D. This signal is then conditioned by
                    ;*               (1) removing the low bits (2) Taking the absolute
                    ;*               value (3) low pass filtering. Numeric data display
                    ;*               is peformed here.
                    ;* REGISTERS   : acca
                    ;*
                    GetDataPoint E34A BDE4EB             jsr     WaitForRTI          ; 60 Hz sample rate
E34D BDE4F0             jsr     UpdateCounters      ; Update tic and second ctrs
E350 BDE37A             jsr     AcquireSignal       ; Get A/D data
E353 BDE437             jsr     TrimLowBits
E356 BDE44D             jsr     AbsoluteValue
E359 BDE460             jsr     LowPassFilter       ; Feed boxcar E35C FCB84D             ldd     SmoothValue         ; Compute calibrated flow
E35F FDB834             std     SampleValue         ; from filtered data
E362 BDE316             jsr     CalFlow
E365 BDE384             jsr     Integrate E368 B62001             ldaa    LogFlag
E36B 2706               beq     SkipLog
E36D FCB86A             ldd     CalValue
E370 BDE59D             jsr     LogDataPoint SkipLog E373 FCB88A             ldd     ShotCounter
E376 BDE634             jsr     DisplayData
                ;       ldd     CalValue            ; Preferred place for
                ;       jsr     DisplayData         ; data display during
                ;       ldd     Integral            ; debugging.
```

The Engineers Collaborative, Inc. 68i. Cross Assembler V1.0

```
                ;       jsr     DisplayData
E379 39                 rts

;*
                ;* SUBROUTINE  : AcquireSignal
                ;* CALLED BY   : GetDataPoint
                ;* ASSUMPTIONS : x points to register base.
                ;* DESCRIPTION : Gets a data point from the A/D, stores it at SampleValue,
                ;*               and clears the RTI to allow another polling cycle.
                ;* REGISTERS   : None
                ;*
                AcquireSignal E37A 8DE6C1             jsr     GetSignal E37D FD8834             std     SampleValue E380 1D258F             bclr    tflg2,x RTIFlagClr E383 39                 rts ;                * * * * * * * * * * * * * * *
                ;                * Flow Integration Routines *
                ;                * * * * * * * * * * * * * * *

;*
                ;* SUBROUTINE  : Integrate
                ;* CALLED BY   : GetDataPoint
                ;* ASSUMPTIONS : None
                ;* DESCRIPTION : Full description of integration algorithm is
                ;*               given in the data definition area. This routine
                ;*               performs integration if the IntegrateFlag is true
                ;*               and returns the result in Integral.
                ;* REGISTERS   : All saved
                ;*
                Integrate
E384 36                 psha
E385 37                 pshb
E386 183C               pshy E388 B68876             ldaa    IntegrateFlag
E38B 2745               beq     EndIntegrate E38D FC8872             ldd     IntegralTicCnt
E390 830001             subd    #1
E393 FD8872             std     IntegralTicCnt
E396 2603               bne     Integrate1
E398 8DE3D7             jsr     StopIntegration Integrate1

E39B FC886A             ldd     CalValue
E39E F3886E             addd    TicSum
E3A1 FD886E             std     TicSum
```

A25

CONFIDENTIAL

The Engineers Collaborative, Inc. 68     Cross Assembler V1.0

```
E3A4 7A8874            dec     GroupTicCnt
E3A7 2614              bne     Integrate2
E3A9 BDE407            jsr     ComputeAverage
E3AC F3886C            addd    RunningSum
E3AF FD886C            std     RunningSum
E3B2 8604              ldaa    #TicGroup
E3B4 878874            staa    GroupTicCnt
E3B7 CC0000            ldd     #$0000
E3BA FD886E            std     TicSum Integrate2

E3BD 7A8875            dec     UpdateCount
E3C0 2610              bne     EndIntegrate
E3C2 BDE41B            jsr     ComputeIntegral
E3C5 47                asra                            ; fudge factor = 1/2
E3C6 56                rorb
E3C7 F38870            addd    Integral
E3CA FD8870            std     Integral
E3CD 8614              ldaa    #UpdateTics
E3CF 878875            staa    UpdateCount EndIntegrate E3D2 1838              puly
E3D4 33                pulb
E3D5 32                pula E3D6 39                rts StopIntegration E3D7 BDE403            jsr     IntegrateOff E3DA 39                rts
                ;*
                ;* SUBROUTINE : IntegrateOn
                ;* CALLED BY  : IdleLoop
                ;* ASSUMPTIONS: None
                ;* DESCRIPTION: Initializes all variables used by the integrator.
                ;* REGISTERS  : All saved.
                ;*

IntegrateOn

E3DB 36                psha
E3DC 37                pshb

E3DD 4F                clra
E3DE 5F                clrb

E3DF FD886C            std     RunningSum
E3E2 FD886E            std     TicSum
E3E5 FD8870            std     Integral E3E8 CC00F0            ldd     #IntegralTics
E3EB FD8872            std     IntegralTicCnt
```

A26

The Engineers Collaborative, Inc. &    Cross Assembler V1.0

```
E3EE 7F8876              clr     IntegrateFlag
E3F1 7C8876              inc     IntegrateFlag E3F4 8614                ldaa    #UpdateTics
E3F6 B78875              staa    UpdateCount E3F9 8604                ldaa    #TicGroup
E3FB B78874              staa    GroupTicCnt E3FE 9600                ldaa E400 33                  pulb
E401 32                  pula E402 39                  rts
```

```
;*
;* SUBROUTINE  : IntegrateOff
;* CALLED BY   : IdleLoop
;* ASSUMPTIONS : None
;* DESCRIPTION : Clears the integration flag.
;* REGISTERS   : None.
;*
```

IntegrateOff

```
E403 7F8876              clr     IntegrateFlag
E406 39                  rts
```

```
;*
;* SUBROUTINE  : ComputeAverage
;* CALLED BY   : Integrate
;* ASSUMPTIONS : LogTicGroup elements have been added into TicSum.
;* DESCRIPTION : Computes the average of the LogTicGroup elements
;*               added into TicSum.
;* REGISTERS   : Registers acca, accb and y are used
;*
```

ComputeAverage

```
E407 FCB86E              ldd     TicSum
E40A 847F                anda    #%01111111    ; Clear sign bit prior to asra
E40C 18CE0002            ldy     #LogTicGroup
E410 1808                iny
```

AverageLoop

```
E412 1809                dey
E414 2704                beq     EndAverage

E416 47                  asra
E417 56                  rorb

E418 20F8                bra     AverageLoop
```

EndAverage

```
E41A 39                  rts
```

A27

The Engineers Collaborative, Inc. 68¦  ross Assembler V1.0

```
;*
;* SUBROUTINE  : ComputeIntegral
;* CALLED BY   : Integrate
;* ASSUMPTIONS : RunningSum ready for division by constant.
;* DESCRIPTION : Divides RunningSum by the appropriate
;*               calibration constant, represented as
;*               LogFlowConvert, thus allowing division
;*               via right shift operations.
;* REGISTERS   : acca, accb, y
;*

ComputeIntegral

E41B FCB86C            ldd    RunningSum
E41E 847F              anda   #%01111111         ; Clear sign bit
E420 18CE000A          ldy    #LogFlowConvert
E424 1808              iny IntegralLoop E426 1809              dey
E428 2704              beq    EndDivide
E42A 47                asra
E42B 56                rorb
E42C 20F8              bra    IntegralLoop EndDivide 42E 18CE0000          ldy    #$0000
E432 18FFB86C          sty    RunningSum EndCompute E436 39                rts ;                      * * * * * * * * * * * * * * * * * *
;                      * Raw Data Manipulation Routines  *
;                      * * * * * * * * * * * * * * * * * *

;*
;* SUBROUTINE  : TrimLowBits
;* CALLED BY   : GetDataPoint
;* ASSUMPTIONS : None.
;* DESCRIPTION : Right shifts away Trimbits lsb's from the
;*               16 bit SampleValue and stores the result at
;*               SampleValue.
;* REGISTERS   : All saved.
;*

TrimLowBits

E437 183C              pshy

E439 FCB834            ldd    SampleValue
E43C 18CE0002          ldy    #TrimBits
               TrimBit
 440 0C                clc
```

A28

CONFIDENTIAL

The Engineers Collaborative, Inc. 6.   .1 Cross Assembler V1.0

```
E441 46                 rora
E442 56                 rorb
E443 1809               dey
E445 26F9               bne     TrimBit E447 FD8834             std     SampleValue E44A 1838               puly E44C 39                 rts ;*
                ;* SUBROUTINE  : AbsoluteValue
                ;* CALLED BY   : GetDataPoint
                ;* DESCRIPTION : Binary number of with non-extended sign bit
                ;*                at SignBitMask is in register D.
                ;* DESCRIPTION : Form absolute value by (1) Doing nothing
                ;*                if number already positive (2) Clearing
                ;*                sign bit and subtracting from largest
                ;*                positive value if sign bit set. The information
                ;*                contained in the sign bit (ie. flow direction)
                ;*                is stored away in LastDirection.
                ;* REGISTERS   : All saved.
                ;*
                AbsoluteValue E44D 36                 psha
E44E 37                 pshb E44F FC8834             ldd     SampleValue
E452 8402               anda    #SignBitMask
E454 87B84F             staa    LastDirection   ; Zero if sign bit clear,
                                                ; equal to SignBitMask if
                                                ; sign bit set
E457 2711               beq     EndAbsValue
E459 FC8834             ldd     SampleValue
E45C 8401               anda    #SignBitClr
E45E FD8838             std     AbsScratch
E461 CC0200             ldd     #MaxValue       ; Do a 16 bit subtract instead
                                                ; of a 16 bit complement
                                                ; because number is not two's
                                                ; complement
E464 B38838             subd    AbsScratch
E467 FD8834             std     SampleValue EndAbsValue E46A 33                 pulb
E46B 32                 pula E46C 39                 rts
```

;                       * * * * * * * * * * * * * *
;                       * Digital Filter Routines *
;                       * * * * * * * * * * * * * *

A29

CONFIDENTIAL

The Engineers Collaborative, Inc. 68HC_ _ross Assembler V1.0

```
;*
;* SUBROUTINE  : LowPassFilter
;* CALLED BY   : GetDataPoint
;* ASSUMPTIONS : None.
;* DESCRIPTION : Places the new SampleValue in a ring buffer
;*                and averages the contents of the buffer,
;*                returning the result in SmoothValue.
;* REGISTERS   : All saved.
;*
            LowPassFilter E46D 36                 psha
E46E 37                 pshb
E46F 183C               pshy E471 CCB83A             ldd     #Filter
E474 F3B84A             addd    FilterIndex16
E477 BDE48A             jsr     BumpFilterIndex
E47A 188F               xgdy
E47C FCB834             ldd     SampleValue
E47F 18ED00             std     0,y
E482 BDE4AA             jsr     ProcessFilter E485 1838               puly
E487 33                 pulb
E488 32                 pula E489 39                 rts
;*
;* SUBROUTINE  : BumpFilterIndex
;* CALLED BY   : LowPassFilter
;* ASSUMPTIONS : None
;* DESCRIPTION : Modulo FilterLength increment routine.
;* REGISTERS   : All saved.
;*
            BumpFilterIndex E48A 36                 psha
E48B B6B848             ldaa    FilterIndex
E48E 4C                 inca
E48F 4C                 inca
E490 8110               cmpa    #FilterLength*2
E492 2601               bne     EndBumpFilter
E494 4F                 clra EndBumpFilter E495 B7B848             staa    FilterIndex
E498 32                 pula E499 39                 rts
;*
;* SUBROUTINE  : DivideByLength
;* CALLED BY   : ProcessFilter
```

A30

CONFIDENTIAL

The Engineers Collaborative, Inc. 6E    Cross Assembler V1.0

```
                ;*  ASSUMPTIONS : None.
                ;*  DESCRIPTION  : Performs integer divide of 16 bit quantity in D.
                ;*  REGISTERS    : All saved
                ;*
                DivideByLength E49A 183C               pshy E49C 18CE0003           ldy     #LogLength
                divide
E4A0 0C                 clc
E4A1 46                 rora
E4A2 56                 rorb
E4A3 1809               dey
E4A5 26F9               bne     divide E4A7 1838               puly E4A9 39                 rts ;*
                ;*  SUBROUTINE  : ProcessFilter
                ;*  CALLED BY   : LowPassFilter
                ;*  ASSUMPTIONS : None.
                ;*  DESCRIPTION : Average elements in the boxcar filter and
                ;*                return the result in location SmoothValue.
                ;*  REGISTERS   : All saved.
                ;*
                ProcessFilter E4AA 36                 psha
E4AB 37                 pshb
E4AC 183C               pshy E4AE 18CEB83A           ldy     #Filter
E4B2 8608               lda     #FilterLength
E4B4 87B84C             staa    FilterCounter
E4B7 4F                 clra
E4B8 5F                 clrb AddNextElement E4B9 18E300             addd    0,y
E4BC 1808               iny
E4BE 1808               iny
E4C0 7AB84C             dec     FilterCounter
E4C3 2702               beq     EndProcFilter
E4C5 20F2               bra     AddNextElement EndProcFilter E4C7 BDE49A             jsr     DivideByLength
E4CA FDB840             std     SmoothValue E4CD 1838               puly
E4CF 33                 pulb
```

- A31

CONFIDENTIAL

The Engineers Collaborative, Inc. 68HL. Cross Assembler V1.0

```
.D0 32                  pula

E4D1 39                 rts

;*
                ;* SUBROUTINE  : ClearBoxCar
                ;* CALLED BY   : Power On Reset
                ;* ASSUMPTIONS : None
                ;* DESCRIPTION : Clears all of the elements in the boxcar filter
                ;* REGISTERS   : All saved.
                ;*

ClearBoxCar

E4D2 183C               pshy
E4D4 36                 psha

E4D5 8608               ldaa    #FilterLength
E4D7 18CEB83A           ldy     #Filter
E4DB 8DE4E2             jsr     ClearLoop E4DE 32                 pula
E4DF 1838               puly E4E1 39                 rts ;*
                ;* SUBROUTINE  : ClearLoop
                ;* CALLED BY   : ClearBoxCar
                ;* ASSUMPTIONS : Y points to first byte in array to be cleared. A
                ;*               contains the length of the array.
                ;* DESCRIPTION : Zero the elements in the array.
                ;* REGISTERS   : acca, y
                ;*

ClearLoop
E4E2 186F00             clr     0,y
E4E5 4A                 deca
E4E6 1808               iny
E4E8 2AF8               bpl     ClearLoop E4EA 39                 rts ;               * * * * * * * * * * *
                ;               *  Polling Routines  *
                ;               * * * * * * * * * * *

;*
                ;* SUBROUTINE  : WaitForRTI
                ;* CALLED BY   : GetDataPoint
                ;* ASSUMPTIONS : (1) An RTI will occur (or will hang forever).
                ;*               (2) x points to register base.
                ;* DESCRIPTION : Waits for real time interrupt.
                ;* REGISTERS   : None
                ;*

WaitForRTI
```

A32

CONFIDENTIAL

The Engineers Collaborative, Inc. 6    Cross Assembler V1.0

```
E4EB 1F2540FC          brclr   tflg2,x RTIFlag 5
E4EF 39                rts

;               * * * * * * * * * * * * * * *
                ;               * HC11 Timekeeping Routines *
                ;               * * * * * * * * * * * * * * *

;*
                ;* SUBROUTINE  : UpdateCounters
                ;* CALLED BY   : GetDataPoint
                ;* ASSUMPTIONS : None.
                ;* DESCRIPTION : Manage the counters used for integration and
                ;*               general timekeeping.
                ;* REGISTERS   : All saved.
                ;*

UpdateCounters

E4F0 36                psha
E4F1 183C              pshy

E4F3 18FE8872          ldy     IntegralTicCnt
E4F7 1808              iny
E4F9 18FF8872          sty     IntegralTicCnt E4FD B68836            ldaa    TicCounter
E500 4C                inca
E501 813C              cmpa    #MaxTics
E503 2604              bne     EndUpdateCtr
E505 7C8837            inc     SecondsCntr
E508 4F                clra EndUpdateCtr E509 B78836            staa    TicCounter E50C 1838              puly
E50E 32                pula E50F 39                rts ;               * * * * * * * * * * * * *
                ;               * Alarm Clock Routines *
                ;               * * * * * * * * * * * * *

;*
                ;* SUBROUTINE  : CheckAlarm
                ;* CALLED BY   : IdleLoop
                ;* ASSUMPTIONS : None
                ;* DESCRIPTION : If we are inactive, read the time and check
                ;*               hours against the list of alarm clock settings.
                ;*               Sound alarm clock if time matches an entry
                ;*               in the list. Only alarm once per programmed hour.
                ;* REGISTERS   : All saved.
                ;*

CheckAlarm
```

The Engineers Collaborative, Inc. 68H.. .ross Assembler V1.0

```
E510 36                 psha
E511 37                 pshb
E512 183C               pshy E514 B68856             ldaa    ActiveFlag
E517 2633               bne     EndCheckAlarm E519 B68810             ldaa    AlarmCounter
E51C 2705               beq     ReadClock
E51E BDE568             jsr     ServiceDuration
E521 2029               bra     EndCheckAlarm ReadClock E523 B68836             ldaa    TicCounter
E526 2624               bne     EndCheckAlarm E528 BDE78D             jsr     ReceiveClockBits
E52B B688AD             ldaa    HoursDta
E52E 18CEB813           ldy     #AlarmTime
E532 F68811             ldab    NumAlarms CheckNextTime E535 B18812             cmpa    LastAlarm
E538 2705               beq     SkipCompare E53A 18A100             cmpa    0,y
E53D 2707               beq     TimeToBeep SkipCompare E53F 1808               iny
E541 5A                 decb
E542 2708               beq     EndCheckAlarm
E544 20EF               bra     CheckNextTime TimeToBeep E546 B7B812             staa    LastAlarm
E549 BDE551             jsr     SoundAlarm EndCheckAlarm E54C 1838               puly
E54E 33                 pulb
E54F 32                 pula E550 39                 rts ;*
;* SUBROUTINE  : SoundAlarm
;* CALLED BY   : CheckAlarm
;* ASSUMPTIONS : None.
;* DESCRIPTION : Sound alarm and increment the AlarmCounter.
;*               This counter keeps track of how long
;*               the alarm remains on.
```

A34

CONFIDENTIAL

The Engineers Collaborative, Inc. 68    Cross Assembler V1.0

```
                    ;* REGISTERS  : None.
                    ;*

SoundAlarm

E551 BDE558                 jsr     AlarmOn
E554 7C8810                 inc     AlarmCounter E557 39                     rts ;*
                    ;* SUBROUTINE  : AlarmOn
                    ;* CALLED BY   : SoundAlarm
                    ;* ASSUMPTIONS : None.
                    ;* DESCRIPTION : Creates tone with period stored in AlarmTone.
                    ;* REGISTERS   : Saved.
                    ;*

AlarmOn
E558 36                     psha

E559 B68800                 ldaa    AlarmTone
E55C B78800                 staa    ToneValue
E55F BDE620                 jsr     EnableTone E562 32                     pula E563 39                     rts ;*
                    ;* SUBROUTINE  : AlarmOff
                    ;* CALLED BY   : ServiceDuration
                    ;* ASSUMPTIONS : System inactive, alarm is sounding.
                    ;* DESCRIPTION : Turns off speaker.
                    ;* REGISTERS   : None.

AlarmOff
E564 BDE62D                 jsr     DisableTone

E567 39                     rts

;*
                    ;* SUBROUTINE  : ServiceDuration
                    ;* CALLED BY   : CheckAlarm
                    ;* ASSUMPTIONS : Alarm is sounding, duration timer value is passed
                    ;*               in acca.
                    ;* DESCRIPTION : Checks to see if alarm has sounded long enough,
                    ;*               updates alarm duration timer.
                    ;* REGISTERS   : acca
                    ;*

ServiceDuration

E568 4C                     inca
E569 B1880F                 cmpa    AlarmDuration
E56C 2604                   bne     EndSrvDuration
E56E 4F                     clra
 56F BDE564                 jsr     AlarmOff
```

CONFIDENTIAL

The Engineers Collaborative, Inc. 68' `ross Assembler V1.0

```
                EndSrvOuration

E572 B7B810         staa    AlarmCounter

E575 39             rts

;               * * * * * * * * * * * * * *
            ;               * Initialization Routines *
            ;               * * * * * * * * * * * * * *
            ;*
            ;* SUBROUTINE  : ConfigRTI
            ;* CALLEN BY   : Power On Reset
            ;* ASSUMPTIONS : x points to register base.
            ;* DESCRIPTION : Sets up for RTI to occur at the specified interval.
            ;* REGISTERS   : None.
            ;*
                ConfigRTI E576 1C2602         bset    pactl,x SixtyHertzRTI
E579 1C2440         bset    tmsk2,x EnableRTI E57C 39             rts ;*
            ;* SUBROUTINE  : ClearTimerRegs
            ;* CALLED BY   : Power On Reset
            ;* ASSUMPTIONS : x points to register base.
            ;* DESCRIPTION : Clear all timer control and mask registers.
            ;* REGISTERS   : None.
            ;*
                ClearTimerRegs E57D 6F20           clr     tctl1,x
E57F 6F21           clr     tctl2,x
E581 6F22           clr     tmsk1,x
E583 6F24           clr     tmsk2,x
E585 6F26           clr     pactl,x E587 39             rts ;*
            ;* SUBROUTINE  : ConfigWaveTimer
            ;* CALLED BY   : Power On Reset
            ;* ASSUMPTIONS : (1) x points to register base
            ;*               (2) Called within 64 cycles after reset.
            ;* DESCRIPTION : Configure timer pre-scaler, disable timer interrupts
            ;*               for now.
            ;* REGISTERS   : None
            ;*
                ConfigWaveTimer E588 1C2401         bset    tmsk2,x SpeedCntrl
E58B 1D24B0         bclr    tmsk2,x TimerIntConfig
```

The Engineers Collaborative, Inc. 68HC..ross Assembler V1.0

```
E58E 39              rts
                ;         * * * * * * * * * * * * * * * * *
                ;         * Binary->BCD Conversion Routines *
                ;         * * * * * * * * * * * * * * * * *
                ;
                ;* SUBROUTINE : BinaryToBCD
                ;* CALLED BY  : LogDataPoint, DisplayData
                ;* ASSUMPTIONS: Binary value in D, result will be placed at BCDResult.
                ;* DESCRIPTION: Table driven binary->BCD routine. WordLength bits in
                ;*              passed argument are examined. Appropriate BCD power-of-two
                ;*              values are accumulated into the result sum using
                ;*              HC11 supported BCD addition.
                ;* REGISTERS  : acca,accb,y BinaryToBCD E58F 36              psha E590 860E            ldaa   #WordLength
E592 B78897          staa   BCDConvCtr
E595 18CEB879        ldy    #BCDTable
E599 7FB899          clr    BCDResultHigh
E59C 7FB898          clr    BCDResultLow E59F 32              pula BCDLoop E5A0 0C              clc
E5A1 46              rora
E5A2 56              rorb               ; Net effect is rord since
                                        ; rorb affects carry and
                                        ; carry is in turn fed into
                                        ; acca from left with rora
E5A3 250B            bcs    AddBCDValue
E5A5 7AB897          dec    BCDConvCtr
E5A8 2727            beq    BCDConvDone
E5AA 1808            iny
E5AC 1808            iny
E5AE 20F0            bra    BCDLoop AddBCDValue E5B0 36              psha
E5B1 B6B898          ldaa   BCDResultLow
E5B4 18AB00          adda   0,y
E5B7 19              daa
E5B8 1808            iny
E5BA B7B898          staa   BCDResultLow
E5BD B6B899          ldaa   BCDResultHigh
E5C0 2403            bcc    SkipCarry
E5C2 8B01            adda   #1
E5C4 19              daa SkipCarry
```

A37

CONFIDENTIAL

The Engineers Collaborative, Inc. 68? Cross Assembler V1.0

```
E5C5 18A800            adda    0,y
E5C8 19                daa
E5C9 B7B899            staa    BCDResultHigh
E5CC 1808              iny
E5CE 32                pula
E5CF 20CF              bra     BCDLoop BCDConvDone E5D1 39                rts ;*
;* SUBROUTINE  : BCDToAscii
;* CALLED BY   : DisplayData
;* ASSUMPTIONS : BCDSourcePtr and AsciiDestPtr have been loaded.
;* DESCRIPTION : Appropriate BCD->ASCII conversion bits are masked
;*               into the high and low BCD digits.
;* REGISTERS   : All saved.
;*

BCDToAscii

E5D2 3C                pshx
E5D3 183C              pshy
E5D5 36                psha
E5D6 37                pshb E5D7 C602              ldb     #HalfDisplayLen
 5D9 18FEB895          ldy     BCDSourcePtr
 5DD FEB803            ldx     AsciiDestPtr NextBCDPair E5E0 18A600            ldaa    0,y
E5E3 840F              anda    #%00001111
E5E5 8A10              oraa    #AsciiMask
E5E7 A700              staa    0,x
E5E9 08                inx
E5EA 18A600            ldaa    0,y
E5ED 44                lsra
E5EE 44                lsra
E5EF 44                lsra
E5F0 44                lsra
E5F1 8A10              oraa    #AsciiMask
E5F3 A700              staa    0,x
E5F5 5A                decb
E5F6 2705              beq     EndBCDToAscii E5F8 08                inx
E5F9 1808              iny
E5FB 20E3              bra     NextBCDPair EndBCDToAscii E5FD 33                pulb
E5FE 32                pula
 5FF 1838              puly
```

A38

CONFIDENTIAL

The Engineers Collaborative, Inc. 68H    ross Assembler V1.0

```
E601 38                pulx

E602 39                rts

;           * * * * * * * * * * * * * * *
              ;           * Tone Generation Routines  *
              ;           * * * * * * * * * * * * * * *
              ;*
              ;* SUBROUTINE : UpdateToneValue
              ;* CALLED BY  : ProcInspiration, ProcExpiration, Hysteresis
              ;* ASSUMPTIONS: SampleValue has been right shifted by TrimBits.
              ;* DESCRIPTION: Replaces the removed TrimBits removed from
              ;*              SampleValue with zeros and stores the result
              ;*              at ToneValue.
              ;* REGISTERS  : All saved.
              ;*

UpdateToneValue

E603 36                psha
E604 37                pshb
E605 183C              pshy E607 FCB840            ldd    SmoothValue
E60A 18CE0002          ldy    #TrimBits
E60E 0C                clc LeftShift E60F 59                rolb
E610 49                rola
E611 1809              dey
E613 26FA              bne    LeftShift E615 C30100            addd   #ToneOffset
E618 FD8800            std    ToneValue E61B 1838              puly
E61D 33                pulb
E61E 32                pula E61F 39                rts ;*
              ;* SUBROUTINE : EnableTone
              ;* CALLED BY  : ProcInspiration, ProcExpiration
              ;* ASSUMPTIONS: x points to register base.
              ;* DESCRIPTION: Set up timer four to allow output compare pin
              ;*              activation of speaker.
              ;* REGISTERS  : None
              ;*

EnableTone

E620 1D23EF            bclr   tflg1,x ToneFlgClr
E623 1C2210            bset   tmsk1,x ToneInt
```

A35

The Engineers Collaborative, Inc. 68! ross Assembler V1.0

```
E626 1C2004              bset    tctl1,x ToggleToneSet
E629 1D2008              bclr    tctl1,x ToggleToneClr E62C 39                  rts
```

```
;*
;* SUBROUTINE  : DisableTone
;* CALLED BY   : ProcInspiration, ProcExpiration
;* ASSUMPTIONS : x points to register base.
;* DESCRIPTION : Disables output compare pin toggle. Also ensures
;*               that output pin is left in the off state. (If output
;*               pin not specifically disabled in this fashion,
;*               speaker can be be driven high continuously).
;* REGISTERS   : None.
;*
        DisableTone
```

```
E62D 1D2004              bclr    tctl1,x ToggleToneSet
E630 1D0010              bclr    porta,x speaker E633 39                  rts
```

```
;               * * * * * * * * * * * * * * * * *
;               * LED Character Display Routines *
;               * * * * * * * * * * * * * * * * *

;*
;* SUBROUTINE  : DisplayData
;* CALLED BY   : GetDataPoint
;* ASSUMPTIONS : (binary) data to be displayed is passed in register D.
;* DESCRIPTION : Converts passed binary value to BCD and displays result.
;* REGISTERS   : Saved.
;*
        DisplayData
```

```
E634 36                  psha
E635 37                  pshb

E636 BDE58F              jsr     BinaryToBCD

E639 CCB898              ldd     #BCDResult
E63C FDB895              std     BCDSourcePtr
E63F CCB805              ldd     #AsciiString
E642 FDB803              std     AsciiDestPtr E645 BDE5D2              jsr     BCDToAscii E648 18CEB805            ldy     #AsciiString E64C BDE652              jsr     DisplayString E64F 33                  pulb
E650 32                  pula E651 39                  rts
```

A40

CONFIDENTIAL

The Engineers Collaborative, Inc. 68.    Cross Assembler V1.0

```
         ;*
         ;* SUBROUTINE  : DisplayString
         ;* CALLED BY   : DisplayData
         ;* ASSUMPTIONS : DisplayLength character string pointed to by y
         ;* DESCRIPTION : Send DisplayLength characters to display device.
         ;* REGISTERS   : Saved.
         ;*

DisplayString

E652 36           psha
E653 37           pshb

E654 8600         ldaa   #0

DispNxtChar

E656 18E600       ldab   0,y
E659 F7B802       stab   DisplayByte
E65C 36           psha
E65D BDE670       jsr    DisplayCharSel
E660 BDE695       jsr    SendDisplayByte
E663 32           pula
E664 1808         iny
E666 4C           inca
E667 8104         cmpa   #DisplayLength
E669 2702         beq    EndDispString
E66B 20E9         bra    DispNxtChar EndDispString E66D 33           pulb
E66E 32           pula E66F 39           rts ;*
         ;* SUBROUTINE  : DisplayCharSel
         ;* CALLED BY   : DisplayString
         ;* ASSUMPTIONS : (1) Display character index is in acca
         ;*               (2) Next ascii character to be displayed is at DisplayByte
         ;* DESCRIPTION : Masks in character index to ascii character for display
         ;*               at appropriate position on display device.  Result
         ;*               is (destructively) stored at DisplayByte.
         ;* REGISTERS   : Saved (argument DisplayByte is modified).
         ;*

DisplayCharSel

E670 183C         pshy
E672 37           pshb

E673 18CE0000     ldy    #$0000

E677 48           asla
E678 48           asla
E679 48           asla
```

The Engineers Collaborative, Inc. 68    Cross Assembler V1.0

```
E67A 48                asla
E67B 48                asla

E67C F68802            ldab    DisplayByte
E67F C41F              andb    #CharAddrMask
E681 F7B802            stab    DisplayByte E684 BAB802            ora     DisplayByte
E687 B7B802            staa    DisplayByte E68A 33                pulb
E68B 1838              puly E68D 39                rts ;*
;* SUBROUTINE  : DisplayCycle
;* CALLED BY   : SendDisplayByte
;* ASSUMPTIONS : No delay bewteen assert and de-assert required.
;* DESCRIPTION : Assert and de-assert display device select line.
;*               Sequence executed as fast as possible.
;* REGISTERS   : None.
;*

DisplayCycle

E68E BDE6A1            jsr     DisplaySelect
E691 BDE6A5            jsr     DisplayDeSelect E694 39                rts ;*
;* SUBROUTINE  : SendDisplayByte
;* CALLED BY   : DisplayString
;* ASSUMPTIONS : Displayable character (with hardware specific
;*               indexing info) is at DisplayByte.
;* DESCRIPTION : Send character at DisplayByte to display device.
;* REGISTERS   : Saved.
;*

SendDisplayByte

E695 36                psha
E696 B68802            ldaa    DisplayByte
E699 BDE680            jsr     SendSpiByte
E69C BDE68E            jsr     DisplayCycle
E69F 32                pula E6A0 39                rts ;*
;* SUBROUTINE  : DisplaySelect
;* CALLED BY   : DisplayCycle
;* ASSUMPTIONS : (1) x points to register base
;*               (2) Display select line is active low.
;* DESCRIPTION : Select display.
;* REGISTERS   : None.
;*
```

The Engineers Collaborative, Inc. 68H.  .ross Assembler V1.0

```
                DisplaySelect

E6A1 1D0820             bclr    portd,x DispSelPin
E6A4 39                 rts

;*
                ;* SUBROUTINE  : DisplayDeSelect
                ;* CALLED BY   : DisplayCycle
                ;* ASSUMPTIONS : (1) x points to register base
                ;*              (2) Display select line is active low.
                ;* DESCRIPTION : De-select display.
                ;* REGISTERS   : None.
                ;*

DisplayDeSelect

E6A5 1C0820             bset    portd,x DispSelPin
E6A8 39                 rts

;                * * * * * * * * *
                ;                * SPI Routines *
                ;                * * * * * * * * *

;*
                ;* SUBROUTINE  : ActivateSPI
                ;* CALLED BY   : Power On Reset
                ;* ASSUMPTIONS : x points to register base.
                ;* DESCRIPTION : Set up spcr for SPI
                ;* REGISTERS   : Saved.
                ;*

ActivateSPI

E6A9 36                 psha

E6AA 8653               ldaa    #SpiControlMsk
E6AC A728               staa    spcr,x E6AE 32                 pula E6AF 39                 rts ;*
                ;* SUBROUTINE  : SendSpiByte
                ;* CALLED BY   : GetSignal, SendDisplayByte
                ;* ASSUMPTIONS : (1) Byte to be sent is in acca.
                ;*              (2) x points to register base.
                ;* DESCRIPTION : Sends byte over SPI, waits for send to complete
                ;*              and performs dummy read of spsr.
                ;* REGISTERS   : acca
                ;*

SendSpiByte

E6B0 A72A               staa    spdr,x
                SpiWait
 B2 1F2980FC            brclr   spsr,x %10000000 SpiWait
```

A43

CONFIDENTIAL

The Engineers Collaborative, Inc. 68x Cross Assembler V1.0

```
E686 A629            ldaa     spsr,x

E688 39              rts

;           * * * * * * * * * * *
                ;           * A/D Access Routines *
                ;           * * * * * * * * * * *

;*
                ;* SUBROUTINE : ADWait
                ;* CALLED BY  : GetSignal
                ;* ASSUMPTIONS: x points to register base.
                ;* DESCRIPTION: LTC1290 does not have a conversion-ready line.
                ;*              Therefore need to unilaterally wait before
                ;*              expecting valid A/D result. This routine is a
                ;*              simple timing loop (could be made more efficient
                ;*              through use of interrupt driven timers).
                ;* REGISTERS  : Saved.
                ;*
                        ADWait
E689 36                 psha E68A 8632               ldaa    #ConvertDelay WaitLonger
E68C 4A                 deca
E68D 2AFD               bpl     WaitLonger E68F 32                 pula
E6C0 39                 rts ;*
                ;* SUBROUTINE : GetSignal
                ;* CALLED BY  : AcquireSignal
                ;* ASSUMPTIONS: None
                ;* DESCRIPTION: Activates analog to digital convertor and obtains a
                ;*              single digitized value. Routine is NOT interrupt driven.
                ;*              Value is returned as a (sign extended) twos complement number
                ;*              in the double accumulator (register D).
                ;*
                ;*              Bit pattern for A/D (LTC1290) control:
                ;*              0:1 => Word length (00=8 bits, 01=sleep, 10=12 bits, 11=16 bits)
                ;*              2:2 => MSB First when true
                ;*              3:3 => Bipolar when false
                ;*              6:4 => Channel select
                ;*              7:7 => Single ended when true
                ;*
                ;* REGISTERS  : acca ,accb.
                ;*
                        GetSignal
E6C1 BDE701             jsr     SelectAD
E6C4 8684               ldaa    #%10000100           ; Request 8 bit value,
E6C6 BDE680             jsr     SendSpiByte
E6C9 BDE705             jsr     DeSelectAD
E6CC BDE689             jsr     ADWait               ; Wait for conversion
```

A44

CONFIDENTIAL

The Engineers Collaborative, Inc. 68H    ross Assembler V1.0

```
E6CF 8DE701              jsr     SelectAD
E6D2 8687                ldaa    #%10000111        ; Request 16 bit value
                                                   ; (actually two 8 bit
                                                   ; values)
E6D4 8DE680              jsr     SendSpiByte
E6D7 A62A                ldaa    spdr,x            ; Grab high byte
E6D9 36                  psha
E6DA 8684                ldaa    #%10000100        ; Request 8 bit value
E6DC 8DE680              jsr     SendSpiByte
E6DF A62A                ldaa    spdr,x            ; Grab low byte
E6E1 16                  tab
E6E2 32                  pula                      ; Result now in D left
                                                   ; shifted by four bits
E6E3 8DE705              jsr     DeSelectAD
E6E6 04                  lsrd                      ; No sign extend right
E6E7 04                  lsrd                      ; shift available, so
E6E8 04                  lsrd                      ; right shift four times
E6E9 04                  lsrd                      ; pumping in zeros
E6EA 36                  psha
E6EB 8408                anda    #%00001000
E6ED 2703                beq     SignalPositive
                ;        jsr     RedLedOn          ; Debugging code allows
                ;        jsr     GreenLedOff       ; real-time display of
E6EF 32                  pula                      ; flow direction
E6F0 2001                bra     EndSignal SignalPositive ;        jsr     RedLedOff
                ;        jsr     GreenLedOn
E6F2 32                  pula EndSignal E6F3 39                  rts ;*
;* SUBROUTINE  : ConfigRegisters
;* CALLED BY   : Power On Reset
;* ASSUMPTIONS : x points to register base.
;* DESCRIPTION : I/O register init housekeeping.
;* REGISTERS   : Saved.
;*

ConfigRegisters

E6F4 36                  psha

E6F5 863B                ldaa    #SpiDirMsk
E6F7 A709                staa    ddrd,x            ; Configure port D for SPI
E6F9 8680                ldaa    #%10000000
E6FB A726                staa    pactl,x           ; Pin A7 is output
E6FD 6F08                clr     portd,x E6FF 32                  pula 700 39                   rts
```

CONFIDENTIAL

The Engineers Collaborative, Inc. 66.    Cross Assembler V1.0

```
;*
;* SUBROUTINE  : SelectAD
;* CALLED BY   : GetSignal
;* ASSUMPTIONS : (1) x points to register base
;*               (2) A/D select line is active low.
;* DESCRIPTION : Select A/D.
;* REGISTERS   : None.
;*

SelectAD

E701 1D0080         bclr    porta,x SerialAD

E704 39             rts

;*
;* SUBROUTINE  : DeSelectAD
;* CALLED BY   : GetSignal
;* ASSUMPTIONS : (1) x points to register base
;*               (2) A/D select line is active low.
;* DESCRIPTION : Select A/D.
;* REGISTERS   : None.
;*

DeSelectAD

E705 1C0080         bset    porta,x SerialAD

E708 39             rts

;                   * * * * * * * * * * * * *
;                   * LED Control Routines  *
;                   * * * * * * * * * * * * *

;*
;* SUBROUTINE  : RedLedOn
;* CALLED BY   : DisplayAcuity
;* ASSUMPTIONS : (1) x points to register base
;*               (2) LED select line is active high.
;* DESCRIPTION : Select red LED.
;* REGISTERS   : None.
;*

RedLedOn

E709 1C0802         bset    ' portd,x RedLed

E70C 39             rts

;*
;* SUBROUTINE  : RedLedOff
;* CALLED BY   : Power On Reset, DisplayAcuity
;* ASSUMPTIONS : (1) x points to register base
;*               (2) LED select line is active high.
;* DESCRIPTION : De-select red LED.
;* REGISTERS   : None.
;*
```

A46

CONFIDENTIAL

The Engineers Collaborative, Inc. 6F    Cross Assembler V1.0

```
                RedLedOff

E70D 100802             bclr     portd,x RedLed

E710 39                 rts

;*
                ;* SUBROUTINE  : AmberLedOn
                ;* CALLED BY   : DisplayAcuity
                ;* ASSUMPTIONS : (1) x points to register base
                ;*              (2) LED select line is active high.
                ;* DESCRIPTION : Select amber LED.
                ;* REGISTERS   : None.
                ;*
                AmberLedOn E711 1C0801             bset     portd,x AmberLed E714 39                 rts ;*
                ;* SUBROUTINE  : AmberLedOff
                ;* CALLED BY   : Power On Reset, DisplayAcuity
                ;* ASSUMPTIONS : (1) x points to register base
                ;*              (2) LED select line is active high.
                ;* DESCRIPTION : De-select amber LED.
                ;* REGISTERS   : None.
                ;*
                AmberLedOff E715 1D0801             bclr     portd,x AmberLed E718 39                 rts ;*
                ;* SUBROUTINE  : GreenLedOn
                ;* CALLED BY   : DisplayAcuity
                ;* ASSUMPTIONS : (1) x points to register base
                ;*              (2) LED select line is active high.
                ;* DESCRIPTION : Select green LED.
                ;* REGISTERS   : None.
                ;*
                GreenLedOn E719 1C0008             bset     porta,x GreenLed E71C 39                 rts ;*
                ;* SUBROUTINE  : GreenLedOff
                ;* CALLED BY   : Power On Reset, DisplayAcuity
                ;* ASSUMPTIONS : (1) x points to register base
                ;*              (2) LED select line is active high.
                ;* DESCRIPTION : De-select green LED.
```

A47

CONFIDENTIAL

The Engineers Collaborative, Inc. 6&  . Cross Assembler V1.0

```
                    ;* REGISTERS   : None.
                    ;*

GreenLedOff

E71D 1D0008             bclr    porta,x GreenLed

E720 39                 rts

;                * * * * * * * * * * * * *
                    ;                * Clock/Calander Routines *
                    ;                * * * * * * * * * * * * *

;*
                    ;* SUBROUTINE  : SetClock
                    ;* CALLED BY   : (*** NO CALLER ***) -- (Utility Program)
                    ;* ASSUMPTIONS : (1) Reads to program address space do not produce
                    ;*                   reads to clock address space.
                    ;*               (2) Time/Date information is stored at TimeSet.
                    ;* DESCRIPTION : Set DS1244Y Clock/Calendar.
                    ;*               Code is without subroutine calls in order to
                    ;*               avoid unintentional reference to clock address space.
                    ;*               Any read or write in the clock address space other
                    ;*               than the one read/multiple write recognition sequence
                    ;*               will cause a recognition abort.
                    ;* REGISTERS   : Saved
                    ;*

SetClock
E721 0F                 sei
E722 36                 psha
E723 37                 pshb
E724 183C               pshy E726 18CEB89A           ldy     #ClockCode E72A C601               ldab    #1

E72C 862000             ldaa    ClockScratch    ; Start recognition sequence

RecSendLoop
E72F 18A600             ldaa    0,y             ; No subroutine calls or memory
                                                ; references within the clock
E732 B72000             staa    ClockScratch    ; loop
E735 46                 rora
E736 B72000             staa    ClockScratch
E739 46                 rora
E73A B72000             staa    ClockScratch
E73D 46                 rora
E73E B72000             staa    ClockScratch
E741 46                 rora
E742 B72000             staa    ClockScratch
E745 46                 rora
E746 B72000             staa    ClockScratch
E749 46                 rora
E74A B72000             staa    ClockScratch
:74D 46                 rora
```

A48

CONFIDENTIAL

The Engineers Collaborative, Inc. 68   Cross Assembler V1.0

```
E74E 872000              staa     ClockScratch

E751 1808                iny
E753 59                  rolb
E754 2502                bcs      RecStreamSent
E756 2007                bra      RecSendLoop RecStreamSent E758 18CEB8A2            ldy      #TimeSet E75C C601                ldab     #1

DtaSendLoop

E75E 18A600              ldaa     0,y              ; No subroutine calls or memory
                                                   ; references within the clock
E761 872000              staa     ClockScratch     ; loop
E764 46                  rora
E765 872000              staa     ClockScratch
E768 46                  rora
E769 872000              staa     ClockScratch
E76C 46                  rora
E76D 872000              staa     ClockScratch
E770 46                  rora
E771 872000              staa     ClockScratch
E774 46                  rora
E775 872000              staa     ClockScratch
E778 46                  rora
E779 872000              staa     ClockScratch
E77C 46                  rora
E77D 872000              staa     ClockScratch E780 1808                iny
E782 59                  rolb
E783 2502                bcs      EndSet
E785 2007                bra      DtaSendLoop EndSet
E787 1838                puly
E789 33                  pulb
E78A 32                  pula E78B 0E                  cli E78C 39                  rts ;*
;* SUBROUTINE  : ReceiveClockBits
;* CALLED BY   : CheckAlarm, LogTime
;* ASSUMPTIONS : Reads to program address space do not produce
;*               reads to clock address space.
;* DESCRIPTION : Code is without subroutine calls in order to
;*               avoid unintentional reference to clock address space.
;*               Any read or write in the clock address space other
;*               than the one read/multiple write recognition sequence
;*               will cause a recognition abort.
;* REGISTERS   : Saved
```

A49

CONFIDENTIAL

The Engineers Collaborative, Inc. 6f     Cross Assembler V1.0

```
                  ;*

ReceiveClockBits

E78D 0F                     sei

E78E 36                     psha
E78F 37                     pshb
E790 183C                   pshy E792 18CEB89A               ldy    #ClockCode E796 C601                   ldab   #1

E798 B62000                 ldaa   ClockScratch      ; Start recognition sequence ClkSendLoop E79B 18A600                 ldaa   0,y               ; No subroutine calls or memory
                                                     ; references within the clock
E79E 872000                 staa   ClockScratch      ; loop
E7A1 46                     rora
E7A2 872000                 staa   ClockScratch
E7A5 46                     rora
E7A6 872000                 staa   ClockScratch
E7A9 46                     rora
E7AA 872000                 staa   ClockScratch
E7AD 46                     rora
E7AE 872000                 staa   ClockScratch
7B1 46                      rora
.7B2 872000                 staa   ClockScratch
E7B5 46                     rora
E7B6 872000                 staa   ClockScratch
E7B9 46                     rora
E7BA 872000                 staa   ClockScratch E7BD 1808                   iny
E7BF 59                     rolb
E7C0 2502                   bcs    StreamSent
E7C2 2007                   bra    ClkSendLoop StreamSent E7C4 C601                   ldab   #1
E7C6 18CEB8AA               ldy    #ClockData ByteRcvLoop E7CA 7FB883                 clr    ClockByte E7CD 8601                   ldaa   #1
E7CF 7B882                  staa   ClkBitCntr BitRcvLoop E7D2 B62000                 ldaa   ClockScratch
E7D5 46                     rora
E7D6 46                     rora
```

A50                                                                CONFIDENTIAL

The Engineers Collaborative, Inc. 68HC ross Assembler V1.0

```
 07 8480              anda    #%10000000

E7D9 8AB883           ora     ClockByte
E7DC 878883           staa    ClockByte

E7DF 798882           rol     ClkBitCntr
E7E2 2505             bcs     ByteCaptured
E7E4 768883           ror     ClockByte
E7E7 20E9             bra     BitRcvLoop ByteCaptured E7E9 18A700           staa    0,y
E7EC 1808             iny
E7EE 59               rolb
E7EF 2502             bcs     StreamCaptured
E7F1 2007             bra     ByteRcvLoop StreamCaptured E7F3 1838             puly
E7F5 33               pulb
E7F6 32               pula E7F7 0E               cli E7F8 39               rts ;             ****************
              ;             * Solenoid Firing Routines *
              ;             ****************
              ;*
              ;* SUBROUTINE : FireSolenoid
              ;* CALLED BY  : ValidFirePoint
              ;* ASSUMPTIONS: x points to register base.
              ;* DESCRIPTION: Starts the solenoid firing sequence by priming the
              ;*              handler with the first timer output compare interrupt.
              ;*              The solenoid interrupt handler (SolenoidService) will
              ;*              subsequently ensure that the entire waveform stored at
              ;*              PulseArray will be sent to the solenoid driver circuit.
              ;* REGISTERS  : Saved.
              ;*
              FireSolenoid E7F9 0F               sei E7FA 36               psha
E7FB 37               pshb
E7FC 183C             pshy E7FE BDE844           jsr     CheckSemaphore
E801 2630             bne     AbortFire E803 BDE830           jsr     CloseSemaphore 06 18CE8823          ldy     #PulseArray
```

AS1

CONFIDENTIAL

```
The Engineers Collaborative, Inc. 68h  Cross Assembler V1.0

:80A 18EC00             ldd    0,y
E80D E30E               addd   tcnt,x
E80F ED1A               std    toc3,x E811 BDE867             jsr    EnableSolenoid E814 7FB820             clr    PulseCounter
E817 7C8820             inc    PulseCounter
E81A 1808               iny
E81C 1808               iny
E81E 18FFB821           sty    ArrayPointer E822 B62001             ldaa   LogFlag
E825 2703               beq    EndFire
E827 BDE8C7             jsr    LogFiring EndFire E82A BDE848             jsr    DecShotCounter
E82D 7C2008             inc    FireCounter
E830 BDE85C             jsr    SetFireFlag AbortFire E833 1838               puly
E835 33                 pulb
E836 32                 pula E837 0E                 cli E838 39                 rts ;*
                ;* SUBROUTINE  : OpenSemaphore
                ;* CALLED BY   : SolenoidService
                ;* ASSUMPTIONS : Interrupts are disabled (semaphore manipulations
                ;*               must be indivisable operations).
                ;* DESCRIPTION : Clears semaphore flag indicating that solenoid
                ;*               firing is allowed.
                ;* REGISTERS   : None
                ;*
                OpenSemaphore E839 7FB833             clr    Semaphore E83C 39                 rts ;*
                ;* SUBROUTINE  : CloseSemaphore
                ;* CALLED BY   : FireSolenoid
                ;* ASSUMPTIONS : Interrupts are disabled (semaphore manipulations
                ;*               must be indivisable operations).
                ;* DESCRIPTION : Sets semaphore flag indicating that solenoid
                ;*               firing is disallowed.
                ;* REGISTERS   : None
                ;*
```

A52

CONFIDENTIAL

The Engineers Collaborative, Inc. 68H( ·oss Assembler V1.0

```
                CloseSemaphore

E83D 7F8833             clr     Semaphore
E840 7C8833             inc     Semaphore E843 39                 rts ;*
                ;* SUBROUTINE  : CheckSemaphore
                ;* CALLED BY   : FireSolenoid
                ;* ASSUMPTIONS : Interrupts are disabled (semaphore manipulations
                ;*               must be indivisable operations).
                ;* DESCRIPTION : Returns the value of the semaphore flag.
                ;*               (0 = Open, 1 = Closed)
                ;* REGISTERS   : acca
                ;*

CheckSemaphore

E844 868833             ldaa    Semaphore

E847 39                 rts

;*
                ;* SUBROUTINE  : DecShotCounter
                ;* CALLED BY   : FireSolenoid
                ;* ASSUMPTIONS : Location ShotCounter contains a strictly positive
                ;*               16 bit binary integer.
                ;* DESCRIPTION : Updates the shot counter, the SmartMist analogy
                ;*               to a camera exposure counter. Does nothing if
                ;*               ShotCounter zero, decrements ShotCounter otherwise.
                ;* REGISTERS   : All saved.
                ;*

DecShotCounter

E848 36                 psha
E849 37                 pshb

E84A FC888A             ldd     ShotCounter
E84D 1A830000           cmpd    #0
E851 2706               beq     EndDecCounter E853 830001             subd    #1
E856 FD888A             std     ShotCounter EndDecCounter E859 33                 pulb
E85A 32                 pula E85B 39                 rts ;*
                ;* SUBROUTINE : SetFireFlag
                ;* CALLED BY  : FireSolenoid
```

A53

CONFIDENTIAL

The Engineers Collaborative, Inc. 68     Cross Assembler V1.0

```
            ;* ASSUMPTIONS : None
            ;* DESCRIPTION : Sets flag indicating that solenoid firing took place.
            ;* REGISTERS   : None
            ;*

SetFireFlag

E85C 7F202B         clr     FireFlag
E85F 7C202B         inc     FireFlag

E862 39             rts
            ;*
            ;* SUBROUTINE  : ClearFireFlag
            ;* CALLED BY   : ProcessBreath
            ;* ASSUMPTIONS : None
            ;* DESCRIPTION : Clears flag which, when set, indicates that
            ;*               solenoid firing took place.
            ;* REGISTERS   : None
            ;*

ClearFireFlag

E863 7F202B         clr     FireFlag

E866 39             rts
            ;*
            ;* SUBROUTINE  : EnableSolenoid
            ;* CALLED BY   : FireSolenoid
            ;* ASSUMPTIONS : (1) x points to register base,
            ;*               (2) Solenoid firing to commence now.
            ;* DESCRIPTION : Set up timer four to allow output compare pin
            ;*               activation of solenoid.
            ;* REGISTERS   : None
            ;*

EnableSolenoid

E867 1D23DF         bclr    tflg1,x SolenoidFlgClr
E86A 1C2220         bset    tmsk1,x SolenoidInt
E86D 1C2010         bset    tctl1,x ToggleSoloPin
E870 1C0820         bset    cforc,x SolenoidForce E873 39             rts
            ;*
            ;* SUBROUTINE  : DisableSolenoid
            ;* CALLED BY   : Power On Reset, SolenoidService
            ;* ASSUMPTIONS : x points to register base.
            ;* DESCRIPTION : Disables output compare pin toggle. Also ensures
            ;*               that output pin left in the off state. (If output
            ;*               pin not specifically disabled in this fashion,
            ;*               solenoid can be be driven high continuously).
            ;* REGISTERS   : None.
            ;*

DisableSolenoid
```

The Engineers Collaborative, Inc. 68HC    oss Assembler V1.0

```
.74 102220              bclr    tmsk1,x SolenoidInt
E877 102010             bclr    tctl1,x ToggleSoloPin E87A 39                 rts ;               * * * * * * * * * * * *
                ;               * Data Logging Routines *
                ;               * * * * * * * * * * * *

;*
                ;* SUBROUTINE : LogTime
                ;* CALLED BY  : LoggingOn
                ;* ASSUMPTIONS: None
                ;* DESCRIPTION: Gets time data from the Dallas Phantom Clock and
                ;*              stores it in the appropriate position in the
                ;*              current data logging area.
                ;* REGISTERS  : Saved
                ;*

LogTime
E87B 36                 psha
E87C 37                 pshb
E87D 3C                 pshx
E87E 183C               pshy E880 BDE780             jsr     ReceiveClockBits
E883 18FE2002           ldy     DataBlock
E887 CEB8AB             ldx     #SecondsDta
 58A 8607               ldaa    #TimeBytes MoveLoop
E88C E600               ldab    0,x
E88E 18E700             stab    TimeOffset,y
E891 08                 inx
E892 1808               iny
E894 4A                 deca
E895 26F5               bne     MoveLoop E897 1838               puly
E899 38                 pulx
E89A 33                 pulb
E89B 32                 pula E89C 39                 rts ;*
                ;* SUBROUTINE : LogDataPoint
                ;* CALLED BY  : GetDataPoint
                ;* ASSUMPTIONS: Data to be logged is in double register D.
                ;* DESCRIPTION: Converts (flow) data to be logged into BCD and stores
                ;*              it at the next position the current data logging area.
                ;* REGISTERS  : Saved
                ;*

LogDataPoint

E89D 36                 psha
```

CONFIDENTIAL

The Engineers Collaborative, Inc. 68    Cross Assembler V1.0

```
E89E 37                pshb
E89F 3C                pshx
E8A0 183C              pshy
E8A2 BDE58F            jsr      BinaryToBCD
E8A5 FCB898            ldd      BCDResult
E8A8 18FE2004          ldy      DataIndex
E8AC 18ED0A            std      DataOffset,y
E8AF 1808              iny
E8B1 1808              iny
E8B3 18FF2004          sty      DataIndex
E8B7 18FE2006          ldy      DataCounter
E8BB 1808              iny
E8BD 18FF2006          sty      DataCounter E8C1 1838              puly
E8C3 38                pulx
E8C4 33                pulb
E8C5 32                pula E8C6 39                rts ;*
;* SUBROUTINE  : LogFiring
;* CALLED BY   : FireSolenoid
;* ASSUMPTIONS : DataCounter points to a flow data point acquired
;*               coincident with a solenoid firing.
;* DESCRIPTION : The array index of the last flow data point
;*               is appended to the FirePoints array. The next
;*               available position in the FirePoints array is
;*               indicated by FireIndex.
;* REGISTERS   : Saved
;*

LogFiring

E8C7 36                psha
E8C8 37                pshb
E8C9 3C                pshx
E8CA 183C              pshy E8CC FC2006            ldd      DataCounter
E8CF 18FE2009          ldy      FireIndex
E8D3 18ED00            std      0,y
E8D6 1808              iny
E8D8 1808              iny
E8DA 18FF2009          sty      FireIndex E8DE 1838              puly
E8E0 38                pulx
E8E1 33                pulb
E8E2 32                pula E8E3 39                rts ;*
;* SUBROUTINE  : LoggingOn
;* CALLED BY   : IdleLoop
;* ASSUMPTIONS : None
```

A56      CONFIDENTIAL

The Engineers Collaborative, Inc. 68h Cross Assembler V1.0

```
;* DESCRIPTION : Initializes all variables relevent to the data
;*                logging operations.
;* REGISTERS   : Saved.
;*

LoggingOn

E8E4  36                psha
E8E5  37                pshb
E8E6  183C              pshy E8E8  FC2002            ldd    DataBlock
E8EB  C30320            addd   #MaxLogFileLen
E8EE  1A83B000          cmpd   #LogFileEnd
E8F2  2432              bhs    EndLogOn E8F4  BDE878            jsr    LogTime
E8F7  7F2001            clr    LogFlag
E8FA  7C2001            inc    LogFlag
E8FD  7F2008            clr    FireCounter
E900  CC2008            ldd    #FirePoints
E903  FD2009            std    FireIndex
E906  FC2002            ldd    DataBlock
E909  FD2004            std    DataIndex
E90C  CC0000            ldd    #$0000
E90F  FD2006            std    DataCounter E912  18FE2002          ldy    DataBlock
E916  B6B854            ldaa   CurrentMode
E919  18A707            staa   ModeOffset,y E91C  18FE202C          ldy    BlockCount
E920  1808              iny
E922  18FF202C          sty    BlockCount EndLogOn E926  1838              puly
E928  33                pulb
E929  32                pula E92A  39                rts ;*
;* SUBROUTINE  : LoggingOff
;* CALLED BY   : IdleLoop
;* ASSUMPTIONS : None
;* DESCRIPTION : Close data logging file by transferring array length
;*                and solenoid firing information over to the data
;*                logging array.
;* REGISTERS   : Saved
;*

LoggingOff

E92B  36                psha
E92C  37                pshb
 92D  3C                pshx
```

The Engineers Collaborative, Inc. 68HC oss Assembler V1.0

```
:92E 183C              pshy

E930 18FE2002          ldy    DataBlock
E934 FC2006            ldd    DataCounter
E937 18ED08            std    LengthOffset,y E93A 7F2001            clr    LogFlag
E93D 18FE2004          ldy    DataIndex
E941 B62008            lda    FireCounter
E944 18A700            staa   0,y
E947 7C2008            inc    FireCounter
E94A 1808              iny
E94C CE200B            ldx    #FirePoints StoreLoop E94F 7A2008            dec    FireCounter
E952 270A              beq    EndTransfer E954 EC00              ldd    0,x
E956 18ED00            std    0,y
E959 08                inx
E95A 1808              iny
E95C 20F1              bra    StoreLoop EndTransfer E95E 1838              puly
E960 38                pulx
E961 33                pulb
E962 32                pula E963 39                rts
```

```
;              * * * * * * * * * * * * * * *
;              * Interrupt Service Routines *
;              * * * * * * * * * * * * * * *

;*
;* SUBROUTINE  : SpeakerService (an interrupt handler)
;* CALLED BY   : Output Compare Four Interrupt (OC4)
;* ASSUMPTIONS : (1) Registers saved automatically.
;*               (2) ToneValue holds a tone pulse period proportional
;*                   to the most recently measured instaneous flow.
;*               (3) x points to register base.
;* DESCRIPTION : Force ToneValue to be within pre determined
;*               boundries for an esthetic sound and update
;*               the output compare timer.
;* REGISTERS   : All are saved at interrupt service time by the
;*               hardware.
;*
```

```
            SpeakerService

E964 CE1000            ldx    #RegBase
E967 FC8800            ldd    ToneValue
E96A 8100              cmpa   #00
```

AS8

CONFIDENTIAL

The Engineers Collaborative, Inc. 68H    ross Assembler V1.0

```
96C  2609                    bne     ContSpeakServ
E96E C180                    cmpb    #LowestToneValue
E970 2502                    blo     BumpUp
E972 2003                    bra     ContSpeakServ BumpUp E974 CC0080                  ldd     #LowestToneValue ContSpeakServ E977 BDE982                  jsr     SpeedToneAdj
E97A E31C                    addd    toc4,x
E97C ED1C                    std     toc4,x
E97E 1D23EF                  bclr    tflg1,x ToneFlgClr E981 38                      rti ;*
             ;* SUBROUTINE  : SpeedToneAdj
             ;* CALLED BY   : SpeakerService
             ;* ASSUMPTIONS : Tone value in register D
             ;* DESCRIPTION : Called by SpeakerService. All tone adjustments
             ;*               made by SpeakerService assume default timer speed.
             ;*               This routine reads the SpeedControl mask used
             ;*               set timer speed and divides the passed tone value
             ;*               by the pre-scaler value. The tone frequency range
             ;*               will thus be approximately the same at different
             ;*               timer pre-scaler settings.
             ;* REGISTERS   : acca, accb
             ;*

SpeedToneAdj

E982 183C                    pshy
E984 18CE0001                ldy     #SpeedCntrl
E988 2709                    beq     EndSpeedAdjust
E98A 0C                      clc
E98B 46                      rora
E98C 56                      rorb SpeedLoop E98D 46                      rora
E98E 56                      rorb E98F 1809                    dey E991 26FA                    bne     SpeedLoop EndSpeedAdjust E993 1838                    puly E995 39                      rts ;*
             ;* SUBROUTINE  : SolenoidService (an interrupt handler)
```

A59

The Engineers Collaborative, Inc.    1 Cross Assembler V1.0

```
;* CALLED BY    : Output Compare Three Interrupt (OC3)
;* ASSUMPTIONS  : (1) Registers saved automatically.
;*                (2) x points to register base.
;* DESCRIPTION  : Subsequent entries in PulseArray are used to
;*                determine the next pulse sent to the solenoid
;*                circuit. Control will continue to return to
;*                this handler until PulseArray is exhausted. At
;*                that time, the solenoid controller is switched off
;*                pending the next firing. A very narrow pulse
;*                will be produced at the end of the programmed
;*                waveform. This artifact results from latencies
;*                encountered during exit and is of insufficient
;*                duration to fire the actuator.
;* REGISTERS    : All are saved at interrupt service time by the
;*                hardware.
;*

SolenoidService

E996 CE1000            ldx     #RegBase
E999 18FEB821          ldy     ArrayPointer E99D B6881F            ldaa    NumPulses
E9A0 48                asla E9A1 B1B820            cmpa    PulseCounter
E9A4 2717              beq     SleepSolenoid NextInterval E9A6 EC1A              ldd     toc3,x
E9A8 18E300            addd    0,y
E9AB ED1A              std     toc3,x
E9AD 1D230F            bclr    tflg1,x SolenoidFlgClr E9B0 7C8820            inc     PulseCounter E9B3 1808              iny
E9B5 1808              iny
E9B7 18FFB821          sty     ArrayPointer E9B8 200B              bra     EndSolService SleepSolenoid E9BD BDE874            jsr     DisableSolenoid
E9C0 7FB820            clr     PulseCounter
E9C3 BDE839            jsr     OpenSemaphore
E9C6 2000              bra     EndSolService EndSolService E9C8 3B                rti ;               *********************
;               * Service Routine Indirect Jump Table *
;               *********************
```

The Engineers Collaborative, Inc.    | Cross Assembler V1.0

```
9C9  38           SciService       rti
.9CA 38           SpiService       rti
E9CB 38           PulseInService   rti
E9CC 38           PulseOvfService  rti
E9CD 38           TimerOvfService  rti
E9CE 38           OC5Service       rti E9CF 7EE964       OC4Service       jmp    SpeakerService
E9D2 7EE996       OC3Service       jmp    SolenoidService E9D5 38           OC2Service       rti
E9D6 38           OC1Service       rti
E9D7 38           TIC3Service      rti
E9D8 38           TIC2Service      rti
E9D9 38           TIC1Service      rti
E9DA 38           RealTimeService  rti
E9DB 38           IRQService       rti
E9DC 38           XIRQService      rti
E9DD 38           SWIService       rti
E9DE 38           BadOpService     rti
E9DF 38           COPFailService   rti
E9E0 38           COPClkFailSrv    rti ;                ***********
                  ;                * Copyright Notice *
                  ;                ***********

E9E1 436F7079     CopyRight        fcc    "Copyright (C) 1990,1991 Miris Medical"
     72696768
     74202843
     29203139
     39302C31
     39393120
     4D697269
     73204D65
     64696361
     6C B800                               org    ExtRam2

;                ***********
                  ;                * Variable Pitch Data *
                  ;                ***********

B800 0100         ToneValue        dw     $0100

;                ***********
                  ;                * Led Display Data *
                  ;                ***********

B802 00           DisplayByte      db     $00
B803 0000         AsciiDestPtr     dw     $0000
B805 30303030     AsciiString      fcc    "0000"
B809 30303030     AsciiTime        fcc    "0000"

;                ***********
                  ;                * Alarm Clock Data *
```

A61

CONFIDENTIAL

The Engineers Collaborative, Inc.    1 Cross Assembler V1.0

```
                  ;              * * * * * * * * * *

B80D 0100         AlarmTone      dw    $0100
B80F 78           AlarmDuration  db    120
B810 00           AlarmCounter   db    $00
B811 07           NumAlarms      db    7
B812 00           LastAlarm      db    $00
B813 60504030     AlarmTime      db    $60,$50,$40,$30,$20,$10,$00,$60,$50,$40,$30,$20
     20100060
     50403020

;              * * * * * * * * * * * * * *
                  ;              * Solenoid Waveform Data *
                  ;              * * * * * * * * * * * * * *
                  ;
                  ; Arbitrary waveform generator data
                  ;
                  ; Pusatile solenoid driver waveforms with varying numbers
                  ; of pulses, pulse widths and duty cycles were tested
                  ; in conjuction with an aerosolized albuterol delivery
                  ; system by Rubsamen and Goodman on 11/27/90 at Armstrong
                  ; Laboratories in West Roxbury, Massachusetts. A solenoid
                  ; driver waveform consisting of four pulses, duty cycle
                  ; 13% and pulse width 112 msec was found to significantly
                  ; increase the in vitro respiratory fraction of delivered
                  ; drug compared with a standard MDI.
                  ;
                  ; These parameters are equivalent to four pulses, each
                  ; with on-cycle 14.56 msec and off-cycle 97.44 msec,
                  ; and are encoded below.

B81F 04           NumPulses      db    $04
B820 00           PulseCounter   db    $00
B821 B823         ArrayPointer   dw    PulseArray B823 1C70         PulseArray     dw    7280        ; On cycle
B825 BE50                        dw    48720       ; Off cycle
B827 1C70                        dw    7280        ; On cycle
B829 BE50                        dw    48720       ; Off cycle
B82B 1C70                        dw    7280        ; On cycle
B82D BE50                        dw    48720       ; Off cycle
B82F 1C70                        dw    7280        ; On cycle
B831 BE50                        dw    48720       ; Off cycle B833 00           Semaphore      db    $00         ; Solenoid semaphore -- prevents
                                                   ; a firing request when a
                                                   ; solenoid firing is in progress ;              * * * * * * * *
                  ;              * A/D Data Area *
                  ;              * * * * * * * *
                  ;
                  ; A/D 12 bit data conversion storage area
                  ;
                  SampleValue
```

A62                                              CONFIDENTIAL

The Engineers Collaborative, Inc. 6  Cross Assembler V1.0

```
834  00       SampleHigh    db    $00
4835 00       SampleLow     db    $00

8836 00       TicCounter    db    $00
8837 00       SecondsCntr   db    $00

8838 0000     AbsScratch    dw    $0000

;             * * * * * * * * * * *
              ;             *  Boxcar Filter Data  *
              ;             * * * * * * * * * * *

883A          Filter        ds    FilterLength*2

884A 00       FilterIndex16 db    $00         ; Allows loading FilterIndex
                                              ; as a 16 bit quantity.
884B 00       FilterIndex   db    $00         ; the low byte of a word 884C 00       FilterCounter db    $00
884D 0000     SmoothValue   dw    $0000

;             * * * * * * * * * *
              ;             *  Last Breath Data  *
              ;             * * * * * * * * * *

884F 00       LastDirection db    $00         ; Zero if sign bit of last
                                              ; data point clear, non-zero
                                              ; otherwise (actual non-zero
                                              ; value not specified)
8850 0000     LastMaxFlow   dw    $0000
8852 0000     LastMaxVol    dw    $0000

;             * * * * * * * *
              ;             *  Mode Data  *
              ;             * * * * * * * *

8854 00       CurrentMode    db   $00
8855 00       LastInhaleMode db   $00
8856 00       ActiveFlag     db   $00

;             * * * * * * * * * * * *
              ;             *  Flow Calibration Data  *
              ;             * * * * * * * * * * * *

; A/D value to flow calibration table.
; Basic conversion formula is multiplication of 9 bit positive
; value (ie. TrimBits = 2) by two. The following lookup table
; introduces an additional correction factor based on the high
; four bits of this quantity.
;
; Correction factors are expressed as a percent. The correction
; direction is assumed down (ie. subtract correction from result).
; The first five percentages expressible as right shift operations are:
;
;             50%, 25%, 12.5%, 6.25%, 3.125%
;
```

A63

CONFIDENTIAL

The Engineers Collaborative, Inc.    '1 Cross Assembler v1.0

```
                        ; Therefore, correction factors determined here were coerced to these
                        ; values. Each correction factor is expressed as an integer
                        ; representing the number of right shifts required.
                        ; The value resulting from this series of
                        ; shifts is subsequently subtracted from the uncorrected result.
                        ; For example, the correction factor 6.25% would be represented
                        ; as 4 signifying that four right shifts are required.
                        ;
                        ; Note that correction factors ranging from 50%-1.56% over the
                        ; 16 ranges below can be expressed in a 48 bit packet consisting
                        ; of 16 contiguous 3 bit quantities, each representing 0 - 6 left
                        ; shifts.

CalTable

;       Encoding    High 4 bits  Range              Correction Factor 8857 00                     db      0           ; 0000 -> 0    -  63   l/min,   correction = 0%
8858 00                     db      0           ; 0001 -> 63   - 127   l/min,   correction = 0%
8859 00                     db      0           ; 0010 -> 128  - 191   l/min,   correction = 0%
885A 00                     db      0           ; 0011 -> 192  - 255   l/min,   correction = 0%
885B 00                     db      0           ; 0100 -> 256  - 319   l/min,   correction = 0%
885C 00                     db      0           ; 0101 -> 320  - 383   l/min,   correction = 0%
885D 00                     db      0           ; 0110 -> 384  - 447   l/min,   correction = 0%
885E 00                     db      0           ; 0111 -> 448  - 511   l/min,   correction = 0%
885F 00                     db      0           ; 1000 -> 512  - 575   l/min,   correction = 0%
8860 00                     db      0           ; 1001 -> 576  - 639   l/min,   correction = 0%
8861 00                     db      0           ; 1010 -> 640  - 703   l/min,   correction = 0%
8862 00                     db      0           ; 1011 -> 704  - 767   l/min,   correction = 0%
8863 00                     db      0           ; 1100 -> 768  - 831   l/min,   correction = 0%
8864 00                     db      0           ; 1101 -> 832  - 895   l/min,   correction = 0%
8865 00                     db      0           ; 1110 -> 896  - 959   l/min,   correction = 0%
8866 00                     db      0           ; 1111 -> 960  - 1023  l/min,   correction = 0%

; Scratch area for calibration calculations 8867 00                 CalByte         db      $00

CalWord
8868 00                 CalWordHigh     db      $00
8869 00                 CalWordLow      db      $00

; Last calibrated flow value 886A 0000               CalValue        dw      $0000

;                       * * * * * * * * * * *
                        ;                       *  Integration Data  *
                        ;                       * * * * * * * * * * *

; Integration algorithm:
                        ; The pneumotach used for this prototype was calibrated in liters
                        ; per minute (ie. a mapping exists between liters per minute and
                        ; perssure drop across the device). We are measuring flow at 1/60
                        ; second intervals. In theory, the integrator would be implemented
                        ; simply by taking each instantaneous flow and converting from
                        ; liters per minute to liters per 1/60 second. This is accomplished
                        ; by dividing by 3600 (ie. dividing by 60 twice). One would probably
```

A64

CONFIDENTIAL

The Engineers Collaborative, Inc.    1 Cross Assembler V1.0

```
; take the average of a given flow point with its predecessor in order
; to estimate flow change bewteen sample points.
;
; This approach has two drawbacks. First, the error introduced by
; dividing by 3600 would be large since the instaneous flow rates
; are in the range of a few hundred liters per minute. Second, the
; microprocessor being employed has no floating point unit. Therefore,
; division by 3600 is non-trivial.
;
; Our goal is to determine a conversion factor which is a power of two
; and applies to an integer multiple of 1/60 interval sample points.
; For example, the conversion factor 1024 converts liters per
; minute to liters per 0.059 seconds or about 3.5 sample points.
; The current implementation of the integrator therefore works
; as follows:
;
; (1) Sum four consecutive sample points. Call this the TicSum.
; (2) Compute the average of the TicSum through two right
;     shifts (done on the fly).
; (3) Add this computed average into RunningSum.
; (4) When IntegralTicCount reaches UpdateTics, divide
;     RunningSum by 1024 yielding the resuilt in liters.
;     Add the result into the variable Integral.
; (5) When IntegralTicCount reaches IntegralTics, terminate
;     the integration.
; (6) If IntegrateOff is excecuted before IntegralTics is reached,
;     then terminate the integration (de facto) then.
;
; Integration Data:

886C 0000    RunningSum       dw    $0000       ; Sum of tic groups
886E 0000    TicSum           dw    $0000       ; Sum in a tic group
                                                ; (average will be taken)
8870 0000    Integral         dw    $0000       ; Result 8872 0000    IntegralTicCnt   dw    $0000       ; Tic count for entire integration.
8874 00      GroupTicCnt      db    $00         ; Tic count for one tic group
8875 00      UpdateCount      db    $00         ; Start from UpdateTics and
             decrement
8876 00      Integrateflag    db    $00         ; Unity while integrating.
8877 0000    ScratchCntr      dw    $0000

;              * * * * * * * * * *
             ;              * Binary->BCD Data *
             ;              * * * * * * * * * *

;
             ; Binary->BCD conversion data
             ; BCD representations of powers-of-two are stored as <LowPair><HighPair>
             ; BCD words in order to simplify array indexing logic.
             ;
             BCDTable
8879 01000200          fdb    $0100,$0200,$0400,$0800,$1600
     04000800
     1600
?83  32006400          fdb    $3200,$6400,$2801,$5602,$1205
```

The Engineers Collaborative, Inc.    1 Cross Assembler V1.0

```
           28015602
           1205
888D  24104820              fdb      $2410,$4820,$9640,$9281
      96409281

8895  0000     BCDSourcePtr    dw      0
8897  00       BCDConvCtr      db      $00

BCDResult 8898  00       BCDResultLow    db      $00
8899  00       BCDResultHigh   db      $00

;               ************
               ;               * Clock/Calander Data *
               ;               ************

; Dallas RAM phantom clock storage area
               ; (Note that this area MUST reside in an address
               ; block DIFFERENT FROM that of the program memory)

889A  C53AA35C  ClockCode     fcb      $c5,$3a,$a3,$5c,$c5,$3a,$a3,$5c
      C53AA35C ; Constant data for setting clock
               ; (set for 24 hour format)

TimeSet
88A2  00       TenthSec        db      $00
88A3  00       Seconds         db      $00
88A4  00       Minutes         db      $00
88A5  00       Hours           db      $00
88A6  12       Day             db      %00010010
88A7  04       Date            db      %00000100
88A8  12       Month           db      %00010010
88A9  90       Year            db      %10010000

; Storage area for data read from clock

ClockData

88AA  00       TenthSecDta     db      $00
88AB  00       SecondsDta      db      $00
88AC  00       MinutesDta      db      $00
88AD  00       HoursDta        db      $00
88AE  00       DayDta          db      $00
88AF  00       DateDta         db      $00
88B0  00       MonthDta        db      $00
88B1  00       YearDta         db      $00

; Clock read bookeeping data

88B2  01       ClkBitCntr      db      %00000001
88B3  00       ClockByte       db      $00

;               **********
```

CONFIDENTIAL

The Engineers Collaborative, Inc. 6      Cross Assembler V1.0

```
                    ;                    * Last Breath Data *
                    ;                    * * * * * * * * * *

B884 00             BreathDir       db      $00
B885 0000           MaxFlow         dw      $0000
B887 0000           MaxVolume       dw      $0000

;                    * * * * * * * * * *
                    ;                    * Firing Point Data *
                    ;                    * * * * * * * * * *

B889 01             FireCount       db      1               ; Number of firing points B88A 0190           ShotCounter     dw      400             ; User-displayed shot counter
                                                            ; shows number of shots left
                                                            ; in cannister ; Next firing point information is computed based on current
                    ; mode and placed here. Note that for a programmed breath, this
                    ; computation involves only copying data from the FireFlow and
                    ; FireVolume arrays.

B88C B8C0           NxtFireFlow     dw      FlowPoints
B88E B8C8           NxtFireVol      dw      VolPoints
B8C0 00000000       FlowPoints      dw      $0000,$0000,$0000,$0000
     00000000
B8C8 00000000       VolPoints       dw      $0000,$0000,$0000,$0000
     00000000

;
                    ; Programmed breath mode firing points
                    ;

B8D0 00320064       FireFlow        dw      50,100          ; Minimum Flow For Firing
B8D4 00010001       FireVolume      dw      1,1             ; Minimum Volume for Firing ;
                    ; Calibration breath mode firing points. Programmed precentages used
                    ; in conjuction with last breath (calibration breath) in order to
                    ; determine firing points for current breath.
                    ;
                    ; Percentage information is encoded as follows:
                    ;
                    ; 50% = 1, 25% = 2, 12.5% = 3, 6.25% = 4, 3.12% = 5
                    ;
                    ; In other words, the encoded percentage is equal to the number
                    ; of right shift operations required on the original value.
                    ;

B8D8 0102           PctFireFlow     db      1,2             ; Minimum percentage of peak flow
                                                            ; for firing
B8DA 0102           PctFireVol      db      1,2             ; Minimum percentage of peak volume
                                                            ; for firing
B8DC 00             CalScratch      db      $00
B8DD 00             PctScratch      db      $00

;                    * * * * * * * * * *
                    ;                    * Pulmonary Function Data *
```

The Engineers Collaborative, Inc.    1 Cross Assembler V1.0

```
                ;                 * * * * * * * * * * * *
                ;
                ; Peak flow meter acuity index boundries
                ;
                ; AcuityGreen ==> pulmonary function nominal
                ; AcuityAmber ==> pulmonary function marginal
                ; AcuityRed   ==> pulmonary function critical B8DE 0190       AcuityGreen   dw    400
B8E0 012C       AcuityAmber   dw    300
B8E2 00C8       AcuityRed     dw    200

2001                          org   ExtRam3
                ;
                ;                 * * * * * * * * * *
                ;                 * Data Logging Area *
                ;                 * * * * * * * * * *
                ;
                ; Format for PFT curve data:
                ;
                ; Modes 0-1 Format:
                ;
                ; <TimeStamp><Mode><CurveLength><CurveData><NumFirings>
                ; <FiringPoint1>...<FiringPointN> (all contiguous)
                ;
                ; Where:
                ;
                ;    <TimeStamp>  :: <Seconds><Minutes><Hours><Day><Month><Year>
                ;                    (one BCD coded byte per value)
                ;         <Mode>  :: $00 = Programmed Breath Mode
                ;                    $01 = Calibrated Breath Mode
                ;                    $02 = Peak Flow Measurement Mode
                ;   <CurveLength> :: Two byte integer quantity (binary)
                ;     <CurveData> :: <CurveLength> words (unsigned binary)
                ;    <NumFirings> :: One byte integer (binary)
                ; <FiringPoint1>  :: <NumFirings> word(s) pointing to the byte(s)
                ;                    in CurveData where drug was delivered
                ;
                ; Mode 2 Format:
                ;
                ; <TimeStamp><Mode><CurveLength><CurveData><NumFirings=0>
                ;
                ;
                ; General Inforation:
                ;
                ;
                ; DataBlock points to next available space in memory for the next
                ; formatted block of data as described above. Data in CurveData
                ; represents exclusively inspiratory or expiratory data depending
                ; on mode. (ie. inspiratory for modes 0 and 1 and expiratory for
                ; mode 2). DataIndex is the offset from DataBlock into the
                ; next avaliable word for a flow data point (ie. curve data).

2001 00         LogFlag       db    $00
2002 202E       DataBlock     dw    BlockStart
```

A68

The Engineers Collaborative, Inc.    1 Cross Assembler V1.0

```
2004 2038            DataIndex       dw      BlockStart+DataOffset
2006 0000            DataCounter     dw      $0000
2008 00              FireCounter     db      $00
2009 200B            FireIndex       dw      FirePoints
200B 00000000        FirePoints      dw      $0000,$0000,$0000,$0000
     00000000
2013 00000000                        dw      $0000,$0000,$0000,$0000
     00000000
201B 00000000                        dw      $0000,$0000,$0000,$0000
     00000000
2023 00000000                        dw      $0000,$0000,$0000,$0000
     00000000

202B 00              FireFlag        db      $00

202C 0000            BlockCount      dw      $0000

202E                 BlockStart      ds      8192

;                       * * * * * * * * * * *
                     ;                       * Interrupt Vectors *
                     ;                       * * * * * * * * * * *

FFD6                                 org     vectors

FFD6 E9C9            sci             dw      SciService
FFD8 E9CA            spi             dw      SpiService
FFDA E9CB            PulseInput      dw      PulseInService
FFDC E9CC            PulseOvf        dw      PulseOvfService
FFDE E9CD            TimerOvf        dw      TimerOvfService
FFE0 E9CE            OC5             dw      OC5Service
FFE2 E9CF            OC4             dw      OC4Service
FFE4 E9D2            OC3             dw      OC3Service
FFE6 E9D5            OC2             dw      OC2Service
FFE8 E9D6            OC1             dw      OC1Service
FFEA E9D7            TIC3            dw      TIC3Service
FFEC E9D8            TIC2            dw      TIC2Service
FFEE E9D9            TIC1            dw      TIC1Service
FFF0 E9DA            RealTime        dw      RealTimeService
FFF2 E9DB            IRQ             dw      IRQService
FFF4 E9DC            XIRQ            dw      XIRQService
FFF6 E9DD            SWI             dw      SWIService
FFF8 E9DE            BadOpcode       dw      BadOpService
FFFA E9DF            COPFailure      dw      COPFailService
FFFC E9E0            COPClockFail    dw      COPClkFailSrv
FFFE E000            reset           dw      PowerOnReset 0000                                 end
```

Assembly complete - Errors = 0 , Warnings = 0

```
---Symbol Table---
ADWait            E689
Abortfire         E833
AbsScratch        B838
AbsWordLength     0009
AbsoluteValue     E44D
AcquireSignal     E37A
ActivateSPI       E6A9
ActiveFlag        B856
AcuityAmber       B8E0
AcuityGreen       B8DE
AcuityRed         B8E2
AddBCDValue       E580
AddNextElement    E4B9
AlarmCounter      B810
AlarmDuration     B80F
AlarmOff          E564
AlarmOn           E558
AlarmTime         B813
AlarmTone         B80D
AmberLed          0001
AmberLedOff       E715
AmberLedOn        E711
ArrayPointer      B821
AsciiDestPtr      B803
AsciiMask         0010
AsciiString       B805
AsciiTime         B809
AverageLoop       E412
BCDConvCtr        B897
BCDConvOone       E5D1
BCDLoop           E5A0
BCDResult         B898
BCDResultHigh     B899
BCDResultLow      B898
BCDSourcePtr      B895
BCDTable          B879
BCDToAscii        E5D2
BadOpService      E9DE
BadOpcode         FFF8
BinaryToBCD       E58F
BitRcvLoop        E7D2
BlockCount        202C
BlockStart        202E
BreathDir         B8B4
BumpFilterIndex   E48A
BumpUp            E974
ByteCaptured      E7E9
ByteRcvLoop       E7CA
COPClkFailSrv     E9E0
COPClockFail      FFFC
COPFailService    E9DF
COPFailure        FFFA
CalBreath         E0AC
CalBreathMode     0001
CalByte           B867
CalFactor         E2F3
CalFieldLength    0004
CalFlow           E316
CalFlowLoop       E1D0
CalMode           E12E
CalModePts        E166
CalRotate         E306
CalScratch        B8DC
CalTable          B857
```

CONFIDENTIAL

| Symbol | Address |
|---|---|
| CalValue | B86A |
| CalVolLoop | E1F1 |
| CalWord | B868 |
| CalWordHigh | B868 |
| CalWordLow | B869 |
| CharAddrMask | 001F |
| CheckAlarm | E510 |
| CheckLastFiring | E141 |
| CheckNextTime | E535 |
| CheckSemaphore | E844 |
| CheckThreshold | E274 |
| CheckVolume | E235 |
| ClearAcc | E281 |
| ClearActiveFlag | E346 |
| ClearBoxCar | E4D2 |
| ClearFireFlag | E863 |
| ClearLoop | E4E2 |
| ClearMaxValues | E116 |
| ClearRegD | E14F |
| ClearTimerRegs | E57D |
| ClkBitCntr | B882 |
| ClkSendLoop | E79B |
| ClockByte | B883 |
| ClockCode | B89A |
| ClockData | B8AA |
| ClockScratch | 2000 |
| CloseSemaphore | E83D |
| ComputeAverage | E407 |
| ComputeCalPts | E18D |
| ComputeFirePts | E154 |
| ComputeIntegral | E418 |
| ComputeProgPts | E176 |
| ConfigRTI | E576 |
| ConfigRegisters | E6F4 |
| ConfigWaveTimer | E588 |
| ContSpeakServ | E977 |
| ContinueInsp | E103 |
| ConvertDelay | 0032 |
| CopyRight | E9E1 |
| CurrentMode | B854 |
| DataBlock | 2002 |
| DataCounter | 2006 |
| DataIndex | 2004 |
| DataOffset | 000A |
| Date | B8A7 |
| DateDta | B8AF |
| Day | B8A6 |
| DayDta | B8AE |
| DeSelectAD | E705 |
| DecShotCounter | E848 |
| DisableSolenoid | E874 |
| DisableTone | E62D |
| DispNxtChar | E656 |
| DispSelPin | 0020 |
| DisplayAcuity | E287 |
| DisplayByte | B802 |
| DisplayCharSel | E670 |
| DisplayCycle | E68E |
| DisplayData | E634 |
| DisplayDeSelect | E6A5 |
| DisplayLength | 0004 |
| DisplaySelect | E6A1 |
| DisplayString | E652 |
| DivByLength | E49A |
| DoubleRotate | E2E9 |
| DtaSendLoop | E75E |

A71

CONFIDENTIAL

| | |
|---|---|
| DtaWordLength | 000A |
| EnableRTI | 0040 |
| EnableSolenoid | E867 |
| EnableTone | E620 |
| EndAbsValue | E46A |
| EndAcuity | E2E0 |
| EndAverage | E41A |
| EndBCDToAscii | E5FD |
| EndBumpFilter | E495 |
| EndCalFactor | E310 |
| EndCheckAlarm | E54C |
| EndCheckLast | E152 |
| EndCheckThr | E282 |
| EndCompute | E436 |
| EndComputeFire | E170 |
| EndDecCounter | E859 |
| EndDispString | E660 |
| EndDivide | E42E |
| EndFire | E82A |
| EndFireCheck | E240 |
| EndInspiration | E10E |
| EndIntegrate | E302 |
| EndLogOn | E926 |
| EndNormalize | E28A |
| EndProcBreath | E0C1 |
| EndProcExp | E0DE |
| EndProcFilter | E4C7 |
| EndProcInsp | E111 |
| EndSet | E787 |
| EndSignal | E6F3 |
| EndSolService | E9C8 |
| EndSpeedAdjust | E993 |
| EndSrvDuration | E572 |
| EndTransfer | E95E |
| EndUpdateCtr | E509 |
| EndUpdateMax | E2A6 |
| Exhalation | E0B1 |
| ExhaleSignBit | 0000 |
| ExtRam1 | 1040 |
| ExtRam2 | 8800 |
| ExtRam3 | 2001 |
| Filter | B83A |
| FilterCounter | B84C |
| FilterIndex | B84B |
| FilterIndex16 | B84A |
| FilterLength | 0008 |
| FireCheck | E228 |
| FireCount | B8B9 |
| FireCounter | 2008 |
| FireFlag | 202B |
| FireFlow | B8D0 |
| FireIndex | 2009 |
| FirePoints | 200B |
| FireSolenoid | E7F9 |
| FireVolume | B8D4 |
| FlowConvert | 0400 |
| FlowMeterMode | E139 |
| FlowPoints | B8C0 |
| FlowPtsLoop | E186 |
| GetDataPoint | E34A |
| GetNextFirePt | E250 |
| GetSignal | E6C1 |
| GreenLed | 0008 |
| GreenLedOff | E71D |
| GreenLedOn | E719 |
| GroupTicCnt | B874 |

A72

CONFIDENTIAL

| | |
|---|---|
| HalfDisplayLen | 0002 |
| HighCalBits | E2E1 |
| Hours | B8A5 |
| HoursDta | B8AD |
| Hysteresis | E2A7 |
| IRQ | FFF2 |
| IRQService | E9DB |
| IdleLoop | E052 |
| Inhalation | E086 |
| InhaleSignBit | 0001 |
| IntRam | 0000 |
| Integral | B870 |
| IntegralLoop | E426 |
| IntegralSecs | 0004 |
| IntegralTicCnt | B872 |
| IntegralTics | 00F0 |
| Integrate | E384 |
| Integrate1 | E398 |
| Integrate2 | E3BD |
| IntegrateFlag | B876 |
| IntegrateOff | E403 |
| IntegrateOn | E3DB |
| LastAlarm | B812 |
| LastDirection | B84F |
| LastInhaleMode | B855 |
| LastMaxFlow | B850 |
| LastMaxVol | B852 |
| LeftShift | E60F |
| LengthOffset | 0008 |
| LogDataPoint | E89D |
| LogFileEnd | 8000 |
| LogFiring | E8C7 |
| LogFlag | 2001 |
| LogFlowConvert | 000A |
| LogLength | 0003 |
| LogTicGroup | 0002 |
| LogTime | E87B |
| LoggingOff | E92B |
| LoggingOn | E8E4 |
| LowPassFilter | E460 |
| LowestToneValue | 0080 |
| MaxFlow | B885 |
| MaxFlowLoop | E211 |
| MaxIntegral | E29A |
| MaxLogFileLen | 0320 |
| MaxTics | 003C |
| MaxValue | 0200 |
| MaxVolLoop | E220 |
| MaxVolume | B887 |
| Minutes | B8A4 |
| MinutesDta | B8AC |
| ModeOffset | 0007 |
| Month | B8A8 |
| MonthDta | B8B0 |
| MoveLoop | E88C |
| NextBCDPair | E5E0 |
| NextInterval | E9A6 |
| NoiseAmplitude | 0064 |
| NormalizeLstDir | E283 |
| NumAlarms | B811 |
| NumPulses | B81F |
| NxtFireFlow | B88C |
| NxtFireVol | B8BE |
| OC1 | FFE8 |
| OC1Service | E906 |
| OC2 | FFE6 |

| | |
|---|---|
| OC2Service | E9D5 |
| OC3 | FFE4 |
| OC3Service | E9D2 |
| OC4 | FFE2 |
| OC4Service | E9CF |
| OC5 | FFE0 |
| OC5Service | E9CE |
| OpenSemaphore | E839 |
| PctFireFlow | B8D8 |
| PctFireVol | B8DA |
| PctMaxFlow | E20A |
| PctMaxVol | E219 |
| PctScratch | B8DD |
| PeakFlowMode | 0002 |
| PowerOnReset | E000 |
| ProcExpiration | E0C3 |
| ProcInspiration | E0E6 |
| ProcessBreath | E076 |
| ProcessFilter | E4AA |
| ProgBreath | E0A7 |
| ProgBreathMode | 0000 |
| ProgMode | E123 |
| ProgModePts | E16B |
| PulseArray | B823 |
| PulseCounter | B820 |
| PulseInService | E9CB |
| PulseInput | FFDA |
| PulseOvf | FFDC |
| PulseOvfService | E9CC |
| RTIFlag | 0040 |
| RTIFlagClr | 00BF |
| ReadClock | E523 |
| RealTime | FFF0 |
| RealTimeService | E9DA |
| RecSendLoop | E72F |
| ecStreamSent | E758 |
| ReceiveClockBits | E78D |
| RedLed | 0002 |
| RedLedOff | E700 |
| RedLedOn | E709 |
| RegBase | 1000 |
| ReturnUnity | E248 |
| ReturnZero | E243 |
| RunningSum | B86C |
| SWI | FFF6 |
| SWIService | E9DD |
| SampleHigh | B834 |
| SampleLow | B835 |
| SampleValue | B834 |
| SciService | E9C9 |
| ScratchCntr | B877 |
| Seconds | B8A3 |
| SecondsCntr | B837 |
| SecondsDta | B8AB |
| SelectAD | E701 |
| Semaphore | B833 |
| SendDisplayByte | E695 |
| SendSpiByte | E6B0 |
| SerialAD | 0080 |
| ServiceDuration | E568 |
| SetActiveFlag | E33F |
| SetClock | E721 |
| SetFireFlag | E85C |
| ShotCounter | B88A |
| ignBitClr | 0001 |
| SignBitMask | 0002 |

A74

CONFIDENTIAL

| Symbol | Value |
|---|---|
| SignalAmber | E2D6 |
| SignalGreen | E2D1 |
| SignalPositive | E6F2 |
| SignalRed | E2D8 |
| SixtyHertzRTI | 0002 |
| SkipCarry | E5C5 |
| SkipCompare | E53F |
| SkipLog | E373 |
| SleepSolenoid | E98D |
| SmoothValue | B84D |
| SolenoidFlgClr | 00DF |
| SolenoidForce | 0020 |
| SolenoidInt | 0020 |
| SolenoidService | E996 |
| SoundAlarm | E551 |
| SpeakerService | E964 |
| SpeedCntrl | 0001 |
| SpeedLoop | E98D |
| SpeedToneAdj | E982 |
| SpiControlMsk | 0053 |
| SpiDirMsk | 003B |
| SpiService | E9CA |
| SpiWait | E6B2 |
| StackInit | DFFF |
| StopIntegration | E307 |
| StoreLoop | E94F |
| StreamCaptured | E7F3 |
| StreamSent | E7C4 |
| TIC1 | FFEE |
| TIC1Service | E909 |
| TIC2 | FFEC |
| TIC2Service | E9D8 |
| TIC3 | FFEA |
| TIC3Service | E907 |
| TenthSec | B8A2 |
| TenthSecDta | B8AA |
| TicCounter | B836 |
| TicGroup | 0004 |
| TicSum | B86E |
| TicsPerSecond | 003C |
| TimeBytes | 0007 |
| TimeOffset | 0000 |
| TimeSet | B8A2 |
| TimeToBeep | E546 |
| TimerIntConfig | 0080 |
| TimerOvf | FFDE |
| TimerOvfFlgClr | 007F |
| TimerOvfService | E9CD |
| ToggleSoloPin | 0010 |
| ToggleToneClr | 0008 |
| ToggleToneSet | 0004 |
| ToneFlgClr | 00EF |
| ToneInt | 0010 |
| ToneOffset | 0100 |
| ToneValue | B800 |
| TrimBit | E440 |
| TrimBits | 0002 |
| TrimLowBits | E437 |
| UpdateCount | B875 |
| UpdateCounters | E4FD |
| UpdateMaxValues | E28E |
| UpdateTics | 0014 |
| UpdateToneValue | E603 |
| alidFirePoint | E260 |
| olPoints | B8C8 |
| VolPtsLoop | E19C |

A75

CONFIDENTIAL

| | |
|---|---|
| WaitForRTI | E4EB |
| WaitLonger | E68C |
| WordLength | 000E |
| XIRQ | FFF4 |
| XIRQService | E9DC |
| Year | 88A9 |
| YearDta | 88B1 |
| adctl | 0030 |
| adr1 | 0031 |
| adr2 | 0032 |
| adr3 | 0033 |
| adr4 | 0034 |
| baud | 002B |
| boot | BF40 |
| cforc | 000B |
| config | 003F |
| coprst | 003A |
| cpha | 0004 |
| ddra7 | 0080 |
| ddrc | 0007 |
| ddrd | 0009 |
| decrement | B876 |
| divide | E4A0 |
| dwom | 0020 |
| eeprom | B600 |
| hprio | 003C |
| ilie | 0010 |
| init | 003D |
| m | 0008 |
| modes | BFC0 |
| mstr | 0010 |
| oc1d | 000D |
| oc1m | 000C |
| option | 0039 |
| pacnt | 0027 |
| pactl | 0026 |
| pioc | 0002 |
| porta | 0000 |
| portb | 0004 |
| portc | 0003 |
| portcl | 0005 |
| portd | 0008 |
| porte | 000A |
| pprog | 003B |
| r8 | 0080 |
| re | 0004 |
| res1 | 0001 |
| res2 | 0006 |
| res3 | 0035 |
| res4 | 0036 |
| res5 | 0037 |
| res6 | 0038 |
| reset | FFFE |
| rie | 0020 |
| rom | E000 |
| rwu | 0002 |
| sbk | 0001 |
| sccr1 | 002C |
| sccr2 | 002D |
| scdr | 002F |
| sci | FFD6 |
| scsr | 002E |
| solenoid | 0020 |
| pcr | 0028 |
| spdr | 002A |
| spe | 0040 |

| | |
|---|---|
| speaker | 0010 |
| spi | FFD8 |
| spie | 0080 |
| spol | 0008 |
| spr0 | 0001 |
| spr1 | 0002 |
| spsr | 0029 |
| t8 | 0040 |
| tcie | 0040 |
| tcnt | 000E |
| tctl1 | 0020 |
| tctl2 | 0021 |
| te | 0008 |
| test1 | 003E |
| tflg1 | 0023 |
| tflg2 | 0025 |
| tic1 | 0010 |
| tic2 | 0012 |
| tic3 | 0014 |
| tie | 0080 |
| tmsk1 | 0022 |
| tmsk2 | 0024 |
| toc1 | 0016 |
| toc2 | 0018 |
| toc3 | 001A |
| toc4 | 001C |
| toc5 | 001E |
| vectors | FFD6 |
| wake | 0004 |

We claim:

1. A method for delivering an aerosol of a narcotic to a subject for inspiration, said method characterized by:

monitoring inspiratory flow;

calculating a firing threshold parameter based on the monitored inspiratory flow;

determining whether each detected inspiratory flow is one of a first flow detected following a reset flow event or a subsequent flow detected following a detected flow that is not followed by a reset flow event, the reset flow event being any of a release of an amount of a narcotic and initialization of operation of the apparatus;

selecting a delivery threshold corresponding to a point in the detected inspiratory flow at which an amount of an aerosol of the narcotic is to be released characterized by selecting a preselected delivery threshold in response to the detected inspiratory flow being a determined first flow and selecting a calculated delivery threshold that is calculated based on a sensed flow parameter of the preceding detected inspiratory flow in response to the detected inspiratory flow being a determined subsequent flow; and determining whether or not the detected inspiratory flow satisfies the selected delivery threshold, and (i) in response to the detected inspiratory flow satisfying the selected delivery threshold, releasing an amount of the narcotic to generate an aerosol of the narcotic; and (ii) in response to determining that the detected inspiratory flow did not satisfy the selected delivery threshold, calculating a new delivery threshold based on the detected inspiratory flow so that the selected delivery threshold for the next detected inspiratory flow determined to be a subsequent flow is the last calculated delivery threshold.

2. The method of claim 1, wherein the narcotic is an opiate derivative.

3. The method of claim 2, wherein the opiate derivative is morphine.

4. A method for administering an aerosol of a narcotic, said method characterized by:

(a) monitoring inspiratory flow of a subject through an inspiratory flow path;

(b) automatically determining, based on a selected flow or volume parameter of a first monitored inspiratory flow, a delivery threshold for the release of an amount of an aerosol of a narcotic; and (c) delivering in response to a second monitored inspiratory flow satisfying the determined delivery threshold an amount of aerosol of the narcotic for inspiration during the second monitored inspiratory flow, the second monitored inspiratory flow following the first monitored inspiratory flow.

5. The method of claim 4, wherein the narcotic is an opiate derivative.

6. The method of claim 5, wherein the opiate derivative is morphine.

7. A method for controlling inhalation therapy using an inhaler device for releasing an amount of an aerosol of a narcotic for inspiration by a patient in response to a sufficient inspiratory flow characterized by:

monitoring a patient's breath flow including the inspiratory flow;

determining a pulmonary function based on a detected breath flow, the determined pulmonary function being selected from among the group consisting of forced expiratory volume, forced vital capacity, and peak expiratory flow rate;

comparing a first determined pulmonary function based on a first detected breath flow and a second determined pulmonary function based on a second detected breath flow;

determining relative changes in the determined pulmonary function in response to an aerosol of a narcotic released over time; and displaying a parameter corresponding to the determined relative changes in the first and second determined pulmonary functions.

8. The method of claim 7, wherein the narcotic is an opiate derivative.

9. The method of claim 8, wherein the opiate derivative is morphine.

* * * * *